US012059459B2

(12) United States Patent
Granum et al.

(10) Patent No.: US 12,059,459 B2
(45) Date of Patent: Aug. 13, 2024

(54) THERAPEUTIC ANTICANCER NEOEPITOPE VACCINE

(71) Applicant: Nykode Therapeutics ASA, Oslo (NO)

(72) Inventors: Stine Granum, Oslo (NO); Elisabeth Stubsrud, Oslo (NO); Agnete Brunsvik Fredriksen, Rælingen (NO)

(73) Assignee: Nykode Therapeutics ASA, Oslo (NO)

( * ) Notice: Subject to any disclaimer, the term of this patent is extended or adjusted under 35 U.S.C. 154(b) by 405 days.

(21) Appl. No.: 17/557,988

(22) Filed: Dec. 21, 2021

(65) Prior Publication Data

US 2022/0370579 A1    Nov. 24, 2022

Related U.S. Application Data

(63) Continuation of application No. 16/068,449, filed as application No. PCT/EP2017/050206 on Jan. 5, 2017, now abandoned.

(30) Foreign Application Priority Data

Jan. 8, 2016  (EP) ..................................... 16150574
Jul. 7, 2016  (EP) ..................................... 16178393

(51) Int. Cl.
| G01N 31/00 | (2006.01) |
| A61K 39/00 | (2006.01) |
| A61P 35/00 | (2006.01) |
| G01N 33/53 | (2006.01) |

(52) U.S. Cl.
CPC .......... *A61K 39/0011* (2013.01); *A61P 35/00* (2018.01); *A61K 2039/53* (2013.01); *A61K 2039/6031* (2013.01); *A61K 2039/6056* (2013.01); *A61K 2039/627* (2013.01); *A61K 2039/64* (2013.01); *A61K 2039/70* (2013.01)

(58) Field of Classification Search
None
See application file for complete search history.

(56) References Cited

U.S. PATENT DOCUMENTS

| 5,580,859 | A  | 12/1996 | Felgner et al. |
| 5,646,016 | A  | 7/1997  | McCoy et al. |
| 6,099,846 | A  | 8/2000  | Levy et al. |
| 6,306,397 | B1 | 10/2001 | Edwards et al. |
| 7,223,408 | B2 | 5/2007  | Cassetti |
| 8,932,603 | B2 | 1/2015  | Bogen et al. |
| 9,169,322 | B2 | 10/2015 | Bogen et al. |
| 9,901,635 | B2 | 2/2018  | Brekke et al. |
| 2003/0100497 | A1 | 5/2003 | Baker et al. |
| 2004/0253238 | A1 | 12/2004 | Bogen et al. |
| 2005/0069549 | A1 | 3/2005 | Herman |
| 2006/0165713 | A1 | 7/2006 | Gough et al. |
| 2007/0065444 | A1 | 3/2007 | North et al. |
| 2007/0298051 | A1 | 12/2007 | Barouch et al. |
| 2008/0102084 | A1 | 5/2008 | Wu et al. |
| 2009/0010948 | A1 | 1/2009 | Huang et al. |
| 2009/0092578 | A1 | 4/2009 | Su et al. |
| 2011/0263835 | A1 | 10/2011 | Ting et al. |
| 2013/0033697 | A1 | 12/2013 | Ruffini et al. |
| 2019/0022202 | A1 | 1/2019 | Granum et al. |

FOREIGN PATENT DOCUMENTS

| EP | 920522 | 2/1998 |
| EP | 3053592 A1 | 8/2016 |
| JP | 2013/532971 | 8/2013 |
| JP | 2014/523406 | 9/2014 |
| WO | WO 92/13955 | 8/1992 |
| WO | WO 92/16636 | 10/1992 |
| WO | WO 95/32731 | 12/1995 |
| WO | WO 99/58552 | 11/1999 |
| WO | WO 00/156683 | 3/2000 |
| WO | WO 02/04664 A2 | 1/2002 |
| WO | WO 2002/060919 | 8/2002 |
| WO | WO 03/059952 | 7/2003 |
| WO | WO 2003/059951 | 7/2003 |
| WO | WO 2003/084467 | 10/2003 |
| WO | WO 2003/087162 | 10/2003 |
| WO | WO 2003/096017 | 11/2003 |
| WO | WO 2003/106692 | 12/2003 |
| WO | WO 2004/030636 | 4/2004 |
| WO | WO 2004/076489 | 9/2004 |

(Continued)

OTHER PUBLICATIONS

Ruffini et al. (Vaccine, Vo.29, 2011, pp. 191-199). (Year: 2011).*
Bendandi, M., C. D. Gocke, et al. (1999). "Complete molecular remissions induced by patient-specific vaccination plus granulocyte-monocyte colony-stimulating factor against lymphoma." Nat Med 5(10): 1171-7.
Biragyn et al., Genetic Fusion of Chemokines to a Self Tumor Antigen Induces Protective, T-cell Dependent Antitumor Immunity; Nature Biotechnology; V 17; Mar. 1999; pp. 253-258.
Biragyn et al., Tool-Like Receptor 4-Dependent Activation of Dendritic Cells by Beta-Detensin 2; Science, V 298; Nov. 2002; pp. 1025-1029.
Bogen, B. (1989). "Monoclonal antibodies specific for variable and constant domains of murine lambda chains." Scand J Immunol 29(3): 273-9.
Bogen, B. and J.D. Lambris (1989). "Minimum length of an idiotypic peptide and a model for its binding to a major histocompatibility complex class II molecule." Embo J 8(7): 1947-52.
Bogen, B., B. Malissen, et al. (1986). "Idiotope-specific T cell clones that recognize syngeneic immunoglobulin fragments in the context of class II molecules." Eur J Immunol 16(11): 1373-8.

(Continued)

*Primary Examiner* — Lisa V Cook
(74) *Attorney, Agent, or Firm* — Hamilton, Brook, Smith & Reynolds, P.C.

(57) ABSTRACT

The present invention relates to an anticancer vaccine which includes polynucleotides or polypeptides, methods of treatment of cancer wherein such an anticancer vaccine is used as well as methods for producing the vaccine. The vaccine includes a polynucleotide with a nucleotide sequence encoding a targeting unit, a dimerization unit, a first linker and an antigenic unit. The antigenic unit includes from 3 to 50 antigenic subunits separated by a second linker with each antigenic subunit having at least a part of a cancer neoepitope sequence. The vaccine can include a polypeptide encoded by the polynucleotide or a dimeric protein with two polypeptides encoded by the polynucleotide.

22 Claims, 13 Drawing Sheets

Specification includes a Sequence Listing.

(56) References Cited

FOREIGN PATENT DOCUMENTS

| WO | WO 2004/111075 | 12/2004 |
|---|---|---|
| WO | WO 2005/089792 | 9/2005 |
| WO | WO 2006/002114 | 1/2006 |
| WO | WO 2006/138567 | 12/2006 |
| WO | WO 2007/031222 | 3/2007 |
| WO | WO 2007/101227 | 9/2007 |
| WO | WO 2008/014521 | 1/2008 |
| WO | WO 2008/138648 | 11/2008 |
| WO | WO 2009/003623 | 1/2009 |
| WO | WO 2009/039341 | 3/2009 |
| WO | WO 2009/053401 | 4/2009 |
| WO | WO 2011/143656 | 11/2011 |
| WO | WO 2011/161244 A1 | 12/2011 |
| WO | WO 2012/159643 A1 | 11/2012 |
| WO | WO 2012/159754 | 11/2012 |
| WO | WO 2013/112549 | 8/2013 |
| WO | WO 2014/052707 | 4/2014 |
| WO | WO 2014/082729 | 6/2014 |
| WO | WO 2014/165291 | 10/2014 |
| WO | WO 2014/168874 | 10/2014 |
| WO | WO 2014/180490 | 11/2014 |
| WO | WO 2015/085233 | 6/2015 |
| WO | WO 2016/081947 | 5/2016 |
| WO | WO 2016/128060 | 8/2016 |
| WO | WO 2016/191545 | 12/2016 |
| WO | WO 2017/066256 | 4/2017 |
| WO | WO 2017/066290 | 4/2017 |
| WO | WO 2017/066339 | 4/2017 |
| WO | WO 2017/118702 | 7/2017 |
| WO | WO 2017/165464 | 9/2017 |
| WO | WO 2017/173321 | 10/2017 |
| WO | WO 2017/194170 | 11/2017 |
| WO | WO 2017/194610 | 11/2017 |
| WO | WO 2017/205810 | 11/2017 |
| WO | WO 2017/222619 | 12/2017 |
| WO | WO 2018/015433 | 1/2018 |
| WO | WO 2018/102613 | 6/2018 |
| WO | WO 2018/106699 | 6/2018 |
| WO | WO 2018/112449 | 6/2018 |
| WO | WO 2018/148381 | 8/2018 |
| WO | WO 2018/148671 | 8/2018 |

OTHER PUBLICATIONS

Bogen, B., L. Gleditsch, et al. (1992). "Weak positive selection of transgenic T cell receptor-bearing thymocytes: importance of major histocompatibility complex class II, T cell receptor and CD4 surface molecule densities." European Journey of Immunology 22(3): 703-9.

Borysiewicz et al Lancet, 347: 1523-1527, 1996.

Bronte, "Genetic vaccination for the active immunotherapy of cancer." Curr. Gene Therapy 1:53-100, 2001.

Brunsvik, A et al., "Vaccibodies: Future Vaccines for B Cell Lymphoma and Myeloma?" Institute of Immunology, Univ of Oslo, Oslo National Hospital; Oslo, NO, Abstract, 2003, 1 page.

Brunsvik, A et al; Construction of Tetrabodies for Cancer Vaccines; Institute of Immunology, University of Oslo; Oslo National Hospital, Oslo, Norway, abstract, 2002, 1 page.

Brunsvik, A et al; Construction of Tetrabodies for Cancer Vaccines; The National Hospital, University of Oslo; abstract 2002.

Cannon, G. and Weissman, D.: "RNA Based Vaccines", DNA and Cell Biology, vol. 21, No. 12, 2002, © Mary Ann Liebert, Inc., pp. 953-961.

Casten, L. A. and S K Pierce (1988) "Receptor-mediated B cell antigen processing Increased antigenicity of a globular protein covalently coupled to antibodies specific for B cell surface structures" J Immunol 140(2): 404-10.

Chen et al, Linkage of CD40L to a Self-Tumor Antigen Enhances the Anti-Tumor Immune Response to Dendritic Cell-Based Treatment; Cancer Immunoll Immunother; V. 51, 2002; pp. 341-348.

Cheung et al, "Plasmid encoding papillomavirus Type 16 (HPV16) DNA constructed with codon optimization improved he immunogenicity against HPV infection", Vaccine. Dec. 16, 2004; 23(5):629-38.

Chudley et al., DNA Fusion-Gene Vaccination in patients with prostate cancer induces high-frequency CDB T-cell Responses and increases PSA doubling time; Cancer Immunoll Immunother, 2012, 61:2161-2170.

Crook et al., "Degradation of P53 can be Targeted by HPV E6 Sequences Distinct from Those Required for p53 Binding and Trans-Activation", Cell, 1991, vol. 67, pp. 547-556, Cell Press.

Dalal et al, "Mutational Analysis of Human Papillomavirus Type 14 E6 Demonstrates that p53 Degradation is Necessary for Immortalization of Mammary Epithelial Cells," Journal of Virology, 1996, pp. 683-688, American Society for Microbiology.

Dennis, "Off by a whisker", Nature Pub 442:739-741, 2006.

Dong et al, "Determination of the binding affinity of different human papillomavirus E7 proteins for the tumor suppressor pRb by a plate-binding assay" J Virol Methods Oct. 2001; 98(1): 91-8.

Drew et al, "The human IgG3 hinge mediates the formation of antigen dimers that enhance humoral immune responses to DNA immunisation.", Vaccine. Jul. 20, 2001; 19(30):4115-20.

Eisen et al, "Lambda Chains and Genes in Inbred Mice," Ann Rev Immunol. 3: 337-365; 1985.

Eisen et al, "Mouse Myeloma Proteins with Antihapten Antibody Activity. The Protein Produced by Plasma Cell Tumor MOPC-315," Biochem 7(11): 4126-4134; 1968.

Fredriksen, Agnete B., Sandlie, Inger, and Bogen, Bjarne, "DNA Vaccines Increase Immunogenicity of Idiotypic Tumor Antigen by Targeting Novel Fusion Proteins to Antigen-Presenting Cells", Molecular Therapy, vol. 13, No. 4, Apr. 2006.

Fredriksen, Agnete and Bogen, Bjarne, "Chemokine-idiotype fusion DNA vaccines are potentiated by bivalency, and xenogeneic sequences", Blood, vol. 110, No. 6, p. 1797-1805, Sep. 15, 2007.

Frøyland et al, "Targeted idiotype-fusion DNA vaccines for human multiple myeloma: preclinical testing," European Journal of Haematology, vol. 86, pp. 385-395, 2011.

Genbank: AAP36497 .1 Homo sapiens chemokine (C-C motif) ligand 3, partial [synthetic construct]. Dated May 13, 2003.

Glick. Defending Pharma Companies: Innovation is Alive and Well in the Therapeutic Drug Industry. Gen. Engineer, News 28(7), pp. 6 and 9, Apr. 1, 2008.

Grodeland et al., Antigen Targeting to Human HLA Class II Molecules Increases Efficacy of DNA Vaccination, Immunol 2016; 197:3375-3585.

Gulliver, G., et al., "Both Conserved Region 1 (CR1) and CR2 of the Human Papillomavirus Type 16 E7 Oncogene are Required for Induction of Epidermal Hyperplasia and Tumor Formation in Transgenic Mice," Journal of Virology, 1997, vol. 71(8), pp. 5905-5914.

Hakim. I , S. Levy, et al (1996) "A nine-amino acid peptide from IL-1beta augments antitumor immune responses induced by protein and DNA vaccines" J Immunol 157(12): 5503-11.

Haupt et al., "The Potential of DNA Vaccination against Tumor-Associated Antigens for Antitumor Therapy," Exp Biol Med 227, v: 227-237, 2002.

Hoogenboom, Mix and Match: Building Manifold Binding Sites; Nature Biotechnology; V 15, Feb. 1997; pp. 125-226.

Horwell, D C., "The 'peptoid' approach to the design of non-peptide, small molecule agonists and antagonists of neuropeptides," Trends in Biotechnology, 1995, pp. 132-134, vol. 13(4).

Hough, D W., R. P. Eady, et al (1976) "Anti-idiotype sera raised against surface immunoglobulin of human neoplastic lymphocytes" J Exp Med 144(4): 960-9.

Hu et al., Minibody., A Novel Engineered Anti-Carcinoembryotic Antigen Antibody Fragment (Single-Chain Fv-CH3), Which Exhibits Rapid, High-Level Targeting of Xenografts; Cancer Research, V 56, Jul. 1996; pp. 3055-3061.

Huang et al., "DNA vaccine encoding heat shock protein 60 co-linked to HPV16 E6 and E7 tumor antigens generates more potent immunotherapeutic effects than respective E6 or E7 tumor antigens." Gynecol Oncol. Dec. 2007; 107(3):404-12. Epub Oct. 1, 2007.

(56) References Cited

OTHER PUBLICATIONS

Huang et al., Enhanced Antitumor Immunity by Fusion of CTLA-4 to a Self Tumor Antigen; Blood, V 96; No. 12, Dec. 2000; pp. 3663-3670.
Huang et al., Improved Immunegenicity of Self Tumor Antigen by Covalent Linkage to DC40 Ligand; Int. J_ Cancer, V O8, 2004; pp. 696-703.
International Searching Authority, International Search Report and Written Opinion for International Application No. PCT/EP2012/076404, Mar. 25, 2013, 15 pages, European Patent Office, The Netherlands.
Kim et al., "Enhanced immunogenicity of human papillomavirus 16 L 1 genetic vaccines fused to an ER-targeting secretory signal peptide and Rantes." Gene Therapy (2003), vol. 10, pp. 1268-1273.
King, C. A., M. B. Spellerberg, et al. (1998). "DNA vaccines with single-chain Fv fused to fragment C of tetanus toxin induce protective immunity against lymphoma and myeloma." Nat Med 4(11): 1281-6.
Knappscog, S., et al., "The level of synthesis and secretion of Gaussia princeps luciferase in transfected CHO cells heavily dependent on the choice of signal peptide," Journal of Biotechnology, 2007, vol. 128, pp. 705-715.
Kreiter, Sebastian et al., "Mutant MHC class II epitopes drive therapeutic immune responses to cancer", Nature, vol. 20, No. 7549, p. 692-696, Apr. 30, 2015, XP55231810A.
Kriangkum et al., Bispecific and Bifunctional Single Chain Recombinant Antibodies; Biomolecular Engineering; v 18:2, 2001; pp. 31-40.
Kristoffersen, G., K. Hannestad, et al. (1987). "Two M315 idiotopes defined by isologous monoclonal antibodies: one depends on germline and the other on mutated murine lambda 2 light chain sequences," Scand J Immunol 26(5), pp. 535-546.
Kutzler, M et al.; DNA Vaccines; Ready for Prime Time ?; Nature Reviews Genetics, V 9, 2008, pp. 776-788.
Lambert et al., DNA Vaccines Encoding Antigen Targeted to MHC Class II Induce Influenza-Specific CD8+ T Cell Responses, Enabling Faster Resolution of Influenza Disease. Frontiers in Immunology Aug. 2016. v7, article 321, pp. 1-11.
Lauritzsen, G. F., S. Weiss, et al. (1993). "Anti-tumour activity of idiotype-specific, MHC-restricted Th1 and Th2 clones in vitro and in vivo." Scand J Immunol 37(1): 77-85.
Lauritzsen, G. F., S. Weiss, et al. (1994). "Naive idiotype-specific CD4+ T cells and immunosurveillance of B-cell tumors." Proc Natl Acad Sci USA 91(12): 5700-4.
Lewis, A.D., et al., Generation of Neutralizing Activity against Human Immunodeficiency Virus Type 1 in Serum by Antibody Gene Transfer, J. Virol., 76(17), pp. 8769-8775, 2002.
Lunde et al., Troybodies and Pepbodies; Biochemical Society Transactions, V 30; part 4, 2002; pp. 500-506.
Lunde et al., Troy-bodies: Recombinant Antibodies that Target T cell Epitopes to Antigen Presenting Cells; Intern. REV Immunol. V 20, 2001; pp. 647-673.
Lunde, E., K. H. Western, et al. (2002). "Efficient delivery of T cell epitopes to APC by use of MHC class II-specific Troybodies." J Immunol168(5): 2154-62.
Lunde, E., L. A. Munthe, et al. (1999). "Antibodies engineered with ID specificity efficiently deliver integrated T-cell epitopes for antigen presentation by B cells." Nat Biotechnol 17(7): 670-5.
Lunde, E., I. B. Rasmussen, et al. (2001). "Troy-bodies': antibodies as vector proteins for T cell epitopes." Biomol Eng 8(3): 109-16.
MacGregor et al; T-cell Responses Induced in Normal Volunteers Immunized with a DNA-based Vaccine Containing HIV-1 env and rev; AIDS 2002; V 16, pp. 2137-2143.
Martoglio, B., et al., "Signal sequences: more than just greasy peptides," trends in Cell Biology, 1998, vol. 8, pp. 410-415.
Menten, P., et al., "The LD78B insoform of MIP-1a is the most potent CCr5 agonist and HIV-1-inhibiting chemokine," The Journal of Clinical Investigation, 1999, pp. R1-R5, vol. 104(4).

Mesplède et al., "p53 Degradation Activity, Expression, and Subcellular Localization of E6 Proteins from 29 Human Papillomavirus Genotypes," Journal of Virology, 2011, vol. 86, No. 1, pp. 94-107.
Moody et al., "Human papillomavirus oncoproteins: pathways to transformation," Nature Reviews Cancer, 2010, vol. 10, pp. 550-560.
Münger et al., "Complex formation of human papillomavirus E7 proteins with the retinoblastoma tumor suppressor gene product," The EMBO Journal, 1989, vol. 8, No. 13, pp. 4099-4105.
Münger et al., "E6 Alignments HPV Compendium," 1997, 24 pp.
Münger et al., "E7 Alignments HPV Compendium," 1997, 22 pp.
Nagakawa et al., "Mutational Analysis of Human Papillomavirus Type 16 E6 Protein: Transforming Function for Human Cells and Degradation of p53 in vitro," Virology, 2002, vol. 76, No. 24, pp. 13039-13048.
Neuberger, M. S. (1983). "Expression and regulation of immunoglobulin heavy chain gene transfected into lymphoid cells." Embo J 2(8): 1373-8.
Nguyen et al. A mutant of human papillomavirus type 16 e6 deficient in binding alpha-helix partners displays reduced oncogenic potential in vivo. J Virol. Dec. 2002; 76(24 ): 13039-48.
Noel, D., et al; High in vivo Production of Model Monoclonal Antibody on Adenoviral Gene Transfer, Hum. Gene Ther., 13(12), pp. 1483-1493, 2002.
Nominé•et al., "Structural and Functional Analysis of E6 Oncoprotein: Insights in the Molecular Pathways of Human Papillomavirus-Mediated Pathogenesis," Molecular Cell, 2006, vol. 21, pp. 665-678.
Norderhaug, L., T. Olafsen, et al. (1997). Versatile vectors for transient and stable expression of recombinant antibody molecules in mammalian cells. J Immunol Methods 204(1): 77-87.
NP_41325.1 transforming protein E6 [Human papillomavirus type 16] Oct. 27, 2010, 2 pages.
NP_41326.1 transforming protein E7 [Human papillomavirus type 16] Oct. 27, 2010, 3 pages.
Olafsen, T., I. B. Rasmussen, et al. (1998). "IgM secretory tailpiece drives multimerisation of bivalent scFv fragments in eukaryotic cells." Immunotechnology 4(2): 141-53.
Øynebraten, I et al., "P19-39. Vaccibodies: a Novel Vaccine Strategy for HIV that Target Viral Antigens to APC (Poster Presentation)," Retrovirology, 2009, vol. 6, Suppl. 3, p. 359, BioMed Central Ltd.
Oynebraten et al., Generation of Antibody-Producing Hybridomas Following One Single Immunization with a Targeted DNA Vaccine, Scandinavian Journal of Immunology 2011; v75, pp. 379-488.
Oynebraten et al., Increased Generation of HIV-1 gp120-Reactive Cdb+ T Cells by a DNA Vaccine Construct Encoding the Chemokine CCL3, PLOS One, Aug. 2014, v9, issue 8, pp. 1-11.
Ozato, K., N. Mayer, et al. (1980). "Hybridoma cell lines secreting monoclonal antibodies to mouse H-2 and Ia antigens." J Immunol 124(2): 533-40.
Phelps, W., et al., "Structure-Function Analysis of the Human Papillomavirus Type 16 E7 Oncoprotein," Journal of Virology, 1992, vol. 66(4), pp. 2418-2427.
Pluckthun et al., New Protein Engineering Approaches to Multivalent and Bispecific Antibody Fragments; Immunotechnology, V. 3, 1997; pp. 83-105.
Poláková et al., "DNA vaccine against human papillomavirus type 16: Modifications of E6 oncogene," Vaccine, 2010, vol. 28, pp. 1506-1513.
Proost et al., "Cleavage of CD26/dipeptidyl peptidase IV converts the chemokine LD78beta into a Most Efficient Monocyte Attractant and CCR1 Agonist," *Blood*, 2000.
Ravetch, J. V. and S. Bolland (2001). "IgG Fc receptors." Annu Rev Immunol 19: 275-90.
Ristriani T. et al., A single-codon mutation converts HPV 16 E6 oncoprotein into a potential tumor suppressor, which induces p53-dependent senescence of HPV-positive Hela cervical cancer cells, Oncogene 28, p. 762-772, 2009.
Rochlitz C.F., "Gene Therapy of Cancer," Swiss Medicine Weekly, 131 :4-9, 2001.
Ruffini et al., "Human chemokine MIP1alpha increases efficiency of targeted DNA fusion vaccines," Vaccine, 2011, pp. 191-199, vol. 29.

(56) References Cited

OTHER PUBLICATIONS

Ruffini et al., Idiotypic Vaccination for B-cell Malignancies as a Model for Therapeutic Cancer Vaccines: From Prototype Protein to Second Generation Vaccines; Haematologica; vol. 87, 2002, pp. 989-1001.

Ruffini, et al., "Targeted DNA vaccines eliciting crossreactive anti-idiotypic antibody responses against human B cell malignancies in mice," *Journal of Translational Medicine*, 2014, vol. 12(207), pp. 1-12.

Schall, T., et al., "Human Macrophage Inflammatory Protein a (MIP-1 a) and MIP-1 B Chemokines Attract Distinct Populations of Lymphocytes," J. Exp. Med., 1993, vol. 177, pp. 1821-1826.

Schiavo et al. Blood, 107:4597-4605, 2006.

Schjetne et al., "Delivery of Antigen to CD40 Induces Protective Immune Response against Tumors," J. Immunol. 178:4169-4176; 2007.

Schulenburg et al., Amino Acid Sequence of the Light Chain from a Mouse Myeloma Protein with Anti-Hapten Activity: Evidence for a Third Type of Light Chain, ONAS 68:2623-2626, 1971.

Simon, R. J., et al., "Peptoids: A modular approach to drug discovery," Proceedings of the National Academy of Sciences of the United States of America, 1992, pp. 9367-9371, vol. 89(20).

Sirisinha, S. and H. N. Eisen (1971). "Autoimmune-like antibodies to the ligand-binding sites of myelomaproteins." Pro Natl Acad Sci U S A 68(12): 3130-5.

Slavin-Chiorini et al., "Biologic Properties of a CH2 Domain-Deleted Recombinant Immunoglobin," Int. J. Can. 53:97-103, 1993.

Snider, D. P. and D. M. Segal (1987). "Targeted antigen presentation using crosslinked antibody heteroaggregates." J Immunol 139(5): 1609-16.

Snodgrass, H. R., et al., "Restricted a/B receptor gene usage of idiotype-specific major histocompatibility complex-restricted T cells: selection for CDR3-related sequences," European Journal of Immunology, 1992, pp. 2169-2172.

Stevenson et al., "DNA Vaccines to attack cancer," PNAS 101:14646-14652; 2004.

Tang et al; Genetic Immunization is a Simple Method for Eliciting an Immune Response; Nature, 1992, V356; abstract.

Tang, D.C., et al., "Genetic Immunization is a Simple Method for Eliciting an Immune Response," Nature, 1992, pp. 152-154, vol. 356(6365).

Tao, et al. (1993). "Idiotype/granulocyte-macrophage colony-stimulating factor fusion protein as a vaccine or B-cell lymphoma." Nature 362(6422): 755-8.

The Norwegian Biotechnology Advisory Board—Discussion Paper, Regulation of DNA Vaccines and Gene Therapy on Animals, 2003.

Tjelle, et al. (2004). "Monoclonal antibodies produced by muscle after plasmid injection and electroporation." J Mol Ther.

Tollefsen, S., T. Tjelle, et al. (2002). "Improved cellular and humeral immune responses against Mycobacterium tuberculosis antigens after intramuscular DNA immunisation combined with muscle electroporation." Vaccine 20 27-28):3370-8.

Tunheim, G., et al., Human receptors of innate immunity (CD14, TLR2) are promising targets for novel recombinant Immunoglobulin-based vaccine candidates, Vaccine, 2007, pp. 4723-4734, vol. 25(24).

Ulmer, Jeffrey B. et al.: "RNA-based vaccines" Elsevier, Vaccine 30, Feb. 2012, p. 4414-4418.

Van Spriel et al., Immunotherapeutic Perspective for Bispecific Antibodies; Immunology Today; V 21; No. 8, Aug. 2000; pp. 391-396.

Verma, et al., "Gene Therapy-Promises, Problems, and Prospects," Nature, vol. 389, p. 239-242, 1997.

Vile et al., "Cancer Gene Therapy: Hard Lessons and New Courses," Gene Therapy, V7; pp. 2-8; 2000.

Voskoglou-Nomikos, "Clinical Predictive Value of the in Vitro Cell Line, Human Xenograft, and Mouse Allograft Preclinical Cancer Models," Clin. Can.Res .; 9:4227-4239; 2003.

Wang, R., et al., "Induction of Antigen-Specific Cytotoxic T Lymphocytes in Humans by a Malaria DNA Vaccine," Science, 1998, pp. 476-480, vol. 282.

WIKI Gene therapy—https://en.1vikipedia.org/lviki/Gene_therapy— Retrieved on Feb. 4, 2020.

Wolff et al., The Mechanism of Naked DNA Uptake and Expression; Adv Genet. 2005, 54:3-20, pp. 1-3.

Xie et al., "Transforming Activity of a Novel Mutant of HPV16 E6E7 Fusion Gene," Virologica Sinica, 2011, vol. 26, No. 3, pp. 206-213.

International Search Report and Written Opinion received for PCT Patent Application No. PCT/EP2017/050206, "Therapeutic Anticancer Neoepitope Vaccine", mailed on Apr. 21, 2017, 13 pages.

Notification Concerning Transmittal of International Preliminary Report on Patentability for International Application No. PCT/EP2017/050206, "Therapeutic Anticancer Neoepitope Vaccine" date of mailing: Jul. 19, 2018, 10 pages.

Kato, A., et al., Methods for Enhancing Protein Solubility and the Effect of SEP-Tags on Protein Solubility, May 2008, Seibutsu Butsuri 48(3):185-189. (w/partial translation of reference and Japanese Office Action).

* cited by examiner

THERAPEUTIC ANTICANCER NEOEPITOPE VACCINE

CROSS REFERENCE TO RELATED APPLICATIONS

This application is a continuation of U.S. application Ser. No. 16/068,449, filed Jul. 6, 2018, now abandoned, which is a national stage filing under 35 U.S.C. 371 of PCT/EP2017/050206, filed Jan. 5, 2017, which International Application was published by the International Bureau in English on Jul. 13, 2017, and claims priority from European Application Nos. 16150574.8, filed Jan. 8, 2016, and 16178393.1, filed Jul. 7, 2016, which applications are hereby incorporated by reference in their entirety in this application.

REFERENCE TO A SEQUENCE LISTING SUBMITTED ELECTRONICALLY AS A TEXT FILE

The instant application contains a Sequence Listing which has been submitted in ASCII format via EFS-Web and is hereby incorporated by reference in its entirety. Said ASCII copy, created on Sep. 16, 2021, is named V89540_1050US_PCT_0006_1_Seq_List.txt, and is 134960 bytes in size.

FIELD OF INVENTION

The present invention relates to an anticancer vaccine comprising polynucleotides or polypeptides, methods of treatment of cancer wherein such an anticancer vaccine is used as well as methods for producing the vaccine.

BACKGROUND OF INVENTION

Although treatment of cancer has been improved over the past few decades in particularly due to early detection and diagnosis, which has significantly increased the survival, only about 60% of patients diagnosed with cancer are alive 5 years after the diagnosis.

Most of the cancer treatments in use are surgical procedures, radiation and cytotoxic chemotherapeutics, however they all have serious side effects. Recently also treatment using antibodies directed towards known cancer associated antigens is used.

Within the last few years cancer immune therapies targeting cancer cells with the help of the patient's own immune system, i.e. cancer vaccines, have attracted interest because such therapies may reduce or even eliminate some of the side-effects seen in the traditional cancer treatment.

The foundation of immunology is based on self-nonself discrimination. Most of the pathogens inducing infectious diseases contain molecular signatures that can be recognized by the host and trigger immune responses. However tumor cells are derived from normal cells, and do not generally express any molecular signatures, making them more difficult to be distinguished from normal cells.

Nevertheless, most tumor cells express different types of tumor antigens. One class of tumor antigens are the so-called tumor associated antigens, i.e. antigens expressed at low levels in normal tissues and expressed at a much higher level in tumor tissue. Such tumorassociated antigens have been the target for cancer vaccines for the last decade. However, immunological treatment directed towards tumor associated antigens exhibit several challenges, in that the tumor cells may evade the immune system by downregulating the antigen in question, and the treatment may also lead to toxicities due to normal cell destruction.

Recently, another class of tumor antigens have been identified, the so-called tumor neoantigens or tumor specific-antigens. Tumor neoantigens arise due to one or more mutations in the tumor genome leading to a change in the amino acid sequence of the protein in question. Since these mutations are not present in normal tissue, the side-effects of the treatment directed towards the tumor associated antigens do not arise with an immunologic treatment towards tumor neoantigens.

The average number of somatic, tumor-specific non-synonymous mutations for malignant melanoma is between 100 and 120. Some of the genetic alterations can be recognized by the immune system, representing ideal antigens. Animal models have confirmed the utility of immunization with tumor neoantigens, and two clinical trials have been initiated, one with a vaccine comprising up to 10 mutated proteins and the other with an RNA vaccine (IVAC MUTANOME). The RNA vaccine comprises 2 RNA molecules each comprising five different mutation-encoding sequences.

However, by administration of either several different proteins or several RNA sequences it is difficult to control the immunological response to the various proteins administered or expressed in vivo.

Accordingly, there is a need for a more efficient vaccine ensuring expression of the mutated proteins either in vivo or in vitro and ensure delivery of the antigen as well as activation of the antigen presenting cells needed to elicit a strong T cell response.

SUMMARY OF INVENTION

The present invention relates to a therapeutic anticancer vaccine being directed to a plurality of neoepitopes from tumor neoantigens, wherein the neoepitopes are presented to the immune system as a dimeric protein called a vaccibody. WO 2004/076489 describes dimeric proteins called vaccibodies in detail.

In one embodiment the invention relates to a therapeutic anticancer neoepitope vaccine comprising an immunologically effective amount of 1) a polynucleotide comprising a nucleotide sequence encoding
   a targeting unit
   a dimerization unit
   a first linker
   an antigenic unit, wherein said antigenic unit comprises n−1 antigenic subunits, each subunit comprising at least a part of a cancer neoepitope sequence and a second linker and said antigenic unit further comprising a final cancer neoepitope sequence, wherein n is an integer of from 3 to 50.
   or
2) a polypeptide encoded by the polynucleotide as defined in 1), or
3) a dimeric protein consisting of two polypeptides encoded by the polynucleotide as defined in 1).

In another aspect, the invention relates to the polynucleotide as defined above. Such polynucleotide is e.g. useful in a vaccine according to the invention.

In a third aspect the invention relates to a vector comprising the polynucleotide as defined above, and in a fourth aspect the invention relates to a host cell comprising the polynucleotide or the vector as defined above.

In a fifth aspect the invention relates to a polypeptide encoded by the polynucleotide as defined above. Such polypeptide is e.g. useful in a vaccine according to the invention, and in a sixth aspect the invention relates to a dimeric protein consisting of two polypeptides as defined above.

In a seventh aspect the invention relates to the polypeptide, the dimeric protein, or the polynucleotide as defined above for use as a medicament.

As described above, in some embodiments, the vaccine comprises a polypeptide or a dimeric protein, and accordingly, in an eighth aspect the invention relates to a method for preparing a dimeric protein or an polypeptide as defined above, wherein the method comprises
 a) transfecting the polynucleotide as defined above into a cell population;
 b) culturing the cell population;
 c) collecting and purifying the dimeric protein, or the polypeptide expressed from the cell population.

In other embodiments, the vaccine comprises a polynucleotide, and accordingly, in a ninth aspect the invention relates to a method for preparing a vaccine, such as a DNA or RNA vaccine, comprising an immunologically effective amount of a polynucleotide, wherein said method comprises
 a. preparing a polynucleotide as defined above;
 b. mixing the polynucleotide obtained under step a) in a pharmaceutically acceptable carrier, diluent, or buffer, thereby obtaining the vaccine.

In a tenth aspect the invention relates to a method of treating cancer in a patient, the method comprising administering to the patient in need thereof, a vaccine as defined above. In an alternative tenth aspect, the invention relates to a vaccine as defined above for use in a method of treating cancer.

DESCRIPTION OF DRAWINGS

FIG. 2 upper left panels shows Western blots of VB10.NEO CT26-X (VB4001) and VB10.NEO B16-X (VB4003) comprising 10 neoepitopes and FIG. 2 lower left panels shows Western blots of VB10.NEO CT26-III (VB4002) and VB10.NEO B16-III (VB4004) comprising 3 neoepitopes. The formation of functional homodimers are shown in the left panels of the western blots for each construct (−reducing agent). The right panels illustrate the monomers (+reducing agent). FIG. 2 right panels shows results from two ELISA experiments detecting vaccibody proteins in the supernatant from HEK293 cells transfected with the VB10.NEO constructs. Upper right panel shows the expression level of the VB10.NEO CT26 constructs, VB4001 and VB4002, and lower right panel shows the expression level of the VB10.NEO B16 constructs, VB4003 and VB4004

VB10.NEO B16-X=VB4003=B16 pepM1-M10, 5 aa linker

VB10.NEO B16-X=VB4011=B16 pepM1-M10, 10 aa linker.

Figure 7:
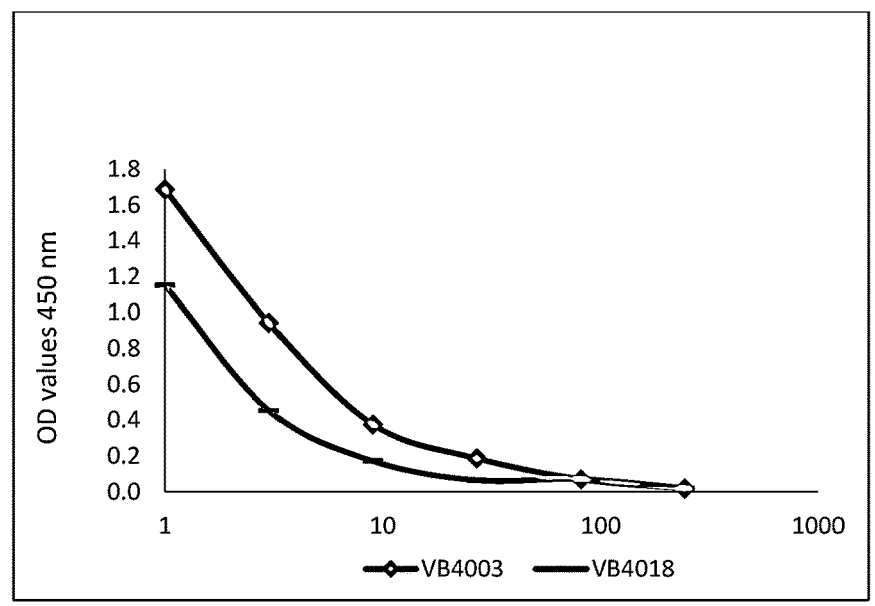
Figure 7:
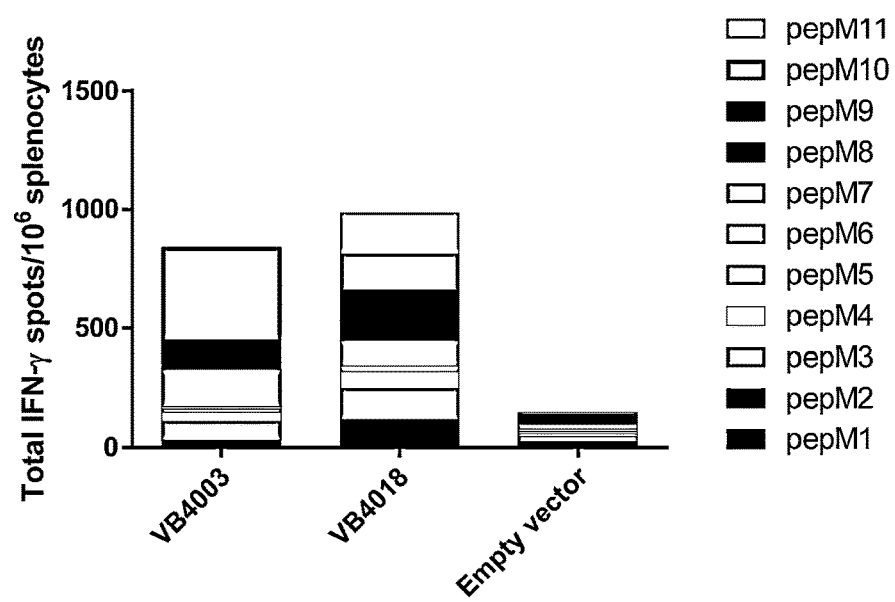

FIG. 7. Vaccibody DNA vaccine comprising 2×10 neoepitopes (VB4018) induces a broader immune response against individual neoepitopes compared to vaccibody DNA vaccine comprising 1×10 neoepitopes (VB4003). Upper panel: Comparison of vaccibody expression levels of VB10.NEO B16-X (VB4003) and VB10.NEO B16-XX (VB4018) in the supernatant of HEK293 cells transfected with the corresponding vaccibody DNA constructs, detected by sandwich ELISA. Lower panel: Histogram showing the IFN-γ immune response towards neoepitopes from the B16 melanoma model in mice injected with VB4003 or VB4018. The benefit of including 2 copies of each neoepitope is limited on the total immune response, however, a broader immune response is observed towards individual neoepitopes. Empty vector is included as a negative control.

VB10.NEO B16-X=VB4003=B16 pepM1-M10, 5 aa linker

VB10.NEO B16-XX=VB4018=B16 pepM1-M4+M11+M6-M10×2, 5 aa linker

Figure 8:
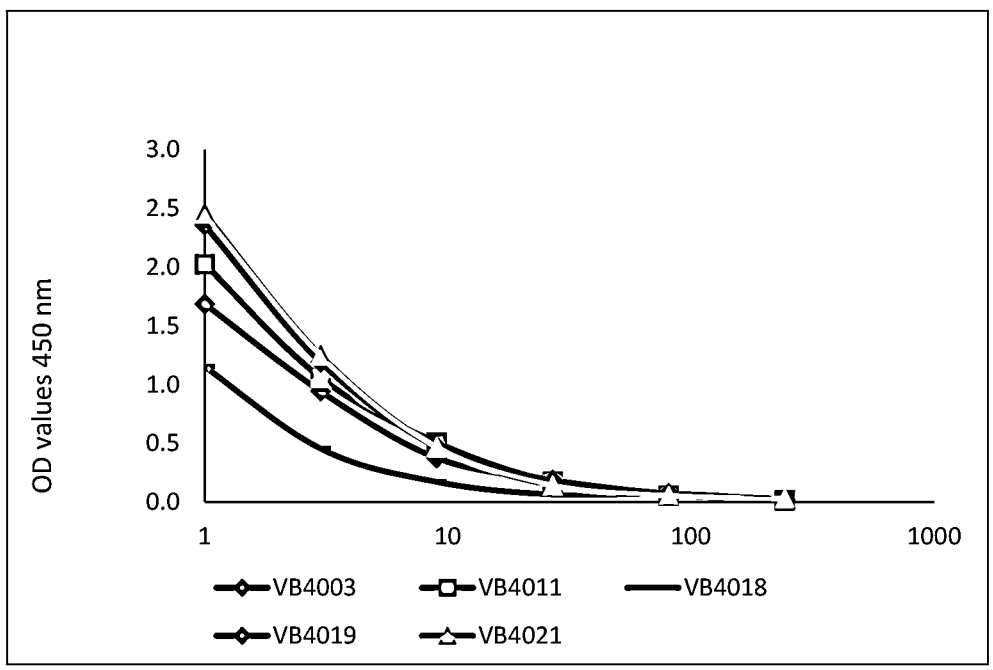
Figure 8:
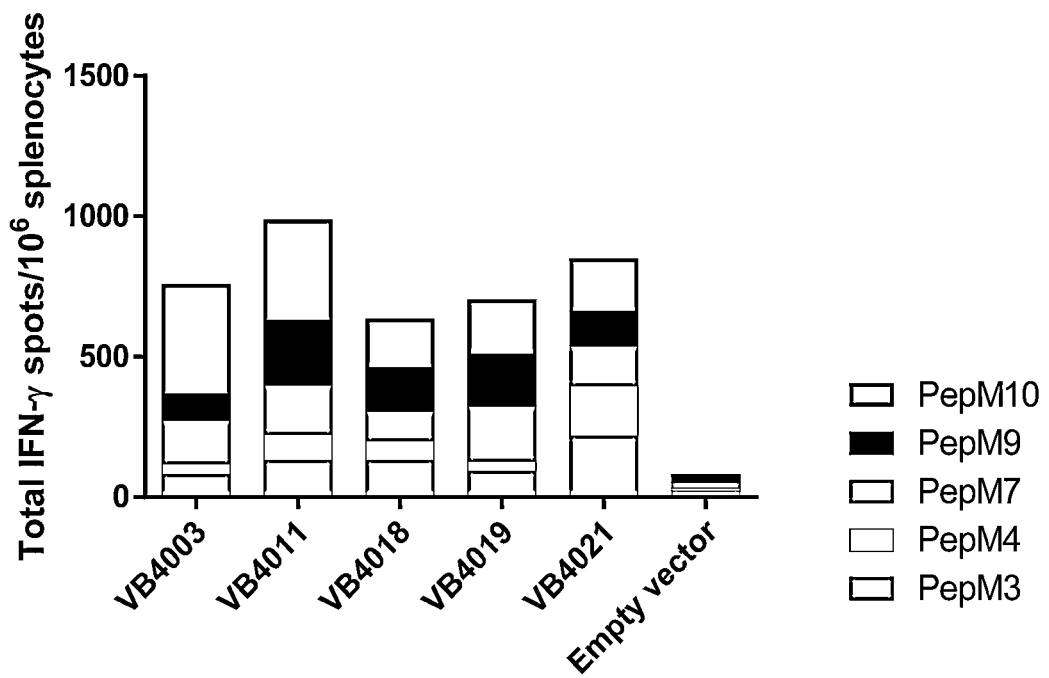

FIG. 8. Several copies of each neoeptiope in a vaccibody construct gives a more uniform immune response against the 5 selected best neoepitopes. Upper panel: Comparison of vaccibody expression level of VB10.NEO B16-X (VB4003 and VB4011), VB10.NEO B16-XX (VB4018), VB10.NEO B16-V×2 (VB4019) and VB10.NEO B16-V×4 in the supernatant of HEK293 cells transfected with the corresponding vaccibody DNA constructs, detected by sandwich ELISA. Lower panel: Histogram showing the IFN-γ immune responses towards 5 neoepitopes from the B16 melanoma model (PepM3, PepM4, PepM7, PepM9 and PepM10) in mice injected with 5 different vaccibody DNA vaccines that all include these 5 neoepitopes, but in different context. Empty vector is included as a negative control. The figure illustrates that several copies of each neoepitope as observed with the vaccibody constructs VB4019 (V×2) and VB4021 (V×4) mediate a more evenly immune response towards the 5 shared neoepitopes compared to the decatope VB4003, where the 5 selected neoepitopes are presented once. However, the construct holding 10 different neoepitopes (i.e. just a single copy of the 5 neoepitopes tested in this assay), thus, importantly with an increased length of the linker (10 amino acids, VB4011) induced the strongest total immune response towards the 5 shared neoepitopes.

VB10.NEO B16-X=VB4003=B16 pepM1-M10, 5 aa linker

VB10.NEO B16-X=VB4011=B16 pepM1-M10, 10 aa linker

VB10.NEO B16-XX=VB4018=B16 pepM1-M4+M11+M6-M10×2, 5 aa linker

VB10.NEO B16-V×2=VB4019=B16 pepM3+M4+M7+M9+M10×2, 5 aa linker

VB10.NEO B16-V×4=VB4021=B16 pepM3+M4+M7+M9+M10×4, 5 aa linker

Figure 9:
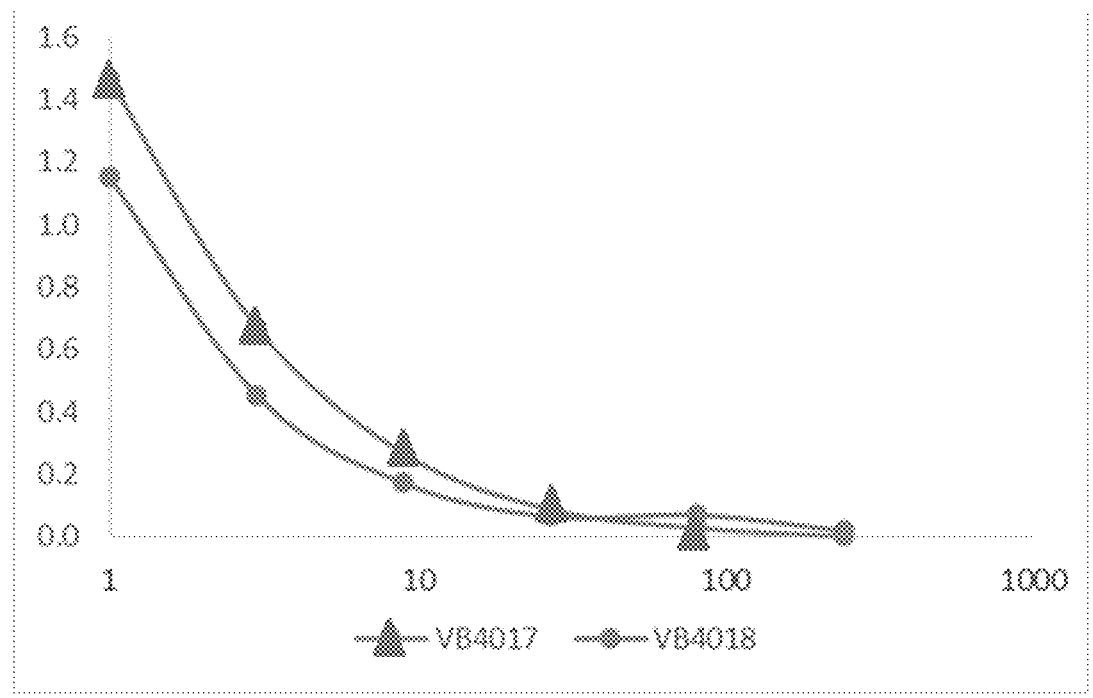

FIG. 9 illustrates that vaccibodiy VB4018 comprising 20 neoepitopes are expressed to the same level as vaccibody VB4017 comprising 10 neoepitopes. The vaccibody proteins are detected in the supernatant of HEK293 cells transfected with the different Vaccibody DNA constructs by sandwich ELISA.

VB10.NEO B16-X=VB4017=B16 pepM1-M4+M11+M6-M10, 5 aa linker

VB10.NEO B16-XX=VB4018=B16 pepM1-M4+M11+M6-M10×2, 5 aa linker

Figure 10:
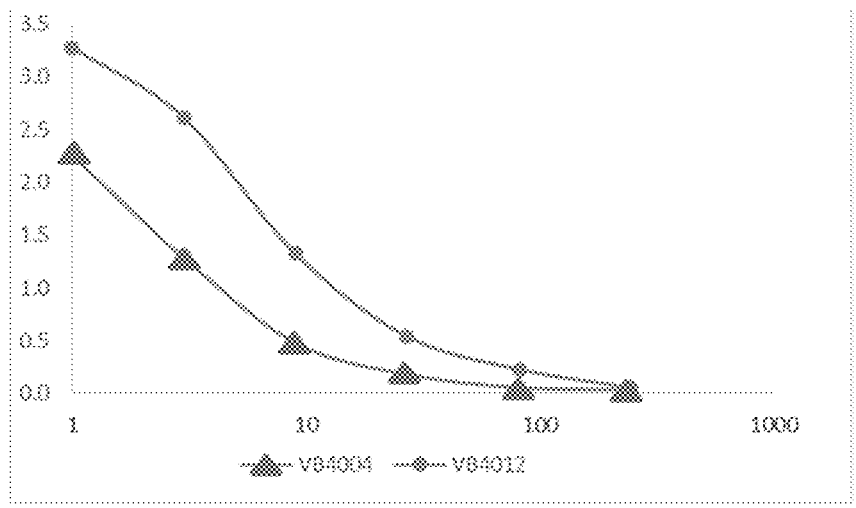
Figure 10:
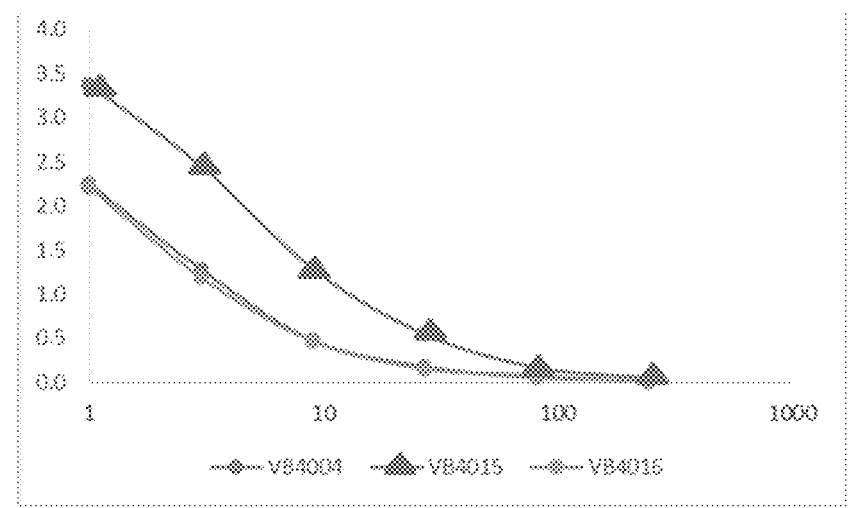

FIG. 10. Expression levels of different vaccibody constructs comprising 3-neoepitopes are compared. The vaccibody proteins are detected in the supernatant of HEK293 cells transfected with the different Vaccibody DNA constructs by sandwich ELISA Upper panel: Improved expression and secretion of functional vaccibody proteins are observed when the 3 neoepitopes are spaced with an 10 aa linker (VB4012) compared to a 5 aa linker (VB4004). Lower panel: The figure illustrates that changing the order of the neoepitopes may affect expression of the vaccibodies.

VB10.NEO B16-III=VB4004=B16 pepM1-M3, 5 aa linker

VB10.NEO B16-III=VB4012=B16 pepM1-M3, 10 aa linker

VB10.NEO B16-III=VB4015=B16 pepM1+M8+M3, 5 aa linker

VB10.NEO B16-III=VB4016=B16 pepM1+M3+M2, 5 aa linker

Figure 11:
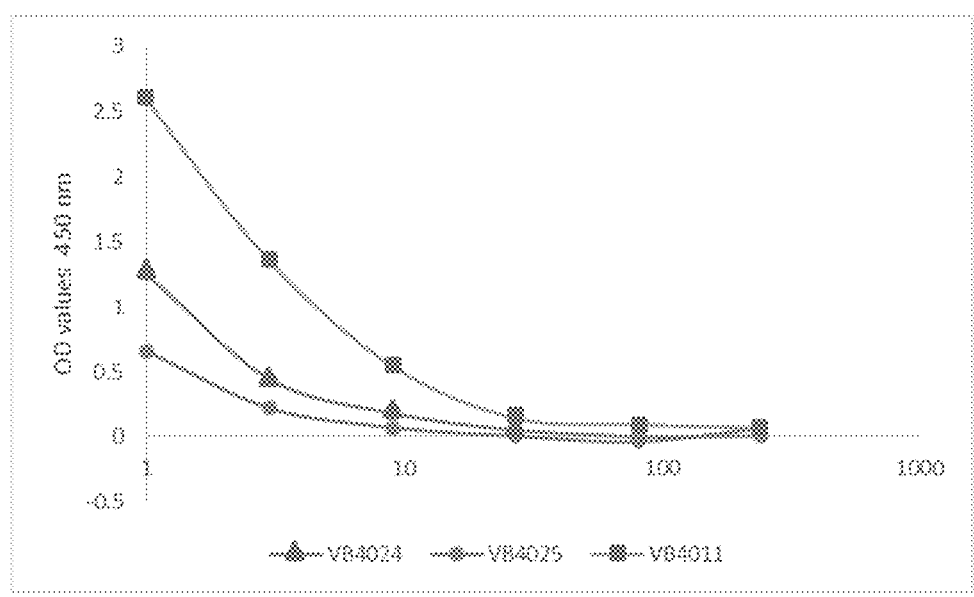
Figure 11:
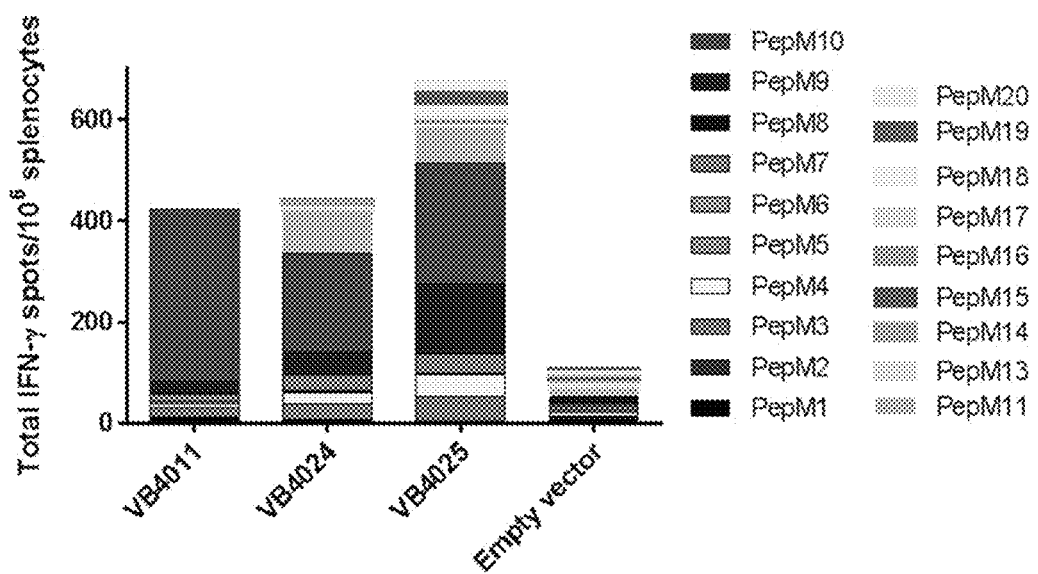

FIG. 11 illustrates immune responses in B16 melanoma mice that are induced after a single injection with vaccibody DNA vaccines comprising either 10 neoepitopes (VB4011), 15 neoepitopes (VB4024) or 20 neoepitopes (VB4025). Upper panel: Expression levels of the tested vaccibody constructs comprising 10-, 15- or 20 neoepitopes. The vaccibody proteins are detected in the supernatant of HEK293 cells transfected with the different Vaccibody DNA constructs by sandwich ELISA. Lower panel: Total immune response against neoepitopes in mice injected with the DNA vaccine candidates VB10.NEO B16-XV comprising 15 neoepitopes (VB4024) or VB10.NEO B16-XX comprising 20 neoepitopes (VB4025) compared to the VB10.NEO B16-X comprising 10 neoepitopes (VB4011). The figure shows the total number of IFNγ-spots per $10^6$ splenocytes. As a negative control, mice were injected with empty vector not comprising the neoepitopes. The figure illustrates that vaccibody DNA vaccines comprising 20 neoepitopes induces a stronger and broader total immune response than vaccibody DNA vaccines comprising only 10 neoepitopes.

Figure 12:
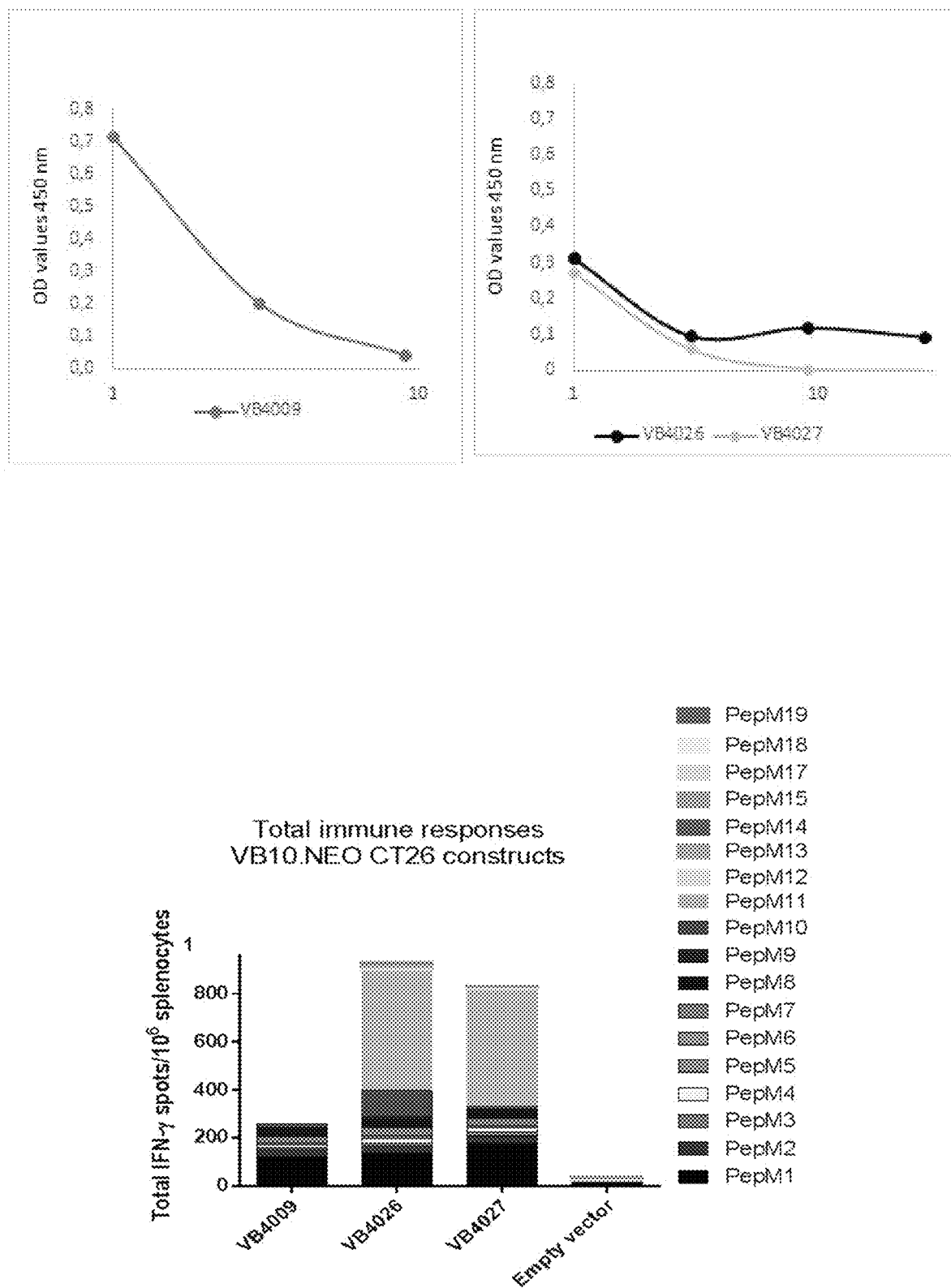

FIG. 12 illustrates immune responses in CT26 colon carcinoma mice that are induced after a single injection with vaccibody DNA vaccines comprising either 10 neoepitopes (VB4009), 15 neoepitopes (VB4026) or 20 neoepitopes (VB4027). Upper panel: Expression levels of the tested vaccibody construct VB10.NEO CT26-X comprising 10 neoepitopes (left panel) and vaccibody constructs VB10.NEO CT26-XV and XX comprising 15 and 20 neoepitopes, respectively (right panel). Lower panel: Total immune response towards neoepitopes in the CT26 colon carcinoma model in mice injected with the DNA vaccine candidates VB10.NEO CT26-XV comprising 15 neoepitopes (VB4026) or VB10.NEO CT26-XX comprising 20 neoepitopes (VB4027) compared to the VB10.NEO CT26-X comprising 10 neoepitopes (VB4009). The figure shows the total number of IFNγ-spots per $10^6$ splenocytes. As a negative control, mice were injected with empty vector not comprising the neoepitopes. The figure illustrates that vaccibody DNA vaccines comprising 20 or 15 neoepitopes induces a stronger and broader total immune response than vaccibody DNA vaccines comprising only 10 neoepitopes.

NEO CT26-X=VB4009=CT26 pepM1-M10, 10 aa linker

NEO CT26-XV=VB4026=CT26 pepM1-M15, 10 aa linker

NEO CT26-XX=VB4027=CT26 pepM1-M20, 10 aa linker

Figure 13:
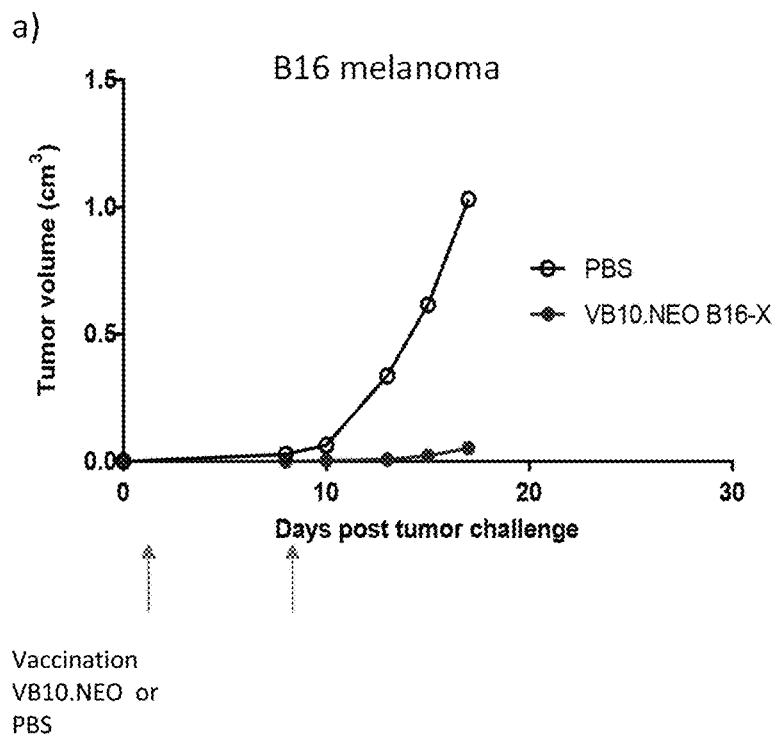
Figure 13:
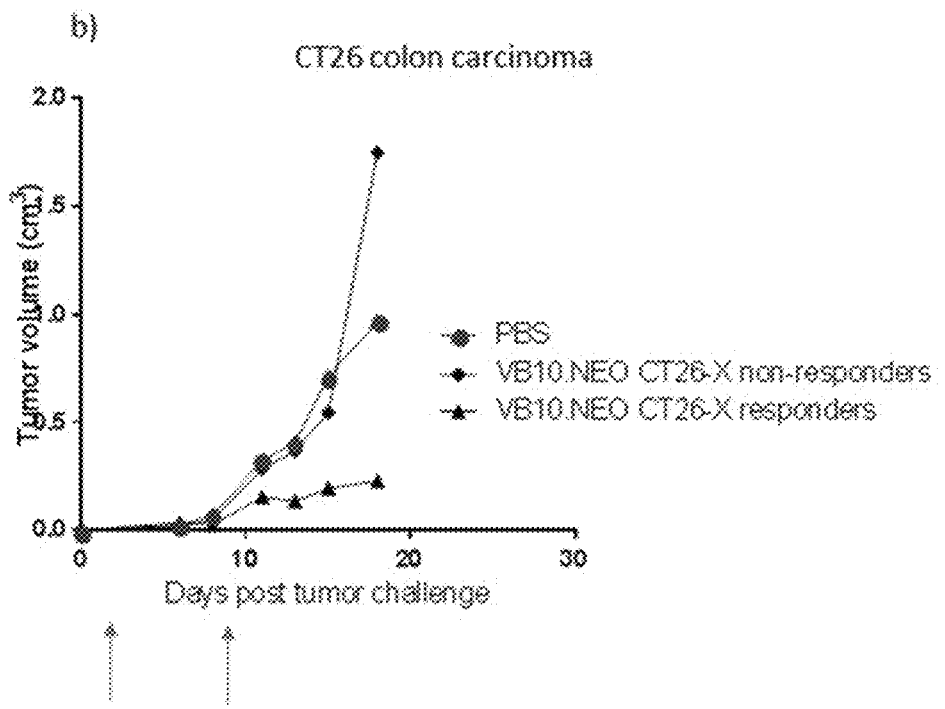

FIG. 13 illustrates that mice immunized twice with VB10.NEO vaccine candidates comprising 10 neoepitopes are able to significantly delay and reduce tumour growth in the a) B16 melanoma model and b) the CT26 colon carcinoma model compared to negative control mice receiving PBS only. The figure shows the tumour volume development over time. In the CT26 colon carcinoma experiment, mice were divided into responders that were able to stabilize tumour growth and non-responders.

DEFINITIONS

Tumor is used in the present context for both a solid tumor as well as for tumor cells found in a bodily fluid, such as blood.

Tumor neoantigen is used for any tumor specific antigen comprising one or more mutations as compared to the host's exome and is used synonymously with the term cancer neoantigen.

Tumor neoepitope is used for any immunogenic mutation in a tumor antigen and is used synonymously with the term cancer neoepitope.

Tumor neoepitope sequence is used to describe the sequence comprising the neoepitope in an antigenic subunit, and is used synonymously with the term cancer neoepitope sequence.

Therapeutic anticancer vaccine is used to describe that the vaccine is used for reducing or destroying tumor cells already present in the patient.

DETAILED DESCRIPTION OF THE INVENTION

Cancers develop from the patient's normal tissue by one or a few cells starting an abnormal uncontrolled proliferation of the cells due to mutations. Although the cancer cells are mutated, most of the genome is intact and identical to the remaining cells in the patient. This is also the explanation of some of the failures in prior attempts to develop an anti-cancer vaccine, namely that the vaccine to some extent is also directed to the normal cells in the patient. As discussed above, the approach of attacking a tumor as defined by the present invention is to use the knowledge that any tumor, due to the mutations, expresses mutated proteins, so-called neoantigens that are not identical to any proteins in the normal cells of the patient, and therefore the neoantigens are efficient targets for a therapeutic anticancer vaccine. The mutations found in a tumor are normally highly individual, and accordingly, the vaccine according to the present invention is personalized for use only in the patient having the mutation in question.

The vaccines according to the present invention use the normal adaptive immune system to provide immunity against the tumor cells. The adaptive immune system is specific in that every foreign antigen evokes an immune response specifically towards said foreign antigen by the recognition of specific "non-self" antigens during a process called antigen presentation. The cells of the adaptive immune system are lymphocytes, in particularly B cells and T cells. B cells are involved in the humoral immune response, whereas T cells are involved in cell-mediated immune response.

In particularly, the vaccine according to the present invention is designed for evoking a cell-mediated immune response through activation of T cells against the neoantigens. T cells recognize neoepitopes when they have been processed and presented complexed to a MHC molecule as discussed below.

Major Histocompatibility Complex (MHC)

The neoepitopes according to the present invention are designed to be presented in MHC-neoepitope complexes. There are two primary classes of major histocompatibility complex (MHC) molecules, MHC I and MHC II.

MHC I is found on the cell surface of all nucleated cells in the body. One function of MHC I is to display peptides of non-self proteins from within the cell to cytotoxic T cells. The MHC I complex-peptide complex is inserted into the plasma membrane of the cell presenting the peptide to the cytotoxic T cells, whereby an activation of cytotoxic T cells against the particular MHC-peptide complex is triggered. The peptide is positioned in a groove in the MHC I molecule, allowing the peptide to be about 8-10 amino acids long.

MHC II molecules are a family of molecules normally found only on antigen-presenting cells such as dendritic cells, mononuclear phagocytes, some endothelial cells, thymic epithelial cells, and B cells.

As opposed to MHC I, the antigens presented by class II peptides are derived from extracellular proteins. Extracellular proteins are endocytosed, digested in lysosomes, and the resulting antigenic peptides are loaded onto MHC class II molecules and then presented at the cell surface. The antigen-binding groove of MHC class II molecules is open at both ends and is able to present longer peptides, generally between 15 and 24 amino acid residues long.

Class I MHC molecules are recognized by CD8 and co-receptors on the T cells, normally called CD8+ cells, whereas class II MHC molecules are recognized by CD4 and co-receptors on the T cells, normally called CD4+ cells.

Vaccines

The neoantigen vaccines of the present invention comprise a polynucleotide encoding a polypeptide comprising three units, i.e. a targeting unit, a dimerization unit and an antigenic unit. Due to the dimerization unit the polypeptide forms a dimeric protein called a vaccibody.

The genes encoding the three units are genetically engineered to be expressed as one gene. When expressed in vivo, the polypeptides/dimeric proteins target antigen presenting cells (APCs), which results in enhanced vaccine potency compared to identical non-targeted antigens.

The present invention relates to vaccines where the antigenic unit comprises antigenic subunits, wherein each subunit comprises a cancer neoepitope sequence or at least a part of a cancer neoepitope sequence. The neoepitope sequence is obtained by sequencing tumor DNA or RNA and identifying tumor specific mutations representing neoantigens. Thereby, a personalized neoantigen vaccine is obtained that specifically targets the identified tumor antigens.

One aspect of the present invention relates to a therapeutic anticancer neoepitope vaccine comprising an immunologically effective amount of
a polynucleotide comprising a nucleotide sequence encoding
a targeting unit
a dimerization unit
a first linker
an antigenic unit, wherein said antigenic unit comprises n−1 antigenic subunits, each subunit comprising at least a part of a cancer neoepitope sequence and a second linker and said antigenic unit further comprising a final cancer neoepitope sequence, wherein n is an integer of from 3 to 50.

or a polypeptide encoded by the polynucleotide as defined in 1), or a dimeric protein consisting of two polypeptides encoded by the polynucleotide as defined in 1).

Thus, the vaccine comprises n neoepitopes or neoepitope sequences and n–1 second linkers, wherein n is an integer from 3 to 50.

Antigenic Unit

The antigenic unit according to the invention comprises a plurality of tumor neoepitopes, wherein each neoepitope corresponds to a mutation identified in a tumor neoantigen. The mutation may be any mutation leading to a change in at least one amino acid. Accordingly, the mutation may be one of the following:

a non-synonymous mutation leading to a change in the amino acid a mutation leading to a frame shift and thereby a completely different open reading frame in the direction after the mutation a read-through mutation in which a stop codon is modified or deleted leading to a longer protein with a tumor-specific neoepitope splice mutations that lead to a unique tumor-specific protein sequence chromosomal rearrangements that give rise to a chimeric protein with a tumor-specific neoepitope at the junction of the two proteins In the antigenic unit, all but the last of the tumor neoepitopes are arranged in antigenic subunits, wherein each subunit consists of a tumor neoepitope sequence and a second linker, whereas the last subunit comprises a neoepitope only, i.e. no such second linker. Due to the separation of the tumor neoepitope sequences by said second linker, each neoepitope is presented in an optimal way to the immune system, whereby the efficiency of the vaccine is ensured as discussed below.

The cancer neoepitope sequence preferably has a length suitable for presentation by the MHC molecules discussed above. Thus, in a preferred embodiment the cancer neoepitope is from 7 to 30 amino acids long. More preferred are cancer neoepitope sequences having a length of from 7 to 10 amino acids or cancer neoepitope sequences having a length of from 13 to 30 amino acids.

In order to avoid that tumors escape the immune system by shutting down expression of a mutated gene if the vaccine is directed towards the expression product of said gene, it is preferred to include a plurality of different neoepitopes into the antigenic unit. In general the more genes the tumor has to shut down the less likely is it that the tumor is capable of shutting down all of them and still be able to proliferate or even survive. Furthermore, the tumor may be heterogeneous in that not each and every neoantigen is expressed by all the tumor cells. Accordingly, in accordance with the present invention, the approach is to include as many neoepitopes as possible into the vaccine in order to attack the tumor efficiently. Also, in order to secure that all neoepitopes are loaded efficiently to the same antigen presenting cell they are arranged as one amino acid chain instead of as discrete peptides. However, as described above, the object of the vaccine is to activate the T cells against the neoepitopes, and the T cells may be diluted in case too many neoepitopes are included into the vaccine, and therefore it is a balance to provide the vaccine with an optimal number of neoepitopes in the antigenic unit.

As discussed below in more details, the tumor exome is analysed to identify neoantigens and subsequently the most antigenic neoepitopes are selected. The present inventor has found that at least 3 neoepitopes should be selected to be incorporated into the vaccine, such as at least 5 neoepitopes, such as at least 7 neoepitopes, such as at least 10 neoepitopes, in order to efficiently be able to "hit" substantially all tumor cells.

Figure 4:
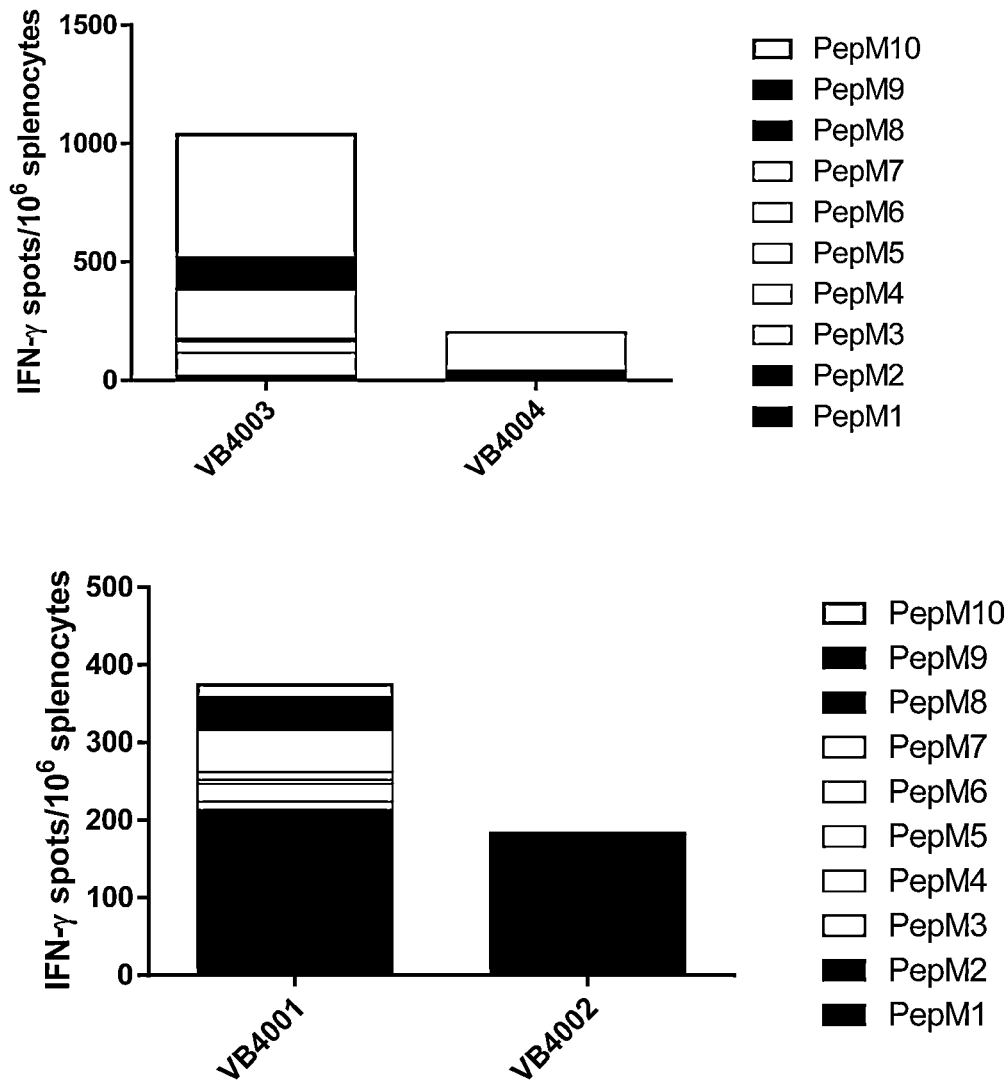
FIG. 4 illustrates that vaccibody DNA vaccines comprising 10 neoepitopes induces a stronger and broader total immune response than vaccibody DNA vaccines comprising only 3 neoepitopes. Upper panel: Comparison of the immune responses towards neoepitopes in the B16 melanoma model when injecting with VB10.NEO B16-X comprising 10 neoepitopes (VB4003) and VB10.NEO B16-III comprising 3 neoepitopes (VB4004), respectively. Lower panel: Comparison of the immune responses towards neoepitopes in the CT26 colon carcinoma model when injecting VB10.NEO CT26-X comprising 10 neoepitopes (VB4001) and VB10.NEO CT26-III comprising 3 neoepitopes (VB4002), respectively.
 VB10.NEO CT26-X=VB4001=CT26 pepM1-M10,
 VB10.NEO CT26-III=VB4002=CT26 pepM1-M3,
 VB10.NEO B16-X=VB4003=B16 pepM1-M10,
 VB10.NEO B16-III=VB4004=B16 pepM1-M3.

In addition, the inventors of the present invention have found that increasing the numbers of neoepitopes in the vaccine constructs from 3 neoepitopes to 10 neoepitopes leads to a surprising increase in the immune response (see FIG. 4). In addition, it has been found that increasing the number of neoepitopes in the vaccine constructs from 10 neoepitopes to 15 or 20 neoepitopes leads to a further increase in the immune response (see FIGS. 11 and 12).

Thus, in a preferred embodiment the vaccine according to the present invention comprises at least 10 neoepitopes. In another preferred embodiment the vaccine according to the present invention comprises at least 15 neoepitopes, such as at least 20 neoepitopes.

In one embodiment from 3 to 50 neoepitopes are included in the vaccine in order to obtain the most efficient immune response without diluting the T cells, such as from 3 to 30 neoepitopes, such as from 3 to 20 neoepitopes, such as from 3 to 15 neoepitopes, such as from 3 to 10 neoepitopes, and consequently n is preferably an integer of from 3 to 50, such as from 3 to 30, such as from 5 to 25, such as from 3 to 20, such as from 3 to 15, such as from 3 to 10.

In another embodiment 5 to 50 neoepitopes may be included in the vaccine in order to obtain the most efficient immune response without diluting the T cells, such as from 5 to 30 neoepitopes, such as for example from 5 to 25 neoepitopes, such as from 5 to 20 neoepitopes, such as from 5 to 15 neoepitopes, such as from 5 to 10 neoepitopes, and consequently n is preferably an integer of from 5 to 50, such as from 5 to 30, such as from 5 to 25, such as from 5 to 20, such as from 5 to 15, such as from 5 to 10.

In a further embodiment 10 to 50 neoepitopes may be included in the vaccine in order to obtain the most efficient immune response without diluting the T cells, such as from 10 to 40 neoepitopes, such as from 10 to 30 neoepitopes, such as from 10 to 25 neoepitopes, such as from 10 to 20 neoepitopes, such as from 10 to 15 neoepitopes, and consequently n is preferably an integer of from 10 to 50, such as from 10 to 30, such as from 10 to 20, such as from 10 to 15 neoepitopes.

The inventors of the present invention have shown that vaccibody DNA vaccines comprising 10 neoepitopes induces a stronger and broader total immune response than vaccibody DNA vaccines comprising only 3 neoepitopes (see FIG. 4 and Example 2). Further, increasing the number of neoepitopes to more than 20 may result in a less efficient vaccine due to a dilution of the T cells. Further, it can be associated with technical difficulties to include more than 20 neoepitopes.

Accordingly, in a preferred embodiment of the present invention the vaccine comprises from 10 to 20 neoepitopes.

In yet another embodiment 15 to 50 neoepitopes are included in the vaccine in order to obtain the most efficient immune response without diluting the T cells, such as from 15 to 30 neoepitopes or such as from 15 to 20 neoepitopes and consequently n is preferably an integer of from 15 to 50, such as from 15 to 30 or such as from 15 to 20 neoepitopes.

In one embodiment, the antigenic unit comprises one copy of each cancer neoepitope, so that when 10 neoepitopes are included in the vaccine a cell-mediated immune response against 10 different neoepitopes can be evoked.

If however only a few relevant antigenic mutations are identified, then the antigenic unit may comprise at least two copies of at least one neoepitope in order to strengthen the immune response to these neoepitopes. Also for manufacturing and regulatory reasons it may be an advantage to keep the length of plasmid and i.e. the antigenic unit constant, and therefore it may be advantageously to include more than one copy of the same neoepitope in the antigenic unit.

As discussed above, it may be an advantage to keep the length of the antigenic unit constant, and therefore it is preferred in one embodiment that all the cancer neoepitope sequences have identical length. However, if one or more of the neoepitopes result from a mutation leading to a frame shift or stop codon mutation, the neoepitope may have a substantial length, such as consisting of at least the mutated part of the protein, the most antigenic portion of the mutated protein or maybe of the whole mutated protein, whereby the length of at least one of the neoepitopes is substantially longer than the neoepitopes arising from a non-synonymous point mutation.

The length of the antigenic unit is primarily determined by the length of the neoepitopes and the number of neoepitopes arranged in the antigenic unit and is from about 21 to 1500, preferably from about 30 amino acids to about a 1000 amino acids, more preferably from about 50 to about 500 amino acids, such as from about 100 to about 400 amino acids, from about 100 to about 300 amino acids.

In particularly when the neoepitope is short, such as a few amino acids long, the cancer neoepitope sequence comprises the neoepitope flanked at both sides by an amino acid sequence. Preferably, the neoepitope is positioned essentially in the middle of a cancer neoepitope sequence, in order to ensure that the neoepitope is presented by the antigen presenting cells after processing. The amino acid sequences flanking the neoepitope are preferably the amino acid sequences flanking the neoepitope in the neoantigen, whereby the cancer neoepitope sequence is a true subsequence of the cancer neoantigen amino acid sequence.

Although it is possible to obtain a relevant immune response towards the tumor if the neoepitopes are randomly arranged in the antigenic subunit, it is preferred to follow at least one of the following methods for ordering the neoepitopes in the antigenic unit in order to enhance the immune response.

In one embodiment, depending on the selected neoepitopes, the antigenic subunits are arranged in the order of more antigenic to less antigenic in the direction from the first linker towards the final neoepitope.

In another embodiment, in particularly if the hydrophilicity/hydrophobicity varies greatly among the neoepitopes, it is preferred that the most hydrophobic antigenic subunit(s) is/are substantially positioned in the middle of the antigenic unit and the most hydrophilic antigenic subunit(s) is/are positioned at the beginning and/or end of the antigenic unit. Alternatively, the neoepitopes may be arranged alternating between a hydrophilic and a hydrophobic neoepitope.

Furthermore, GC rich neoepitopes should be spaced so that GC clusters are avoided, preferably GC rich neoepitopes are spaced by at least one subunit.

The second linker is designed to be non-immunogenic and is preferably also a flexible linker, whereby the tumor neoepitopes, in spite of the high numbers of antigenic subunits present in the antigenic unit, are presented in an optimal manner to the T cells. Preferably, the length of the second linker is from 4 to 20 amino acids to secure the flexibility. In another preferred embodiment, the length of the second linker is from 8 to 20 amino acids, such as from 8 to 15 amino acids, for example 8 to 12 amino acids or such as for example from 10 to 15 amino acids. In a particular embodiment, the length of the second linker is 10 amino acids.

In a specific embodiment, the vaccine of the present invention comprises 10 neoepitopes, wherein the second linkers have a length of from 8 to 20 amino acids, such as from 8 to 15 amino acids, for example 8 to 12 amino acids or such as for example from 10 to 15 amino acids. In a particular embodiment, the vaccine of the present invention comprises 10 neoepitopes and wherein the second linkers have a length of 10 amino acids.

The second linker is preferably identical in all antigenic subunits. If, however, one or more of the neoepitopes comprise an amino acid motif similar to the linker, it may be an advantage to substitute the neighbouring second linkers with a second linker of a different sequence. Also, if a neoepitope-second linker junction is predicted to constitute an epitope in itself, then a second linker of a different sequence might be used.

The second linker is preferably a serine-glycine linker, such as a flexible GGGGS linker, such as GGGSS, GGGSG, GGGGS or multiple variants thereof such as GGGGSGGGGS or (GGGGS)$_m$, (GGGSS)$_m$, (GGGSG)$_m$, where m is an integer from 1 to 5, from 1 to 4 or from 1 to 3. In a preferred embodiment m is 2.

In a preferred embodiment the serine-glycine linker further comprises at least one leucine (L), such as at least 2 or at least 3 leucines. The serine-glycine linker may for example comprise 1, 2, 3 or 4 leucine. Preferably, the serine-glycine linker comprises 1 leucine or 2 leucines.

In one embodiment the second linker comprises or consists of the sequence LGGGS, GLGGS, GGLGS, GGGLS or GGGGL. In another embodiment the second linker comprises or consists of the sequence LGGSG, GLGSG, GGLSG, GGGLG or GGGSL. In yet another embodiment the second linker comprises or consists of the sequence LGGSS, GLGSS, GGLSS, GGGLS or GGGSL.

In yet another embodiment the second linker comprises or consists of the sequence LGLGS, GLGLS, GLLGS, LGGLS or GLGGL. In another embodiment the second linker comprises or consists of the sequence LGLSG, GLLSG, GGLSL, GGLLG or GLGSL. In yet another embodiment the second linker comprises or consists of the sequence LGLSS, GLGLS, GGLLS, GLGSL or GLGSL.

In another embodiment of the present invention the second serine-glycine linker has a length of 10 amino acids and comprises 1 leucine or 2 leucines.

In one embodiment the second linker comprises or consists of the sequence LGGGSGGGGS, GLGGSGGGGS, GGLGSGGGGS, GGGLSGGGGS or GGGGLGGGGS. In another embodiment the second linker comprises or consists of the sequence LGGSG GGGSG, GLGSGGGGSG, GGLSGGGGSG, GGGLGGGGSG or GGGSLGGGSG. In yet another embodiment the second linker comprises or consists of the sequence LGGSSGGGSS, GLGSSGGGSS, GGLSSGGGSS, GGGLSGGGSS or GGGSLGGGSS.

In a further embodiment the second linker comprises or consists of the sequence LGGGSLGGGS, GLGGSGLGGS, GGLGSGGLGS, GGGLSGGGLS or GGGGLGGGGL. In another embodiment the second linker comprises or consists of the sequence LGGSGLGGSG, GLGSGLGSG, GGLSGGGLSG, GGGLGGGGLG or GGGSLGGGSL. In yet another embodiment the second linker comprises or consists of the sequence LGGSSLGGSS, GLGSSGLGSS, GGLSSGGLSS, GGGLSGGGLS or GGGSLGGGSL.

In a preferred embodiment the vaccine according to the present invention comprises at least 10 neoepitopes that are separated by 10 amino acid linkers. In another preferred embodiment the vaccine according to the present invention comprises at least 15 neoepitopes that are separated by 10 amino acid linkers, such as at least 20 neoepitopes that are separated by 10 amino acid linkers.

In another preferred embodiment the vaccine comprises from 10 to 20 or from 10 to 25 neoepitopes that are separated by second linkers. Preferably, said second linkers are 10 amino acids. The second linker may also have any length as defined herein above, such as for example from 8 to 12 amino acids.

Alternative linkers may be selected from the group consisting of GSAT linkers and SEG linkers, or multiple variants thereof.

Targeting Unit

Due to the targeting unit, the polypeptide/dimeric protein of the invention leads to attraction of dendritic cells (DCs), neutrophils and other immune cells. Thus, the polypeptide/dimeric protein comprising the targeting module will not only target the antigens to specific cells, but in addition facilitate a response-amplifying effect (adjuvant effect) by recruiting specific immune cells to the administration site of the vaccine. This unique mechanism is of great importance in a clinical setting where patients can receive the vaccine without any additional adjuvants since the vaccine itself gives the adjuvant effect.

The term "targeting unit" as used herein refers to a unit that delivers the polypeptide/protein with its antigen to an antigen presenting cell for MHC class II-restricted presentation to CD4+ T cells or for providing cross presentation to CD8+ T cells by MHC class I restriction.

The targeting unit is connected through the dimerization unit to the antigenic unit, wherein the latter is in either the COOH-terminal or the NH2-terminal end of the polypeptide/dimeric protein. It is preferred that the antigenic unit is in the COOH-terminal end of the polypeptide/dimeric protein.

The targeting unit is designed to target the polypeptide/dimeric protein of the invention to surface molecules expressed on the relevant antigen presenting cells, such as molecules expressed exclusively on subsets of dendritic cells (DC).

Examples of such target surface molecules on APC are human leukocyte antigen (HLA), cluster of differentiation 14 (CD14), cluster of differentiation 40 (CD40), chemokine receptors and Toll-like receptors (TLRs). HLA is a major histocompatibility complex (MHC) in humans. The Toll-like receptors may for example include TLR-2, TLR-4 and/or TLR-5.

The polypeptide/dimeric protein of the invention can be targeted to said surface molecules by means of targeting units comprising for example antibody binding regions with specificity for CD14, CD40, or Toll-like receptor; ligands, e.g. soluble CD40 ligand; natural ligands like chemokines, e.g. RANTES or MIP-1a; or bacterial antigens like for example flagellin.

In one embodiment the targeting unit has affinity for an MHC class II protein. Thus, in one embodiment the nucleotide sequence encoding the targeting unit encodes the antibody variable domains (VL and VH) with specificity for MHC class II proteins, selected from the group consisting of anti-HLA-DP, anti-HLA-DR and anti-HLA-II.

In another embodiment the targeting unit has affinity for a surface molecule selected from the group consisting of CD40, TLR-2, TLR-4 and TLR-5. Thus, in one embodiment the nucleotide sequence encoding the targeting unit encodes the antibody variable domains (VL and VH) with specificity for anti-CD40, anti-TLR-2, anti-TLR-4 and anti-TLR-5. In one embodiment the nucleotide sequence encoding the targeting unit encodes Flagellin. Flagellin has affinity for TLR-5.

Preferably, the targeting unit has affinity for a chemokine receptor selected from CCR1, CCR3 and CCR5. More preferably, the nucleotide sequence encoding the targeting unit encodes the chemokine hMIP-1alpha (LD78beta), which binds to its cognate receptors, CCR1, CCR3 and CCR5 expressed on the cell surface of APCs.

The binding of the polypeptide/dimeric protein of the invention to its cognate receptors leads to internalization in the APC and degradation of the proteins into small peptides that are loaded onto MHC molecules and presented to CD4+ and CD8+ T cells to induce tumor specific immune responses. Once stimulated and with help from activated CD4+ T cells, CD8+ T cells will target and kill tumor cells expressing the same neoantigens.

In one embodiment of the present invention, the targeting unit comprises an amino acid sequence having at least 80% sequence identity to the amino acid sequence 24-93 of SEQ ID NO:1. In a preferred embodiment, the targeting unit comprises an amino acid sequence having at least 85% sequence identity to the amino acid sequence 24-93 of SEQ ID NO:1, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity.

In a more preferred embodiment the targeting unit consists of an amino acid sequence having at least 80% sequence identity to the amino acid sequence 24-93 of SEQ ID NO:1, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as at least 100% sequence identity to the amino acid sequence 24-93 of SEQ ID NO:1.

Dimerization Unit

The term "dimerization unit" as used herein, refers to a sequence of amino acids between the antigenic unit and the targeting unit. Thus, the dimerization unit serves to connect the antigenic unit and the targeting unit, and facilitates dimerization of two monomeric polypeptides into a dimeric protein. Furthermore, the dimerization unit also provides the flexibility in the polypeptide/dimeric protein to allow optimal binding of the targeting unit to the surface molecules on the antigen presenting cells (APCs), even if they are located at variable distances. The dimerization unit may be any unit that fulfils these requirements.

Accordingly, in one embodiment the dimerization unit may comprise a hinge region and optionally another domain that facilitates dimerization, and the hinge region and the other domain may be connected through a third linker.

The term "hinge region" refers to a peptide sequence of the dimeric protein that facilitates the dimerization. The hinge region functions as a flexible spacer between the units allowing the two targeting units to bind simultaneously to two target molecules on APCs, even if they are expressed with variable distances. The hinge region may be Ig derived, such as derived from IgG3. The hinge region may contribute to the dimerization through the formation of covalent bond (s), e.g. disulfide bridge(s). Thus, in one embodiment the hinge region has the ability to form one or more covalent bonds. The covalent bond can for example be a disulfide bridge.

In one embodiment, the other domain that facilitates dimerization is an immunoglobulin domain, such as a carboxyterminal C domain, or a sequence that is substantially identical to the C domain or a variant thereof. Preferably, the other domain that facilitates dimerization is a carboxyterminal C domain derived from IgG.

The immunoglobulin domain contributes to dimerization through non-covalent interactions, e.g. hydrophobic interactions. For example, the immunoglobulin domain has the ability to form dimers via noncovalent interactions. Preferably, the noncovalent interactions are hydrophobic interactions.

It is preferred that the dimerization unit does not comprise a CH2 domain.

In a preferred embodiment, the dimerization unit consists of hinge exons h1 and h4 connected through a third linker to a CH3 domain of human IgG3.

In one embodiment of the present invention, the dimerization unit comprises an amino acid sequence having at least 80% sequence identity to the amino acid sequence 94-237 of SEQ ID NO:3. In a preferred embodiment, the dimerization unit comprises an amino acid sequence having at least 85% sequence identity to the amino acid sequence 94-237 of SEQ ID NO:3, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity.

In a more preferred embodiment the dimerization unit consists of an amino acid sequence having at least 80% sequence identity to the amino acid sequence 94-237 of SEQ ID NO:3, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as at least 100% sequence identity to the amino acid sequence 94-237 of SEQ ID NO:3.

In one embodiment the third linker is a G3S2G3SG linker.

It is to be understood that the dimerization unit may have any orientation with respect to antigenic unit and targeting unit. In one embodiment, the antigenic unit is in the COOH-terminal end of the dimerization unit with the targeting unit in the N-terminal end of the dimerization unit. In another embodiment, the antigenic unit is in the N-terminal end of the dimerization unit with the targeting unit in the COOH-terminal end of the dimerization unit. It is preferred that the antigenic unit is in the COOH end of the dimerization unit.

First Linker

The antigenic unit and the dimerization unit are preferably connected through a first linker. The first linker may comprise a restriction site in order to facilitate the construction of the polynucleotide. It is preferred that the first linker is a GLGGL linker or a GLSGL linker.

Signal Peptide

In a preferred embodiment, the polynucleotide further comprises a nucleotide sequence encoding a signal peptide. The signal peptide is constructed to allow secretion of the polypeptide encoded by the polynucleotide of the invention in the cells transfected with said polynucleotide.

Any suitable signal peptide may be used. Examples of suitable peptides are an Ig VH signal peptide, such as SEQ ID NO: 31, a human TPA signal peptide, such as SEQ ID NO: 32, and a signal peptide comprising an amino acid sequence having at least 80% sequence identity to the amino acid sequence 1-23 of SEQ ID NO:1.

In a preferred embodiment, the signal peptide comprises an amino acid sequence having at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity to the amino acid sequence 1-23 of SEQ ID NO:1.

In a more preferred embodiment, the signal peptide consists of an amino acid sequence having at least 80%, preferably at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity to the amino acid sequence 1-23 of SEQ ID NO:1.

Sequence Identity

Sequence identity may be determined as follows: A high level of sequence identity indicates likelihood that the first sequence is derived from the second sequence. Amino acid sequence identity requires identical amino acid sequences between two aligned sequences. Thus, a candidate sequence sharing 70% amino acid identity with a reference sequence requires that, following alignment, 70% of the amino acids in the candidate sequence are identical to the corresponding amino acids in the reference sequence. Identity may be determined by aid of computer analysis, such as, without limitations, the ClustalW computer alignment program (Higgins D., Thompson J., Gibson T., Thompson J. D., Higgins D. G., Gibson T. J., 1994. CLUSTAL W: improving the sensitivity of progressive multiple sequence alignment through sequence weighting, position-specific gap penalties and weight matrix choice. Nucleic Acids Res. 22:4673-4680), and the default parameters suggested therein. Using this program with its default settings, the mature (bioactive) part of a query and a reference polypeptide are aligned. The number of fully conserved residues is counted and divided by the length of the reference polypeptide. In doing so, any tags or fusion protein sequences, which form part of the query sequence, are disregarded in the alignment and subsequent determination of sequence identity.

The ClustalW algorithm may similarly be used to align nucleotide sequences. Sequence identities may be calculated in a similar way as indicated for amino acid sequences.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the FASTA sequence alignment software package (Pearson W R, Methods Mol Biol, 2000, 132:185-219). Align calculates sequence identities based on a global alignment. Align0 does not penalise to gaps in the end of the sequences. When utilizing the ALIGN og Align0 program for comparing amino acid sequences, a BLOSUM50 substitution matrix with gap opening/extension penalties of −12/−2 is preferably used.

Polynucleotides

The invention also relates to a polynucleotide as described above. The polynucleotide may comprise a DNA nucleotide sequence or a RNA nucleotide sequence, such as genomic DNA, cDNA, and RNA sequences, either double stranded or single stranded.

It is preferred that the polynucleotide is optimized to the species to express the polypeptide according to the invention, i.e. it is preferred that the polynucleotide sequence is human codon optimized.

Polypeptides and Dimeric Proteins

The invention further relates to a polypeptide encoded by the polynucleotide sequence as defined above. The polypeptide may be expressed in vitro for production of the vaccine according to the invention, or the polypeptide may be expressed in vivo as a result of administration of the polynucleotide as defined above.

Due to the presence of the dimerization unit, dimeric proteins are formed when the polypeptide is expressed. The dimeric protein may be a homodimer, i.e. wherein the two polypeptide chains are identical and consequently comprise identical neoepitopes, or the dimeric protein may be a heterodimer comprising two different monomeric polypeptides encoded in the antigenic units. The latter may be relevant if the amount of neoepitopes exceeds an upper size limit for the antigenic unit. It is however preferred that the dimeric protein is a homodimeric protein.

Vector

Furthermore, the invention relates to a vector comprising a nucleotide sequence as defined above. It is preferred that the vector allows for easy exchange of the various units described above, in particularly the antigenic unit. In particularly, the expression vector may be pUMVC4a vector or NTC9385R vector backbones. The antigenic unit may be exchanged with an antigenic unit cassette restricted by the SfiI restriction enzyme cassette where the 5' site is incorporated in the GLGGL/GLSGL linker and the 3' site is included after the stop codon in the vector.

Host Cell

The invention also relates to a host cell comprising a nucleotide sequence as defined above or comprising a vector as defined above for expression of the polypeptide according to the invention.

Suitable host cells include prokaryotes, yeast, insect or higher eukaryotic cells.

Methods for Preparing the Vaccine

The vaccine according to the invention is preferably a personalized vaccine in the sense that the neoantigens are identified in the patient's tumor and accordingly, the vaccine is directed exactly against the specific mutated proteins in the patient's tumor.

Accordingly, in one aspect the invention relates to a method for preparing a vaccine comprising an immunologically effective amount of the dimeric protein, or the polypeptide as defined above by producing the polypeptides in vitro. The in vitro synthesis of the polypeptides and proteins may be carried out by any suitable method known to the person skilled in the art, such a through peptide synthesis or expression of the polypeptide in any of a variety of expressions systems followed by purification. Accordingly, in one embodiment the method comprises a) transfecting the polynucleotide as defined above into a cell population;
b) culturing the cell population;
c) collecting and purifying the dimeric protein, or the polypeptide expressed from the cell population, and
d) mixing the dimeric protein or polypeptide obtained under step c) with a pharmaceutically acceptable carrier, thereby obtaining the vaccine.

In a preferred embodiment, the dimeric protein or polypeptide obtained under step c) is dissolved in said pharmaceutically acceptable carrier.

Furthermore, an adjuvant or buffer may be added to the vaccine.

Purification may be carried out according to any suitable method, such as chromatography, centrifugation, or differential solubility.

In another aspect the invention relates to a method for preparing a vaccine comprising an immunologically effective amount of the polynucleotide as defined above. In one embodiment the method comprises a. preparing the polynucleotide as defined above;
b. mixing the polynucleotide obtained under step a) with a pharmaceutically acceptable carrier thereby obtaining the vaccine.

The polynucleotide may be prepared by any suitable method known to the skilled person. For example, the polynucleotide may be prepared by chemical synthesis using an oligonucleotide synthesizer.

In particularly, smaller nucleotide sequences, such as for example nucleotide sequences encoding the targeting unit, the dimerization unit and/or the subunits of the antigenic unit may be synthesized individually and then ligated to produce the final polynucleotide into the vector backbone.

For the design of a personalized vaccine the methods above are preceded by a method of identifying the neoepitopes to be included into the polynucleotide.

This method preferably includes the steps of
sequencing the genome, or exome of a tumor
identifying tumor neoantigens comprising neoepitopes from said tumor,
selecting neoepitopes based on predicted antigenicity.

The tumor or tumor part may be by through any suitable method, such as by obtaining a biopsy of the tumor or by excision of the tumor, or from any suitable body fluid, such as a blood sample or a urine sample.

Sequencing of Tumor Genome or Exome

The genome or the exome, i.e. the coding part of the genome, may be sequenced using any suitable method, such as whole exome sequencing. In particularly the sequencer may be an Illumina HiSeq2500), using Paired-end 2×100-125 or PE100-125 (read length), multiplex.

Identifying Tumor Antigens

Once the tumor specific mutations are identified the next step is to select predicted antigenic peptides comprising the neoepitopes.

Tumor mutations are discovered by sequencing of tumor and normal tissue and make a comparison of the obtained sequences. A variety of methods are available for detecting the presence of a particular mutation or allele in an individual's DNA or RNA. For example techniques including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips may be applied.

Alternatively, a method for identifying mutations by direct protein sequencing may be carried out.

Out of the maybe hundreds or thousands of mutations in the tumor exome, the neoepitopes are selected in silico on the basis of predictive HLA-binding algorithms. The intention is to identify all relevant neoepitopes and after a ranking or scoring determine the neoepitopes to be included in the vaccine for the specific patient in question.

Any suitable algorithms may be used, such as one of the following:

Available free software analysis of peptide-MHC binding (IEDB and NetMHC) may be downloaded from the following websites:
iedb.org/
cbs.dtu.dk/services/NetMHC/

Commercially available advanced software to predict optimal peptides for vaccine design are found here:
oncoimmunity.com/
omictools.com/t-cell-epitopes-category
github.com/griffithlab/pVAC-Seq
crdd.osdd.net/raghava/cancertope/help.php
epivax.com/tag/neoantigen/

Each mutation is scored with respect to its antigenicity, and the most antigenic neoepitopes are selected and optimally designed in the polynucleotide. As discussed above from 3 to 50 neoepitopes are preferred according to the present invention.

Vaccine

The final vaccine is then produced to comprise one of the following:
the polynucleotide as defined above
the polypeptide encoded by the polynucleotide as defined above
the dimeric protein comprising to polypeptide chains The vaccine may further comprise a pharmaceutically acceptable carrier, diluent, adjuvant or buffer.

Pharmaceutically acceptable carriers, diluents, and buffers include, but are not limited to, saline, buffered saline, dextrose, water, glycerol, ethanol, sterile isotonic aqueous buffer, and combinations thereof.

In particularly for vaccines comprising polypeptides/proteins, pharmaceutically acceptable adjuvants include, but are not limited to poly-ICLC, 1018 ISS, aluminum salts, Amplivax, AS 15, BCG, CP-870,893, CpG7909, CyaA, dSLIM, GM-CSF, IC30, IC31, Imiquimod, ImuFact EV1P321, IS Patch, ISS, ISCOMATRIX, JuvImmune, Lipo-Vac, MF59, monophosphoryl lipid A, Montanide IMS 1312, Montanide ISA 206, Montanide ISA 50V, Montanide ISA-51, OK-432, OM-174, OM-197-MP-EC, ONTAK, Pep-Tel.®, vector system, PLGA microparticles, resiquimod, SRL172, Virosomes and other Virus-like particles, YF-17D, VEGF trap, R848, beta-glucan, Pam3Cys, Aquila's QS21 stimulon, vadimezan, and/or AsA404 (DMXAA).

In particularly for vaccines comprising polynucleotides the carriers may include molecules that ease transfection of cells and adjuvants may include plasmids comprising nucleotide sequences encoding chemokines or cytokines in order to enhance the immune response.

The vaccine is formulated into any suitable formulation, such as a liquid formulation for intradermal or intramuscular injection.

Administration

The vaccine may be administered in any suitable way for either a polypeptide/protein vaccine or a polynucleotide vaccine, such as administered by injection intradermally, intramuscularly, subcutaneously, or by mucosal or epithelial application, such as intranasally, orally, enteral or to the bladder.

In particularly the vaccine is preferably administered intramuscular or intradermally when the vaccine is a polynucleotide vaccine.

In a specific embodiment the vaccine is administered by intranodal injection. As used herein, the term "intranodal injection" means that the vaccine is injected into the lymph nodes.

Treatment

The polynucleotides, polypeptides and dimeric proteins are preferably for use in the treatment of cancer, and formulated in a vaccine as discussed above. By the methods described herein it is possible to treat a patient suffering from cancer by examining any mutations present in the tumor in the patient, producing the vaccine and then immunizing the patient with the vaccine directed exactly to neoantigens present in his or her tumor. Due to the fast and reliable methods for sequencing, epitope-determining and producing nucleotide sequences today, it has become likely that a patient may receive the vaccine within 12 weeks from having the tumor resected The cancer may be any cancer wherein the cancer cells comprise mutations. The cancer may be a primary tumor, metastasis or both. The tumor examined for mutations may be a primary tumor or a metastasis. The cancers to be treated are in particularly the cancers known to have a high mutational load, such as melanomas, lung cancer, breast cancer, prostate cancer or colonic cancer.

In a preferred embodiment the treatment is performed with a vaccine comprising a polynucleotide as described above, for example wherein the polynucleotide is DNA or RNA.

It is preferred to inject a polynucleotide vaccine intramuscular, such as in the big muscles, for example in the shoulder, buttock or thigh. It has been found that the polypeptides are produced locally and relevant immune cells internalize the polypeptides/proteins essentially at the site of production, and substantially no polypeptides or proteins reach the blood stream.

Any suitable method for injecting the polynucleotide may be used, such as by the use of a jet injector or assisted by electroporation.

Dosage Regimen

The vaccine may be administered as a single dosage, or may be repeated. When the vaccine administration is repeated it is preferred that it is administered with at least 3 week intervals, to avoid exhaustion of the T cells.

Accordingly, in one embodiment the dosage regimen would be vaccination week 0, 3, 6 and then every 4 weeks as long as the patient has clinical benefit. The vaccine may be administered for at least a year.

The vaccine is administered in an immunologically effective amount. By "immunologically effective amount" is meant the amount of the vaccine required to establish a tumor reducing effect. Ultimately, the physician determines the dosage that typically is in the range of 0.3-6 mg for DNA vaccines, and in the range of 5 µg-5 mg for polypeptide/protein vaccines.

Combination Treatments

The vaccine treatment according to the present invention may be combined with any other anticancer treatment, such as radiation therapy, chemotherapy, and surgical treatment.

The vaccine treatment according to the invention may also be combined with checkpoint-blockade inhibitor treatment.

SPECIFIC EMBODIMENTS

1. A therapeutic anticancer neoepitope vaccine comprising an immunologically effective amount of
   a polynucleotide comprising a nucleotide sequence encoding
   a targeting unit
   a dimerization unit
   a first linker
   an antigenic unit, wherein said antigenic unit comprises n−1 antigenic subunits, each subunit comprising at least a part of a cancer neoepitope sequence and a second linker and said antigenic unit further comprising a final cancer neoepitope sequence, wherein n is an integer of from 3 to 50.
   or
   a polypeptide encoded by the polynucleotide as defined in 1), or
   a dimeric protein consisting of two polypeptides encoded by the polynucleotide as defined in 1).
2. The vaccine according to embodiment 1, wherein the antigenic unit comprises one copy of each cancer neoepitope.
3. The vaccine according to embodiment 1, wherein the antigenic unit comprises at least two copies of at least one neoepitope.
4. The vaccine according to any of the preceding embodiments, wherein the cancer neoepitope sequence has a length of from 7 to 30 amino acids.
5. The vaccine according to embodiment 4, wherein the cancer neoepitope sequence has a length of from 7 to 10 amino acids.
6. The vaccine according to embodiment 4, wherein the cancer neoepitope sequence has a length of from 13 to 30 amino acids.
7. The vaccine according to any of the preceding embodiments, wherein each cancer neoepitope sequence has identical length.
8. The vaccine according to any of the preceding embodiments, wherein the cancer neoepitope is positioned essentially in the middle of the cancer neoepitope sequence.
9. The vaccine according to any of the preceding embodiments, wherein the cancer neoepitope sequence is a subsequence of a cancer neoantigen.
10. The vaccine according to any of the preceding embodiments, wherein the antigenic subunits are in the order of more antigenic to less antigenic from the first linker.
11. The vaccine according to any of the preceding embodiments, wherein the most hydrophobic antigenic subunit(s) is(are) substantially the middle of the antigenic unit and the most hydrophilic antigenic subunit(s) is/are at the ends of the antigenic unit.
12. The vaccine according to any of the preceding embodiments, wherein the second linker is a flexible linker.
13. The vaccine according to any of the preceding embodiments, wherein the second linker is non-immunogenic.
14. The vaccine according to any of the preceding embodiments, wherein the second linker is identical in all antigenic subunits.
15. The vaccine according to any of the preceding embodiments, wherein the second linker is a Serine-Glycine linker.
16. The vaccine according to any of the preceding embodiments, wherein the length of the second linker is from 4 to 20 amino acids.
17. The vaccine according to any of the preceding embodiments, wherein the length of the second linker is 10 amino acids.
18. The vaccine according to any of the preceding embodiments, wherein the length of the antigenic unit is from about 100 amino acids to about a 1000 amino acids.
19. The vaccine according to any of the preceding embodiments, wherein n is an integer between 3 and 30.
20. The vaccine according to any of the preceding embodiments, wherein the dimerization unit comprises a hinge region and optionally another domain that facilitates dimerization, optionally connected through a third linker.
21. The vaccine according to embodiment 20, wherein the hinge region is Ig derived.
22. The vaccine according to any one of embodiments 20-21, wherein the hinge region has the ability to form one or more covalent bonds.
23. The vaccine according to embodiment 22, wherein the covalent bond is a disulfide bridge.
24. The vaccine according to any one of embodiments 20-23, wherein the another domain that facilitates dimerization is an immunoglobulin domain, preferably a carboxyterminal C domain, or a sequence that is substantially identical to said C domain or a variant thereof.
25. The vaccine according to embodiment 24, wherein the carboxyterminal C domain is derived from IgG.
26. The vaccine according to any one of embodiments 24-25, wherein the immunoglobulin domain of the dimerization unit has the ability to homodimerize.
27. The vaccine according to any one of embodiments 24-26, wherein said immunoglobulin domain has the ability to homodimerize via noncovalent interactions.
28. The vaccine according to embodiment 27, wherein said noncovalent interactions are hydrophobic interactions.
29. The vaccine according to any one of embodiments 20-28, wherein said dimerization unit does not comprise a CH2 domain.
30. The vaccine according to any one of embodiments 20-29, wherein the dimerization unit consist of hinge exons h1 and h4 connected through said third linker to a $C_H3$ domain of human IgG3.
31. The vaccine according to any one of embodiments 20-30, wherein the dimerization unit comprises an amino acid sequence having at least 80% sequence identity to the amino acid sequence 94-237 of SEQ ID NO:3.
32. The vaccine according to any one of embodiments 30-31, wherein said third linker is a $G_3S_2G_3SG$ linker.
33. The vaccine according to any of the preceding embodiments, wherein said antigenic unit and the dimerization unit is connected through said first linker.
34. The vaccine according to embodiment 33, wherein the first linker comprises a restriction site.
35. The vaccine according to embodiment 33 or 34, wherein the first linker is a GLGGL linker or a GLSGL linker.

36. The vaccine according to any of the preceding embodiments, wherein the targeting unit has affinity for a chemokine receptor selected from CCR1, CCR3 and CCR5.
37. The vaccine according to any of the preceding embodiments, wherein said targeting unit comprises an amino acid sequence having at least 80% sequence identity to the amino acid sequence 24-93 of SEQ ID NO:1.
38. The vaccine according to any of the preceding embodiments, wherein said targeting unit consists of an amino acid sequence having at least 85% sequence identity to the amino acid sequence 24-93 of SEQ ID NO:1.
39. The vaccine according to any of the preceding embodiments, wherein said nucleotide sequence further encodes a signal peptide.
40. The vaccine according to embodiment 39, wherein said signal peptide comprises an amino acid sequence having at least 80% sequence identity to the amino acid sequence 1-23 of SEQ ID NO:1.
41. The vaccine according to embodiment 39 or 40, wherein said signal peptide consists of an amino acid sequence having at least 85% sequence identity to the amino acid sequence 1-23 of SEQ ID NO:1.
42. The vaccine according to any of the preceding embodiments, wherein said targeting unit, dimerization unit and antigenic unit in said peptide are in the N-terminal to C-terminal order of targeting unit, dimerization unit and antigenic unit.
43. The vaccine according to any of the preceding embodiments, wherein said polynucleotide sequence is human codon optimized.
44. The vaccine according to any of the preceding embodiments, wherein said polynucleotide sequence is a DNA nucleotide sequence or a RNA nucleotide sequence.
45. The vaccine according to any of the preceding embodiments, further comprising a pharmaceutically acceptable carrier and/or adjuvant.
46. A polynucleotide as defined in any of the embodiments 1-45.
47. A vector comprising the nucleotide sequence as defined in any of the embodiments 1-45.
48. A host cell comprising the nucleotide sequence as defined in any of the embodiments 1-45 or comprising the vector as defined in embodiment 47.
49. The polynucleotide according to embodiment 46 formulated for administration to a patient to induce production of the dimeric protein in said patient.
50. A polypeptide encoded by the nucleotide sequence as defined in any of the embodiments 1-45.
51. A dimeric protein consisting of two polypeptides as defined by embodiment 50.
52. The dimeric protein according to embodiment 51, being a homodimeric protein.
53. The polypeptide as defined in embodiment 50, the dimeric protein as defined in embodiment 51-52, or the polynucleotide as defined in embodiment 46 for use as a medicament.
54. A method for preparing a vaccine comprising an immunologically effective amount of the dimeric protein as defined in embodiment 50, or the polypeptide as defined in embodiment 50, the method comprising
e) transfecting the polynucleotide as defined in embodiment 46 into a cell population;
f) culturing the cell population;
g) collecting and purifying the dimeric protein, or the polypeptide expressed from the cell population
h) mixing the dimeric protein or polypeptide obtained under step c) with a pharmaceutically acceptable carrier thereby obtaining the vaccine.
55. A method for preparing a vaccine comprising an immunologically effective amount of the polynucleotide according to embodiment 46, said method comprising
a. preparing the polynucleotide according to embodiment 46;
b. mixing the polynucleotide obtained under step a) with a pharmaceutically acceptable carrier, thereby obtaining the vaccine.
56. The method according to embodiment 55, including the steps of:
sequencing the exome of a tumor
identifying tumor neoantigens comprising neoepitopes from said tumor,
selecting neoepitopes based on antigenicity, prior to the step of preparing the polynucleotide.
57. A method of treating cancer in a patient, the method comprising administering to the patient in need thereof, the vaccine as defined in any of the embodiments 1-45.
58. The method according to embodiments 57, wherein the vaccine comprises a polynucleotide and is administered intradermally or intramuscular.
59. The method according to embodiment 58 wherein the polynucleotide is a DNA.
60. The method according to embodiment 59 wherein the polynucleotide is a RNA.
61. The method according to embodiments 57 to 60, wherein administration is carried out with a jet injector.
62. The method according to embodiments 57 to 60, wherein administration is assisted by electroporation.

EXAMPLES

Example 1: Construction and Expression of the Vaccines

Gene sequences were designed according to the following structure:

| | |
|---|---|
| 1: Native leader sequence for human LD78b. | Signal peptide |
| 2: Full length LD78b sequence. | Targeting unit |
| 3: Human hinge-region 1 from IgG3. | Dimerization unit |
| 4: Human hinge region 4 from IgG3. | |
| 5: Glycine-Serine linker. | |
| 6: Human CH3 domain from IgG3. | |
| 7: Glycine-Leucine linker. | First linker |
| 8: Neoepitope sequence (see below) | Antigenic unit |

Previously described exome sequencing and RNA sequencing of the mouse melanoma cancer cell line B16-F10 and the mouse colon cancer cell line CT26 revealed hundreds to thousands of tumor-specific non-synonymous mutations (Castle et al 2012, Castle et al 2014 and Kreiter et al 2015). In silico-based methods were used to identify potential immunogenic neo-epitopes. Mice were immunized with peptides encoding the mutated epitopes, and their immunogenicity was observed as specific T cell immune responses (ELISpot assay). Furthermore, vaccination of mice with the most immunogenic epitopes selected from the ELISpot conferred strong anti-tumor activity (Castle et al 2012 and Kreiter et al 2015).

Each of the neoepitopes are peptides of 27 amino acids separated by a flexible GGGGS linker. Short peptides (<20 amino acids) are processed and novel epitopes may be presented on MHC class I molecules and activate CD8+ T cells. However, it is preferred that the vaccine activates CD8+ and CD4+ T cells and therefore neoepitopes encoding for long peptides (>20 amino acids) are chosen. That may allow for efficient peptide processing and presentation on both MHC class I and II (Kreiter et al 2015). In the first two VB10.NEO-X constructs the selected hydrophobic and hydrophilic neoepitopes are evenly distributed. A neutral, flexible GGGGS linker between the 27mer neoepitopes is important to avoid generation of new immunogenic epitopes in the junctions of the combined neoepitopes.

The sequences of the neoepitopes found in the B16-F10 and CT26 cell lines are shown in Table 1 and 2.

TABLE 1

CT26 cell line

| Mutation number polypeptide (Vaccibody) | Gene | Mutated sequence used for vaccination | Sub. WT, AA#, Mut) | Reactive T cell subtype | MHC I score (best prediction) |
|---|---|---|---|---|---|
| CT26-PepM1 | E2f8 | VILPQAPSGPSYATYLQPAQAQ MLTPP (SEQ ID NO: 14) | I522T | CD8+ | 0.1 |
| CT26-PepM2 | Aldh18a1 | LHSGQNHLKEMAISVLEARACA AAGQS (SEQ ID NO: 15) | P154S | | |
| CT26-PepM3 | Slc4a3 | PLLPFYPPDEALEIGLELNSSA LPPTE (SEQ ID NO: 16) | T373I | CD4+ | 0.9 |
| CT26-PepM4 | Nphp3 | AGTQCEYWASRALDSEHSIGSM IQLPQ (SEQ ID NO: 17) | G234D | CD4+ | 0.1 |
| CT26-PepM5 | Tdg | AAYKGHHYPGPGNYFWKCLFMS GLSEV (SEQ ID NO: 18) | H169Y | CD4+ | 0.3 |
| CT26-PepM6 | Ubqln1 | DTLSAMSNPRAMQVLLQIQQGL QTLAT (SEQ ID NO: 19) | A62V | | |
| CT26-PepM7 | Slc20a1 | DKPLRRNNSYTSYIMAICGMPL DSFRA (SEQ ID NO: 20) | T425I | CD4+ | 0.3 |
| CT26-PepM8 | Dhx35 | EVIQTSKYYMRDVIAIESAWLL ELAPH (SEQ ID NO: 21) | T646I | CD4+ | 0.1 |
| CT26-PepM9 | Als2 | GYISRVTAGKDSYIALVDKNIM GYIAS (SEQ ID NO: 22) | L675I | CD8+ | 0.2 |
| CT26-PepM10 | Agxt2l2 | EHIHRAGGLFVADAIQVGFGRI GKHFW (SEQ ID NO: 23) | E247A | CD4+ | 0.2 |
| CT26-PepM11 | Tmem87a | QAIVRGCSMPGPWRSGRLLVSR RWSVE (SEQ ID NO: 50) | G63R | CD8+ | 0.7 |
| CT26-PepM12 | Ppp6r1 | DGQLELLAQGALDNALSSMGAL HALRP (SEQ ID NO: 51) | D309N | CD4+ | |
| CT26-PepM13 | Deptor | SHDSRKSTSFMSVNPSKEIKIV SAVRR (SEQ ID NO: 52) | S253N | CD4+ | 0.3 |
| CT26-PepM14 | Napl14 | HTPSSYIETLPKAIKRRINALK QLQVR (SEQ ID NO: 53) | V63I | CD4+ | 0.7 |
| CT26-PepM15 | Cxcr7 | MKAFIFKYSAKTGFTKLIDASR VSETE (SEQ ID NO: 54) | L340F | CD4+ | 1.8 |
| CT26-PepM16 | Dkk2 | EGDPCLRSSDCIDEFCCARHFW TKICK (SEQ ID NO: 55) | G192E | CD4+ | 9.7 |
| CT26-PepM17 | Trip12 | WKGGPVKIDPLALMQAIERYLV VRGYG (SEQ ID NO: 56) | V1328M | CD8+ | |
| CT26-PepM18 | Steap2 | VTSIPSVSNALNWKEFSFIQST LGYVA (SEQ ID NO: 57) | R388K | CD4+ | 6.8 |
| Ct26-PepM19 | Gpc1 | YRGANLHLEETLAGFWARLLER LFKQL (SEQ ID NO: 58) | E165G | CD8+ | 1.9 |
| CT26-PepM20 | Usp26 | KTTLSHTQDSSQSLQSSSDSSK SSRCS (SEQ ID NO: 59) | S715L | n.d. | 5.8 |

TABLE 2

B16-F10 cell line

| Mutation number polypeptide (Vaccibody) | Gene | Mutated sequence used for vaccination | Substi. WT, AA#, Mut | Reactive T cell subtype | MHC I score (best prediction) |
|---|---|---|---|---|---|
| B16-PepM1 | Kif18b | PSKPSFQEFVDWENVSPELNSTDQPFL (SEQ ID NO: 4) | K739N | CD4+ | 1.2 |
| B16-PepM2 | Obsl1 | REGVELCPGNKYEMRRHGTTHSLVIHD (SEQ ID NO: 5) | T176M | CD8+ | 2.3 |
| B16-PepM3 | Def8 | SHCHWNDLAVIPAGVVHNWDFEPRKVS (SEQ ID NO: 6) | R255G | CD4+ | 3.8 |
| B16-PepM4 | Rpl13a | GRGHLLGRLAAIVGKQVLLGRKWVVR (SEQ ID NO: 7) | A24G | CD4+ | 0.5 |
| B16-PepM5 | Tubb3 | FRRKAFLHWYTGEAMDEMEFTEAESNM (SEQ ID NO: 8) | G402A | CD4+ | 1.9 |
| B16-PepM6 | Tnpo3 | WDRNPQFLDPVLAYLMKGLCEKPLAS (SEQ ID NO: 9) | G504A | CD4+ | 1 |
| B16-PepM7 | Atp11a | SSPDEVALVEGVQSLGFTYLRLKDNYM (SEQ ID NO: 10) | R552S | CD4+ | 0.1 |
| B16-PepM8 | Cpsf31 | EFKHIKAFDRTFANNPGPMVVFATPGM (SEQ ID NO: 11) | D314N | CD4+ | 0.5 |
| B16-PepM9 | Plod1 | STANYNTSHLNNDVWQIFENPVDWKEK (SEQ ID NO: 12) | F530V | CD4+ | 0.1 |
| B16-PepM10 | Pbk | DSGSPFPAAVILRDALHMARGLKYLHQ (SEQ ID NO: 13) | V145D | CD8+ | 0.1 |
| B16-PepM11 | Ddx23 | ANFESGKHKYRQTAMFTATMPPAVERL (SEQ ID NO: 36) | V602A | CD4+ | 1.3 |
| B16-PepM12 | Actn4 | NHSGLVTFQAFIDVMSRETTDTDTADQ (SEQ ID NO: 60) | F835V | CD4+ | 0.2 |
| B16-PepM13 | Tm9sf3 | CGTAFFINFIAIYHHASRAIPFGTMVA (SEQ ID NO: 61) | Y382H | CD4+ | 0.2 |
| B16-PepM14 | Eef2 | FVVKAYLPVNESFAFTADLRSNTGGQA (SEQ ID NO: 62) | G795A | CD4+ | 1.1 |
| B16-PepM15 | Gnas | TPPPEEAMPFEFNGPAQGDHSQPPLQV (SEQ ID NO: 63) | S111G | CD4+ | 1.2 |
| B16-PepM16 | Asf1b | PKPDFSQLQRNILPSNPRVTRFHINWD (SEQ ID NO: 64) | A141P | CD4+ | 1.7 |
| B16-PepM17 | Mthfd1l | IPSGTTILNCFHDVLSGKLSGGSPGVP (SEQ ID NO: 65) | F294V | CD4+ | 1.7 |
| B16-PepM18 | Sema3b | GFSQPLRRLVLHVVSAAQAERLARAEE (SEQ ID NO: 66) | L663V | CD4+ | 2.9 |
| B16-PepM19 | Mkm1 | ECRITSNFVIPSEYWVEEKEEKQKLIQ (SEQ ID NO: 67) | N346Y | CD4+ | 1.4 |
| B16-PepM20 | Ppp1r7 | NIEGIDKLTQLKKPFLVNNKINKIENI (SEQ ID NO: 68) | L170P | CD4+ | 3.2 |

Example 2: Comparing Vaccibodies Comprising 3 or 10 Neoepitopes

Vaccibody vaccines containing either 3 or 10 neoepitopes were compared. In the 10 neoepitope Vaccibody DNA construct the place and order for the 3 first (N-terminal) peptides are similar as in the 3 neoepitope Vaccibody DNA construct. This is done to be able to compare the immunogenicity of these 3 neoepitopes in the context with 3 and in the context containing 7 more epitopes.

Figure 1:
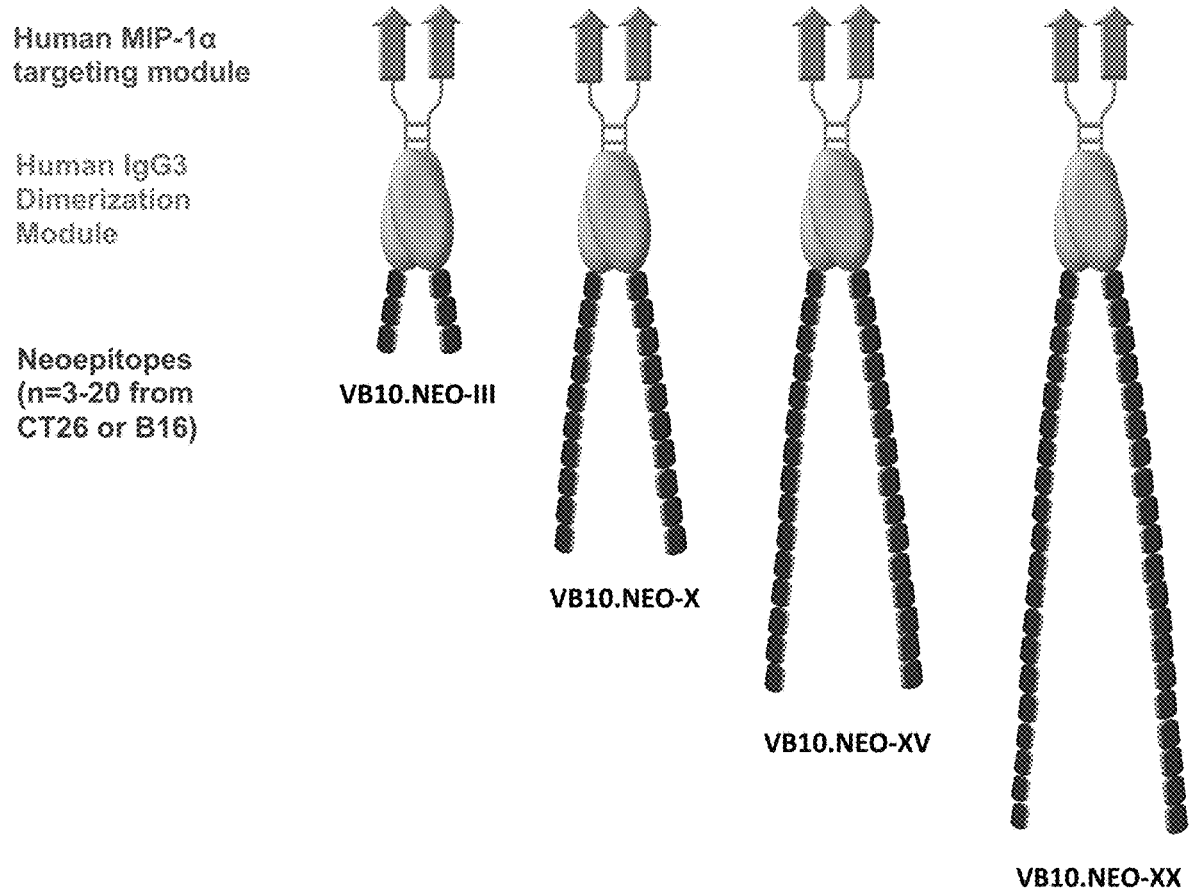
FIG. 1 shows a schematic drawing of a dimeric protein according to the invention having 3, 10 or 20 neoepitopes on each monomer, respectively.

VB4001 (VB10.NEO CT26-X), VB4002 (VB10.NEO CT26-III), VB4003 (VB10.NEO B16-X) and VB4004 (VB10.NEO B16-III) were selected as vaccine candidates. A schematic drawing of the vaccibodies are shown in FIG. 1.

The neoepitopes used for the vaccines VB4001-VB4021 are shown below. For example, VB4015 comprises three neoepitopes, B16 pepM1+pepM8+pepM3 that are separated by 5 amino acid linkers. VB4018 comprises 2 copies of the 10 neoepitopes, B16 pepM1+pepM2+pepM3+pepM4+ pepM11+pepM6+pepM7+pepM8+pepM9+pepM10 that are separated by 5 amino acid linkers. The neoepitope sequences are shown in Tables 1 and 2.

VB4001=VB10.NEO CT26-X=CT26 pepM1-M10, 5 aa linker
VB4002=VB10.NEO CT26-III=CT26 pepM1-M3, 5 aa linker
VB4003=VB10.NEO B16-X=B16 pepM1-M10, 5 aa linker
VB4004=VB10.NEO B16-III=B16 pepM1-M3, 5 aa linker
VB4011=VB10.NEO B16-X=B16 pepM1-M10, 10 aa linker
VB4012=VB10.NEO B16-III=B16 pepM1-M3, 10 aa linker
VB4014=VB10.NEO B16-X=B16 hydrophobic core, (pepM9+pepM5+pepM1+pepM4+pepM6+pepM8+pepM10+pepM3+pepM7+pepM2), 5 aa linker
VB4015=VB10.NEO B16-III=B16 pepM1+M8+M3, 5 aa linker
VB4016=VB10.NEO B16-III=B16 pepM1+M3+M2, 5 aa linker
VB4017=VB10.NEO B16-X=B16 pepM1-M4+M11+M6-M10, 5 aa linker
VB4018=VB10.NEO B16-XX=B16 pepM1-M4+M11+M6-M10×2, 5 aa linker
VB4019=VB10.NEO B16-V×2=B16 pepM3+M4+M7+M9+M10×2, 5 aa linker
VB4021=VB10.NEO B16-V×4=B16 pepM3+M4+M7+M9-M10×4, 5 aa linker All neoepitope gene sequences were ordered from Genescript (New Jersey, US) and cloned into the expression vector pUMVC4a holding the LD78beta targeting unit and the hIgG3 dimerization unit.

Figure 2:
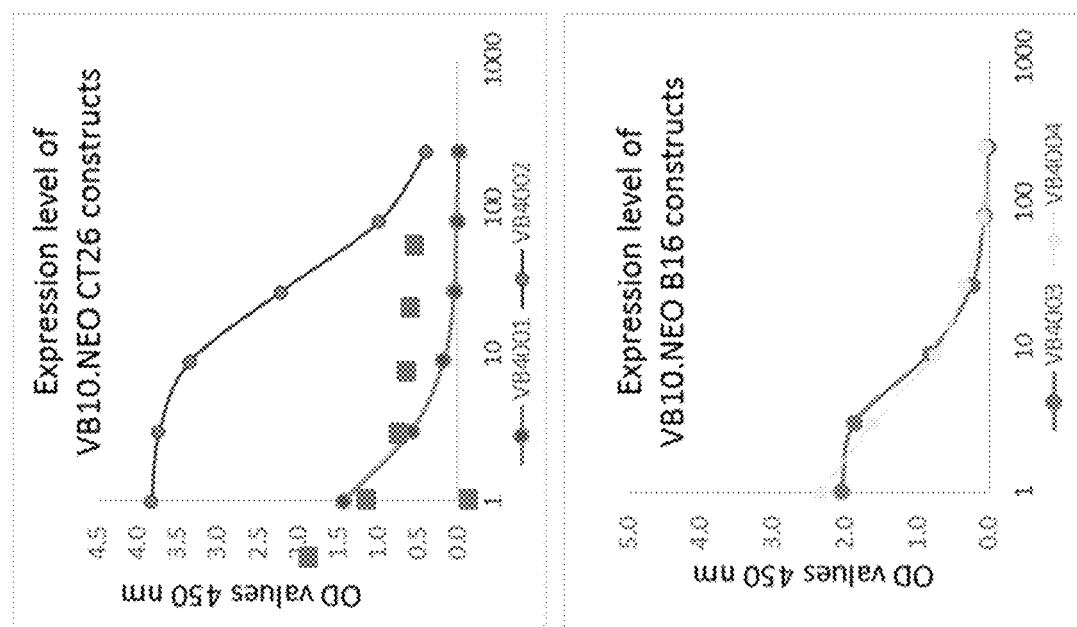
FIG. 2 shows that neoantigen-based vaccibody proteins are produced and secreted as functional homodimers after transfection of HEK293 cells with VB10.NEO constructs.
Figure 2:
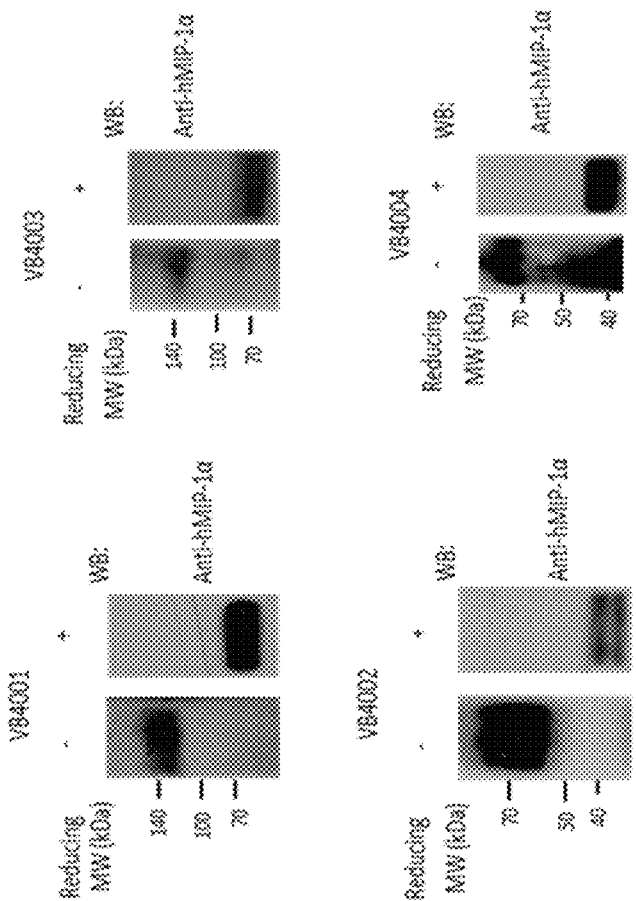

All constructs were transfected into HEK293 cells and Vaccibody proteins in the supernatant were verified by Western blot and/or sandwich ELISA. Empty pUMVC4a vector was included as a negative control. FIG. 2, left panels: To illustrate the formation of intact homodimeric proteins, the proteins in the supernatant from transfected cells were detected in a Western blot by an anti-hMIP-1alpha antibody, in either the presence or absence of reducing agents. The formation of homodimers are shown in the left lane (−reducing agent) whereas the monomers are illustrated in the right lane (+reducing agent). FIG. 2, right panel shows the expression level of the Vaccibody proteins in the supernatant of HEK293 cells transfected with the different VB10.NEO constructs detected by a sandwich ELISA using antibodies against both hMIP-1alpha and hIgG3. Right, upper panel shows the expression level of the VB10.NEO CT26-X (VB4001) and VB10.NEO CT26-III (VB4002) constructs, comprising 10 or 3 neoepitopes, respectively. Right, lower panel shows the expression level of the VB10.NEO B16-X (VB4003) and VB10.NEO B16-III (VB4004) constructs, comprising 10 or 3 neoepitopes, respectively. To compare the immunogenicity of vaccibodies comprising 3 or 10 neoepitopes, 20 μg plasmid DNA of each vaccibody candidate were injected intramuscularly in the tibial anterior muscle of C57Bl/6-mice (for B16 constructs) or BALB/c-mice (for CT26 constructs), followed by electroporation using TriGrid, Ichor, (US). At day 13, the mice were euthanized and spleens were harvested.

Figure 3:
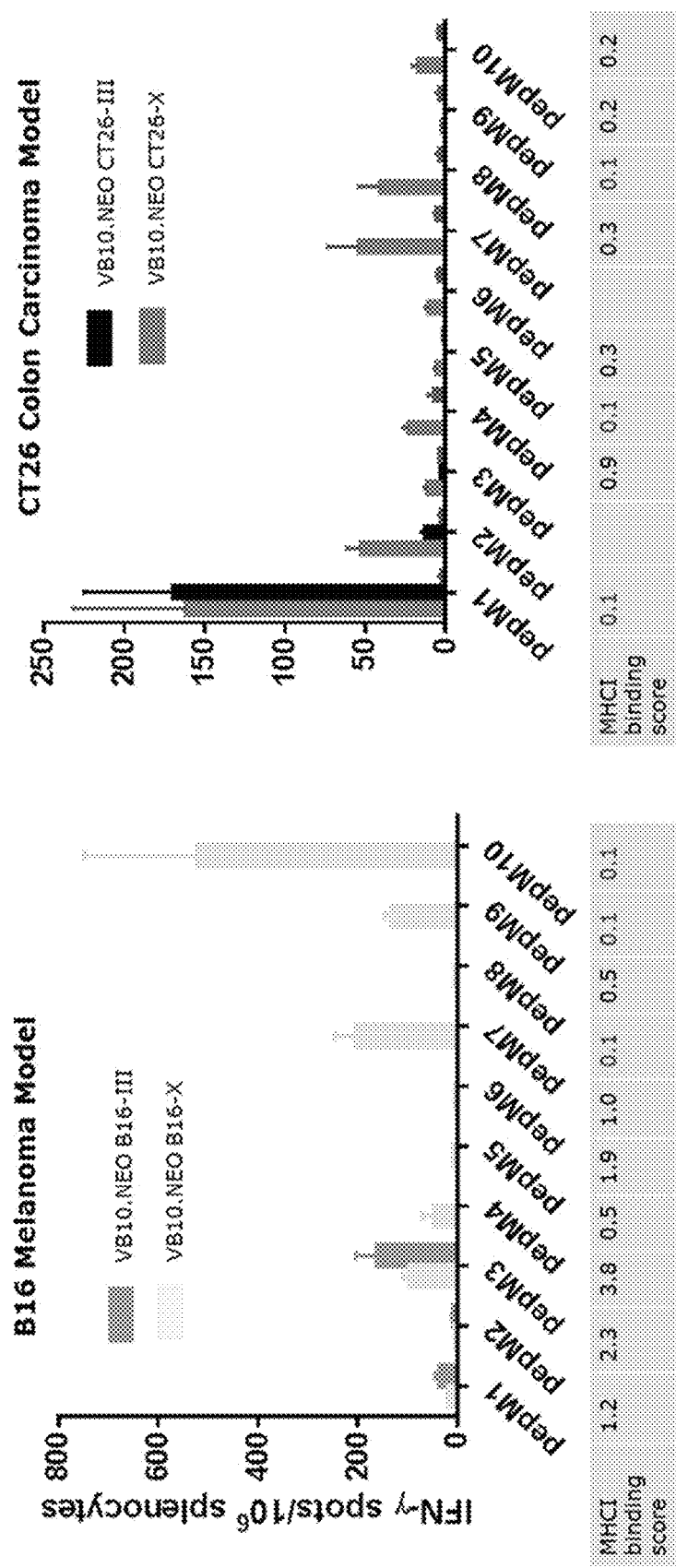
FIG. 3 illustrates that strong and broad T-cell responses are induced after a single injection with vaccibody DNA vaccines comprising 10 neoepitopes when compared to vaccibody DNA vaccines comprising 3 neoepitopes. The left panel displays IFN-γ responses towards individual neoepitopes in the B16 melanoma model when injecting VB10.NEO B16-III (VB4004) or VB10.NEO B16-X (VB4003) comprising 3 and 10 neoepitopes, respectively. The right panel displays IFN-γ responses towards neoepitopes in the CT26 colon carcinoma model when injecting VB10.NEO CT26-III (VB4002) or VB10.NEO CT26-X (VB4001) comprising 3 and 10 neoepitopes, respectively. The x-axis represents the 10 different neoepitopes, pepM1-M10.
 VB10.NEO CT26-X=VB4001=CT26 pepM1-M10,
 VB10.NEO CT26-III=VB4002=CT26 pepM1-M3,
 VB10.NEO B16-X=VB4003=B16 pepM1-M10,
 VB10.NEO B16-III=VB4004=B16 pepM1-M3.

The T cell responses were evaluated by IFN-gamma ELISpot. The results are shown in FIG. 3 where the T cell responses are indicated as the number of IFN-γ spots/$10^6$ splenocytes. We observe that vaccibodies comprising 10 neoepitopes induces significant T cell responses towards 4-6 of 10 included neoepitopes in the same mice. The peptides stimulating the strongest IFN-γ response generally have the best MHC I binding score.

The total neoantigen-specific immune responses induced by vaccibody constructs comprising 3 or 10 neoepitopes are depicted in FIG. 4. Vaccibodies comprising 10 neoepitopes (VB10.NEO B16-X and VB10.NEO CT26-X) resulted in an increased total neoantigen-specific immune response when compared with vaccibodies comprising 3 neoepitopes (VB10.NEO B16-III and VB10.NEO CT26-III).

Figure 5:
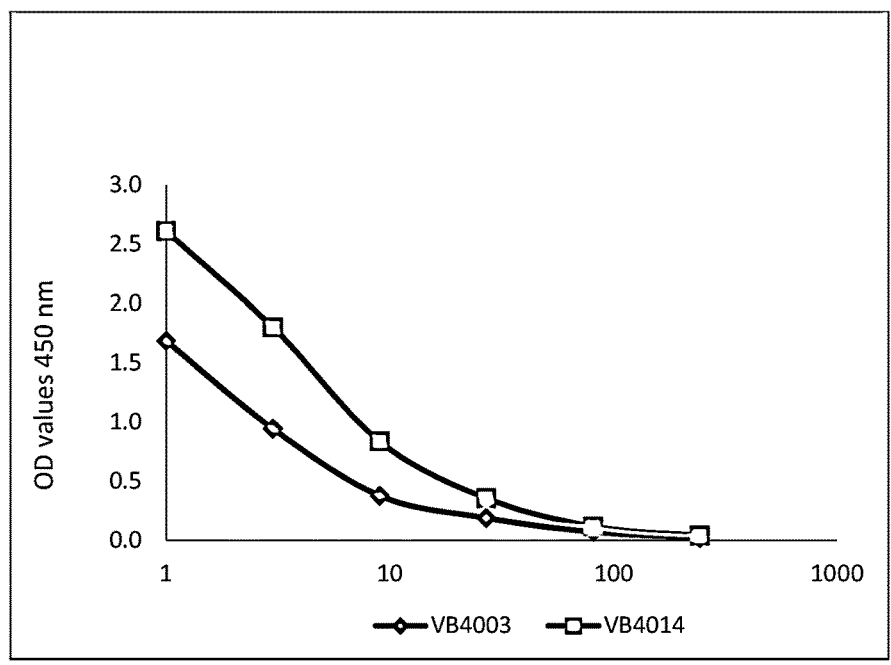
FIG. 5. Vaccibody DNA vaccines comprising 10 neoepitopes induce a much stronger immune response than a mix of the corresponding 10 peptides plus adjuvant. Upper panel: Comparison of the vaccibody expression level of two variants of VB10.NEO B16-X with varying order of the 10 neoepitopes (VB4003 and VB4014) in the supernatant of HEK293 cells transfected with the corresponding Vaccibody DNA constructs, detected by sandwich ELISA. In VB4003, every other neoepitope is either hydrophobic or hydrophilic, whereas in VB4014, the hydrophobic neoepitopes are placed centrally in the neoepitope antigenic module. A hydrophobic core of neoepitopes in the antigenic module may improve expression and secretion of functional vaccibody proteins in the same constructs. Lower panel: The histogram shows immune responses induced by the DNA vaccines VB10.NEO B16-X VB4003 and VB4014, and a mix of 10 peptides plus adjuvant (the same 10 neoepitopes as encoded in the VB10.NEO B16-X constructs). The order of the neoepitopes within the neoepitope antigenic module does not change the hierarchy of the immunogenicity of the individual neoepitopes.
 VB10.NEO B16-X=VB4003=B16 pepM1-M10,
 VB10.NEO B16-X=VB4014=B16 hydrophobic core (pepM9+pepM5+pepM1+pepM4+pepM6+pepM8+ pepM10+pepM3+pepM7+pepM2).
Figure 5:
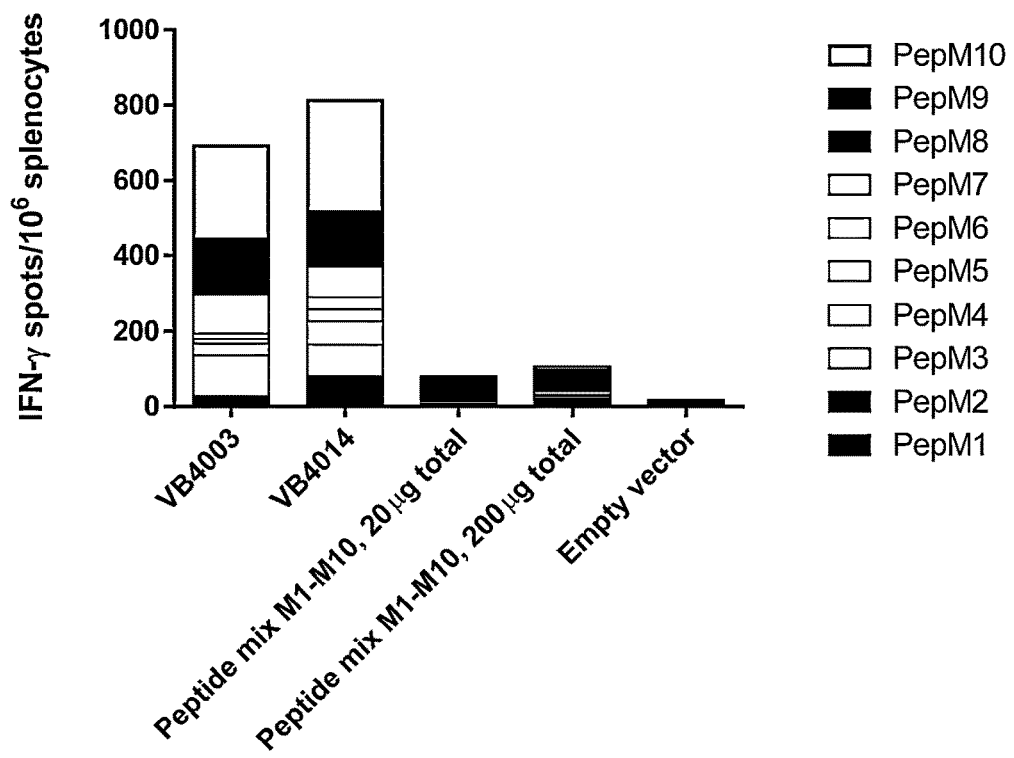

Example 3: Comparing Immunogenicity of Vaccibody DNA Vaccines and Corresponding Peptide Plus Adjuvant Vaccines Before the VB10.NEO constructs are used in mice vaccination studies, Vaccibody protein expression and secretion in HEK293 cells are verified using a sandwich ELISA assay, as previously described in detail in the text for FIG. 2. The order of the neoepitopes could have an impact on the expression and secretion of functional Vaccibodies. In FIG. 5, upper panel we observe that the VB10.NEO B16-X construct VB4014 has a slightly improved expression and secretion of functional vaccibody proteins compared to the VB10.NEO B16-X construct VB4003. The 10 neoepitopes in VB4014 is similar as for VB4003, however the order of the neoepitopes are changed and the most hydrophobic neoepitopes are located in the core in the neoepitope antigenic module. To test immunogenicity of Vaccibody DNA vaccines VB4003 and VB4014 compared with peptides comprising only neoepitopes delivered in combination with the poly (I:C) adjuvant, C57/Bl6 mice were injected with 20 μg of the VB10.NEO B16-X constructs VB4003 and VB4014 (The induced immune responses were compared with immune responses of mice s.c. injected with 20 μg or 200 μg peptide mix+50 μg poly I:C comprising the 10 neoepitopes encoded by VB4003 and VB4014. The T cell responses were evaluated by IFN-gamma ELISpot. The results, shown in FIG. 5 lower panel, illustrate that the vaccibodies clearly induces a much stronger response than peptide+adjuvant. Moreover, some of the animals immunized with the VB10.NEO B16-X VB4014 construct responded to all 10 neoepitopes included in the vaccine.

Figure 6:
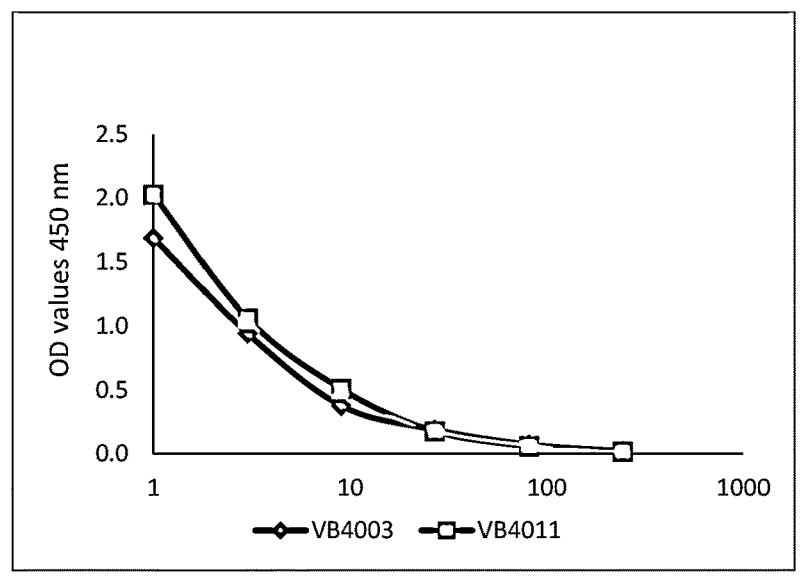
FIG. 6. VB10.NEO B16-X DNA vaccine where the 10 neoepitopes are spaced with 10 amino acid (aa) linkers (VB4011), induces a stronger total immune response, compared to VB10.NEO B16-X DNA vaccine where the 10 neoepitopes are spaced with 5 aa linkers (VB4003). Upper panel: Comparison of the vaccibody expression level of VB4003 and VB4011 in the supernatant of HEK293 cells transfected with the corresponding Vaccibody DNA constructs, detected by sandwich ELISA. Similar expression and secretion of functional vaccibody proteins are observed for VB4003 and VB4011. Lower panel: Histogram showing the IFN-γ immune response towards neoepitopes from the B16 melanoma model in mice injected with VB4003 or VB4011. A single injection with vaccibody DNA vaccines comprising 10 neoepitopes spaced with 10 amino acid linkers resulted in the strongest total immune response. Empty vector was included as a negative control.
Figure 6:
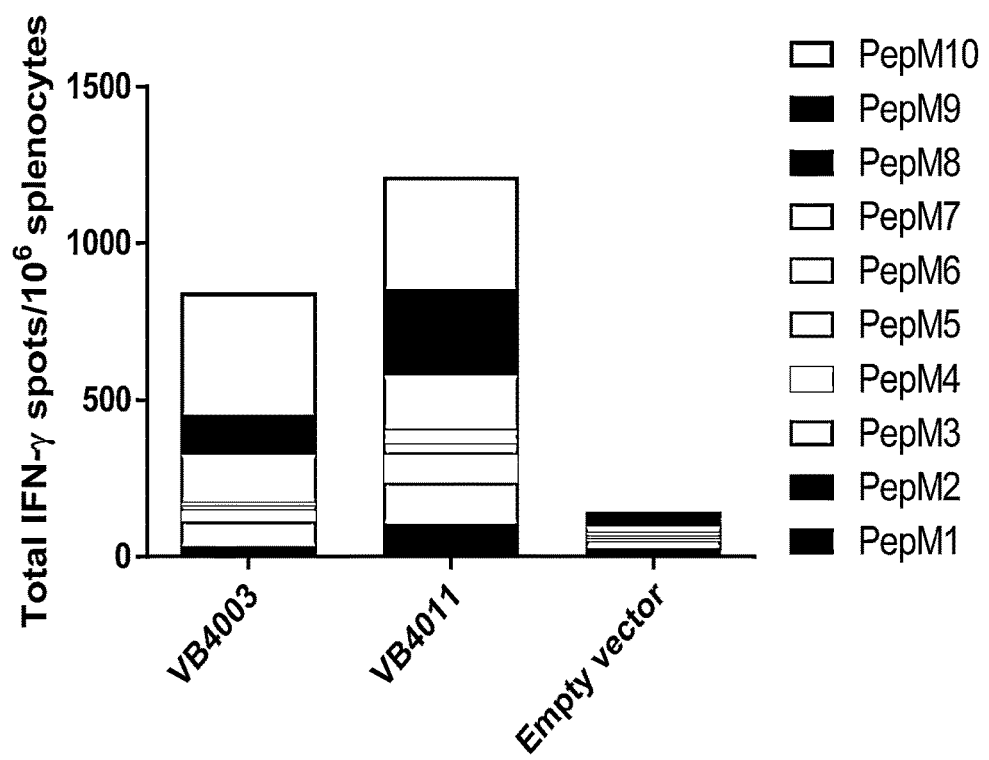

Example 4: Comparing Vaccibodies Comprising Second Linkers with a Length of 5 or 10 Amino Acids Each of the neoepitopes is separated by a second linker. In the present example the second linker is a flexible GGGGS linker. To test if the length of the second linker has any effect on the expression level, HEK293 cells were transfected with VB10.NEO B16-X constructs comprising second linkers with a length of either 5 or 10 amino acids. FIG. 6 illustrates that changing the linker length from 5 (VB4003) to 10 (VB4011) amino acids does not affect expression of vaccibodies comprising 10 neoepitopes (FIG. 6, upper panel). To test if the length of the second linker has any effect on the immune response, C57Bl/6 mice were injected with VB10.NEO B16-X constructs comprising 10 neoepitopes with either 5 (VB4003) or 10 (VB4011) amino acid linkers. At day 13, the mice were sacrificed and splenocytes harvested, stimulated with the individual corresponding neoepitope peptides for 24 hours and T cell responses were quantified in an IFN-gamma ELISpot assay. The results are shown in FIG. 6, lower panel, and demonstrate that vaccibody constructs comprising 10 amino acid linkers (VB4011) lead to an increased total immune response when compared to vaccibodies comprising 5 amino acid linkers (VB4003). Empty vector was included as a negative control.

Example 5: Comparing Vaccibodies Comprising Different Number of Copies of Identical Neoepitopes The following constructs were tested:
VB4003=VB10.NEO B16-X=B16 pepM1-M10, 5 aa linker
VB4018=VB10.NEO B16-XX=B16 pepM1-M4+M11+M6-M10×2, 5 aa linker The expression level of VB10.NEO B16-X (VB4003) construct comprising 10 neoepitopes was compared to the expression level of VB10.NEO B16-XX (VB4018) comprising 2×10 neoepitopes. The results demonstrate that VB10.NEO B16-XX (VB4018) comprising 20 neoepitopes are slightly less expressed compared to VB10.NEO B16-X (VB4003) comprising 10 neoepitopes (FIG. 7, upper panel).

The immunogenicity of Vaccibodies comprising either 10 or 20 neoepitopes was tested by intramuscular injection of C57Bl/6 mice with the Vaccibody DNA vaccine VB10.NEO B16-X (VB4003) and VB10.NEO B16-XX (VB4018) At day 13, the mice were sacrificed and splenocytes harvested, stimulated with the individual corresponding neoepitope peptides for 24 hours and T cell responses were quantified in an IFN-gamma ELISpot assay. The results shown in FIG. 7, lower panel illustrate that the benefit of including 2 copies per neoepitope (2×10 neoepitopes) is limited on the total immune response, however, a broader immune response is observed towards individual neoepitopes.

Next, the expression levels of Vaccibody constructs comprising one or more copies of the 5 selected neoepitopes, PepM3, PepM4, PepM7, PepM9 and PepM10, were tested (FIG. 8, upper panel).

C57Bl/6 mice were injected with the following Vaccibody constructs:
VB4003=VB10.NEO B16-X=B16 pepM1-M10, 5 aa linker
VB4011=VB10.NEO B16-X=B16 pepM1-M10, 10 aa linker
VB4018=VB10.NEO B16-XX=B16 pepM1-M4+M11+M6-M10×2, 5 aa linker
VB4019=VB10.NEO B16-V×2=B16 pepM3+M4+M7+M9+M10×2, 5 aa linker
VB4021=VB10.NEO B16-V×4=B16 pepM3+M4+M7+M9+M10×4, 5 aa linker The immune responses of the Vaccibody candidates for each of the five selected neoepitopes are shown in FIG. 8, lower panel. Multiple copies of the five neoepitopes had limited effect on the total immune response. However, several copies of each neoepitope (VB4018, VB4019 and VB4021) gives a more evenly immune response towards the 5 shared neoepitopes compared to the decatope VB4003, where the 5 neoepitopes are presented once. Interestingly, Vaccibodies comprising a 10 amino acid second linker and the neoepitopes only once (VB4011) displayed a better total immune response than Vaccibodies comprising multiple copies of the five neoepitopes.

Example 6: Comparing Vaccibodies Comprising Different Number of Neoepitopes

The immune response of vaccibody constructs comprising different numbers of neoepitopes were compared to test the immunological effect of adding further neoepitopes.

The total immune response was tested in the B16 melanoma mouse model using the following constructs:
NEO B16-X=VB4011=B16 pepM1-M10, 10 aa linker
NEO B16-XV=VB4024=B16 pepM1-M15, 10 aa linker
NEO B16-XX=VB4025=B16 pepM1-M20, 10 aa linker
The neoepitope sequences are shown in Table 2.

The expression levels of the three tested vaccibody constructs are shown in FIG. 11, upper panel.

C57Bl/6 mice were injected with the DNA vaccine candidates VB10.NEO B16-XV comprising 15 neoepitopes (VB4024) or VB10.NEO B16-XX comprising 20 neoepitopes (VB4025) compared to the VB10.NEO B16-X comprising 10 neoepitopes (VB4011). FIG. 11, lower panel, shows the total number of IFNγ-spots per $10^6$ splenocytes. Constructs with 15 and 20 neoepitopes resulted in a broader immune response against more individual neoepitopes and a higher total T cell response when compared to constructs with only 10 neoepitopes. As a negative control, mice were injected with empty vector not comprising the neoepitopes. As seen from FIG. 11, lower panel, injections with empty vector did not lead to any significant immune response against the individual neoepitopes.

Further, the total immune response was tested in the CT26 melanoma mouse model using the following constructs
NEO CT26-X=VB4009=CT26 pepM1-M10, 10 aa linker
NEO CT26-XV=VB4026=CT26 pepM1-M15, 10 aa linker
NEO CT26-XX=VB4027=CT26 pepM1-M20, 10 aa linker
The neoepitope sequences are shown in Table 1.

BALB/c mice were injected with the DNA vaccine candidates VB10.NEO CT26-XV comprising 15 neoepitopes (VB4026) or VB10.NEO CT26-XX comprising 20 neoepitopes (VB4027) compared to the VB10.NEO CT26-X comprising 10 neoepitopes (VB4009). FIG. 12, lower panel, shows the total number of IFNγ-spots per $10^6$ splenocytes. Constructs with 15 and 20 neoepitopes resulted in a broader immune response against more individual neoepitopes and a higher total T cell response when compared to constructs with only 10 neoepitopes. As a negative control, mice were injected with empty vector not comprising the neoepitopes. As seen from FIG. 12, lower panel, injections with empty vector did not lead to any significant immune response against the individual neoepitopes.

Example 7: Expression Levels of Different Vaccibody Constructs—Are Compared

The following constructs were tested:
VB4004=VB10.NEO B16-III=B16 pepM1-M3, 5 aa linker
VB4012=VB10.NEO B16-III=B16 pepM1-M3, 10 aa linker
VB4015=VB10.NEO B16-III=B16 pepM1+M8+M3, 5 aa linker
VB4016=VB10.NEO B16-III=B16 pepM1+M3+M2, 5 aa linker VB4017=VB10.NEO B16-X=B16 pepM1-M4+M11+ M6-M10, 5 aa linker VB4018=VB10.NEO B16-XX=B16 pepM1-M4+M11+ M6-M10×2, 5 aa linker Similar expression and secretion of functional vaccibody proteins are observed for VB10.NEO B16-X (VB4017) and VB10.NEO B16-XX (VB4018) (FIG. 9).

Improved expression and secretion of functional vaccibody proteins are observed when the 3 neoepitopes are spaced with a 10 aa linker as in the VB10.NEO B16-III (VB4012) construct compared to a 5 aa linker in the VB10.NEO B16-III (VB4004) construct (FIG. 10, upper panel). Moreover, by changing the order of the three neoepitopes as shown by comparing VB4004, VB4015 and VB4016 (FIG. 10, lower panel), may affect the expression levels of the vaccibodies.

Example 8: Therapeutic Effect

VB10.NEO were used as vaccine candidates for therapeutic vaccine studies.

$7.5 \times 10^4$ B16.F10 cells or $1 \times 10^5$ CT26 cells (ATCC) was injected in the thigh region of C57Bl/6 mice or BALB/c mice. After 1 and 8 days, the mice were vaccinated with 20 µg plasmid DNA followed by electroporation, TriGrid, Ichor, US. Tumor sizes were measured two to three times a week. FIG. 13 shows that VB10.NEO DNA vaccine candidates comprising 10 neoepitopes are able to significantly delay and reduce tumour growth.

Example 9: Therapeutic DNA Vaccine

A therapeutic DNA vaccine to be used may be prepared by GMP manufacturing of the plasmid vaccine according to regulatory authorities' guidelines, and Fill & Finish of the DNA vaccine. The DNA vaccine may be formulated by dissolving in a saline solution, such as PBS at a concentration of 2-6 mg/ml. The vaccine may be administered either intradermal or intramuscular with or without following electroporation or alternatively with a jet injector.

```
SEQUENCES
C-C motif chemokine 3-like 1 precursor
including signal peptide and mature
peptide (LD78-beta), aa 24-93:
                                SEQ ID NO: 1
MQVSTAALAVLLCTMALCNQVLSAPLAADTPTACCFSYTSRQIPQNFIAD

YFETSSQCSKPSVIFLTKRGRQVCADPSEEWVQKYVSDLELSA

DNA sequence of constant coding part of all
VB10.NEO constructs
For the purpose of illustration only, the
different domains of the constructs are
separated by an "|" with the domains in the
following order: Signal peptide|human MIP-1α|
Hinge hi|Hinge h4|Gly-Ser Linker or Gly-Leu
linker|hCH3 IgG3|Gly-Ser Linker or Gly-Leu
linker|
The construct is a standard construct that
can be used to insert neoepitopes. Neoepitope
sequences can be added after the linker
GGCCTCGGTGGCCTG.
                                SEQ ID NO: 2
ATGCAGGTCTCCACTGCTGCCCTTGCCGTCCTCCTCTGCACCATGGCTCT

CTGCAACCAGGTCCTCTCT|GCACCACTTGCTGCTGACACGCCGACCGCC

TGCTGCTTCAGCTACACCTCCCGACAGATTCCACAGAATTTCATAGCTGA

CTACTTTGAGACGAGCAGCCAGTGCTCCAAGCCCAGTGTCATCTTCCTAA

CCAAGAGAGGCCGGCAGGTCTGTGCTGACCCCAGTGAGGAGTGGGTCCAG

AAATACGTCAGTGACCTGGAGCTGAGTGCC|GAGCTCAAAACCCCACTTG

GTGACACAACTCACACA|GAGCCCAAATCTTGTGACACACCTCCCCCGTG

CCCAAGGTGCCCA|GGCGGTGGAAGCAGCGGAGGTGGAAGTGGA|GGACA

GCCCCGAGAACCACAGGTGTACACCCTGCCCCCATCCCGGGAGGAGATGA

CCAAGAACCAGGTCAGCCTGACCTGCCTGGTCAAAGGCTTCTACCCCAGC

GACATCGCCGTGGAGTGGGAGAGCAGCGGGCAGCCGGAGAACAACTACAA

CACCACGCCTCCCATGCTGGACTCCGACGGCTCCTTCTTCCTCTACAGCA

AGCTCACCGTGGACAAGAGCAGGTGGCAGCAGGGGAACATCTTCTCATGC

TCCGTGATGCATGAGGCTCTGCACAACCGCTTCACGCAGAAGAGCCTCTC

CCTGTCTCCGGGTAAA|GGCCTCGGTGGCCTG|

Amino acid sequence of constant coding part
of all VB10.NEO proteins:B4001
                                SEQ ID NO: 3
MQVSTAALAVLLCTMALCNQVLS|APLAADTPTACCFSYTSRQIPQNFIA

DYFETSSQCSKPSVIFLTKRGRQVCADPSEEWVQKYVSDLELSA|ELKTP

LGDTTHTIEPKSCDTPPPCPRCP|GGGSSGGGSG|GQPREPQVYTLPPSR

EEMTKNQVSLTCLVKGFYPSDIAVEWESSGQPENNYNTTPPMLDSDGSFF

LYSKLTVDKSRWQQGNIFSCSVMHEALHNRFTQKSLSLSPGK|GLGGL|

B16-F10 mutated epitope, B16-PepM1,
amino acid sequence
                                SEQ ID NO: 4
PSKPSFQEFVDWENVSPELNSTDQPFL B16-F10 mutated epitope, B16-PepM2,
amino acid sequence
                                SEQ ID NO: 5
REGVELCPGNKYEMRRHGTTHSLVIHD B16-F10 mutated epitope, B16-PepM3,
amino acid sequence
                                SEQ ID NO: 6
SHCHWNDLAVIPAGVVHNWDFEPRKVS B16-F10 mutated epitope, B16-PepM4,
amino acid sequence
                                SEQ ID NO: 7
GRGHLLGRLAAIVGKQVLLGRKVVVVR B16-F10 mutated epitope, B16-PepM5,
amino acid sequence
                                SEQ ID NO: 8
FRRKAFLHWYTGEAMDEMEFTEAESNM B16-F10 mutated epitope, B16-PepM6,
amino acid sequence
                                SEQ ID NO: 9
WDRNPQFLDPVLAYLMKGLCEKPLAS B16-F10 mutated epitope, B16-PepM7,
amino acid sequence
                                SEQ ID NO: 10
SSPDEVALVEGVQSLGFTYLRLKDNYM B16-F10 mutated epitope, B16-PepM8,
amino acid sequence
                                SEQ ID NO: 11
EFKHIKAFDRTFANNPGPMVVFATPGM
```

-continued

B16-F10 mutated epitope, B16-PepM9, amino acid sequence
SEQ ID NO: 12
STANYNTSHLNNDVWQIFENPVDWKEK B16-F10 mutated epitope, B16-PepM10, amino acid sequence
SEQ ID NO: 13
DSGSPFPAAVILRDALHMARGLKYLHQ CT26 mutated epitope, CT26-PepM1, amino acid sequence
SEQ ID NO: 14
VILPQAPSGPSYATYLQPAQAQMLTPP CT26 mutated epitope, CT26-PepM2, amino acid sequence
SEQ ID NO: 15
LHSGQNHLKEMAISVLEARACAAAGQS CT26 mutated epitope, CT26-PepM3, amino acid sequence
SEQ ID NO: 16
PLLPFYPPDEALEIGLELNSSALPPTE CT26 mutated epitope, CT26-PepM4, amino acid sequence
SEQ ID NO: 17
AGTQCEYWASRALDSEHSIGSMIQLPQ CT26 mutated epitope, CT26-PepM5, amino acid sequence
SEQ ID NO: 18
AAYKGHHYPGPGNYFWKCLFMSGLSEV CT26 mutated epitope, CT26-PepM6, amino acid sequence
SEQ ID NO: 19
DTLSAMSNPRAMQVLLQIQQGLQTLAT CT26 mutated epitope, CT26-PepM7, amino acid sequence
SEQ ID NO: 20
DKPLRRNNSYTSYIMAICGMPLDSFRA CT26 mutated epitope, CT26-PepM8, amino acid sequence
SEQ ID NO: 21
EVIQTSKYYMRDVIAIESAWLLELAPH CT26 mutated epitope, CT26-PepM9, amino acid sequence
SEQ ID NO: 22
GYISRVTAGKDSYIALVDKNIMGYIAS CT26 mutated epitope, CT26-PepM10, amino acid sequence
SEQ ID NO: 23
EHIHRAGGLFVADAIQVGFGRIGKHFW First linker, amino acid sequence:
SEQ ID NO: 24
GLSGL First linker, amino acid sequence:
SEQ ID NO: 25
GLGGL Hinge regions (IgG3 UH hinge), 12 amino acids:
SEQ ID NO: 26
ELKTPLGDTTHT Hinge region (IgG3, MH hinge, 15 amino acids):
SEQ ID NO: 27
EPKSCDTPPPCPRCP Gly-Ser Linker:
SEQ ID NO: 28
GGGSSGGGSG hCH3 IgG3, amino acid sequence:
SEQ ID NO: 29
GQPREPQVYTLPPSREEMTKNQVSLTCLVKGFYPSDIAVEWESSGQPENN
YNTTPPMLDSDGSFFLYSKLTVDKSRWQQGNIFSCSVMHEALHNRFTQKS
LSLSPGK Amino acid sequence of VB4001 = VB10.NEO
CT26-X = CT26 pepM1-M10, 5 aa linker
The neoepitope sequences are inserted after GGGSSGGGSG.
SEQ ID NO: 30
MQVSTAALAVLLCTMALCNQVLS|APLAADTPTACCFSYTSRQIPQNFIA
DYFETSSQCSKPSVIFLTKRGRQVCADPSEEWVQKYVSDLELSA|ELKTP
LGDTTHTIEPKSCDTPPPCPRCP|GGGSSGGGSG|GQPREPQVYTLPPSR
EEMTKNQVSLTCLVKGFYPSDIAVEWESSGQPENNYNTTPPMLDSDGSFF
LYSKLTVDKSRWQQGNIFSCSVMHEALHNRFTQKSLSLSPGK|GLGGL|M
HGDTPTLHEYMLDLQPETTDLYGYGQLNDSSEEEDEIDGPAGQAEPDRAH
YNIVTFCCKCDSTLRLCVQSTHVDIRTLEDLLMGTLGIVCPICSQKP|GG
GSSGGGSG|VILPQAPSGPSYATYLQPAQAQMLTPPGGGGSLHSGQNHLK
EMAISVLEARACAAAGQSGGGGSPLLPFYPPDEALEIGLELNSSALPPTE
GGGGSAGTQCEYWASRALDSEHSIGSMIQLPQGGGGSAAYKGHHYPGPGN
YFWKCLFMSGLSEVGGGGSDTLSAMSNPRAMQVLLQIQQGLQTLATGGGG
SDKPLRRNNSYTSYIMAICGMPLDSFRAGGGGSEVIQTSKYYMRDVIAIE
SAWLLELAPHGGGGSGYISRVTAGKDSYIALVDKNIMGYIASGGGGSEHI
HRAGGLFVADAIQVGFGRIGKHFW Amino acid sequence of VB4002 VB10.NEO
CT26-III = CT26 pepM1-M3, 5 aa linker
SEQ ID NO: 31
MQVSTAALAVLLCTMALCNQVLS|APLAADTPTACCFSYTSRQIPQNFIA
DYFETSSQCSKPSVIFLTKRGRQVCADPSEEWVQKYVSDLELSA|ELKTP
LGDTTHT}EPKSCDTPPPCPRCP|GGGSSGGGSG|GQPREPQVYTLPPSR
EEMTKNQVSLTCLVKGFYPSDIAVEWESSGQPENNYNTTPPMLDSDGSFF
LYSKLTVDKSRWQQGNIFSCSVMHEALHNRFTQKSLSLSPGK|GLGGL|M
HGDTPTLHEYMLDLQPETTDLYGYGQLNDSSEEEDEIDGPAGQAEPDRAH
YNIVTFCCKCDSTLRLCVQSTHVDIRTLEDLLMGTLGIVCPICSQKP|GG
GSSGGGSG|VILPQAPSGPSYATYLQPAQAQMLTPPGGGGSLHSGQNHLK
EMAISVLEARACAAAGQSGGGGSPLLPFYPPDEALEIGLELNSSALPPTE Amino acid sequence of VB4003 = VB10.NEO
B16-X = B16 pepM1-M10, 5 aa linker
(VB10.Neo-10B)
SEQ ID NO: 32
MQVSTAALAVLLCTMALCNQVLS|APLAADTPTACCFSYTSRQIPQNFIA
DYFETSSQCSKPSVIFLTKRGRQVCADPSEEWVQKYVSDLELSA|ELKTP
LGDTTHTIEPKSCDTPPPCPRCP|GGGSSGGGSG|GQPREPQVYTLPPSR
EEMTKNQVSLTCLVKGFYPSDIAVEWESSGQPENNYNTTPPMLDSDGSFF
LYSKLTVDKSRWQQGNIFSCSVMHEALHNRFTQKSLSLSPGK|GLGGL|M
HGDTPTLHEYMLDLQPETTDLYGYGQLNDSSEEEDEIDGPAGQAEPDRAH
YNIVTFCCKCDSTLRLCVQSTHVDIRTLEDLLMGTLGIVCPICSQKP|GG -continued
GSSGGGSG|PSKPSFQEFVDWENVSPELNSTDQPFLGGGGSREGVELCPG
NKYEMRRHGTTHSLVIHDGGGGSSHCHWNDLAVIPAGVVHNWDFEPRKVS
GGGGSGRGHLLGRLAAIVGKQVLLGRKVVWRGGGGSFRRKAFLHWYTGEA
MDEMEFTEAESNMGGGGSVVDRNPQFLDPVLAYLMKGLCEKPLASGGGGS
SSPDEVALVEGVQSLGFTYLRLKDNYMGGGGSEFKHIKAFDRTFANNPGP
MVVFATPGMGGGGSSTANYNTSHLNNDVWQIFENPVDWKEKGGGGSDSGS
PFPAAVILRDALHMARGLKYLHQ Amino acid sequence of VB4004 = VB10.NEO
B16-III = B16 pepM1-M3, 5 aa linker
SEQ ID NO: 33
MQVSTAALAVLLCTMALCNQVLS|APLAADTPTACCFSYTSRQIPQNFIA
DYFETSSQCSKPSVIFLTKRGRQVCADPSEEWVQKYVSDLELSA|ELKTP
LGDTTHTIEPKSCDTPPPCPRCP|GGGSSGGGSG|GQPREPQVYTLPPSR
EEMTKNQVSLTCLVKGFYPSDIAVEWESSGQPENNYNTTPPMLDSDGSFF
LYSKLTVDKSRWQQGNIFSCSVMHEALHNRFTQKSLSLSPGK|GLGGL|M
HGDTPTLHEYMLDLQPETTDLYGYGQLNDSSEEEDEIDGPAGQAEPDRAH
YNIVTFCCKCDSTLRLCVQSTHVDIRTLEDLLMGTLGIVCPICSQKP|GG
GSSGGGSG|PSKPSFQEFVDWENVSPELNSTDQPFLGGGGSREGVELCPG
NKYEMRRHGTTHSLVIHDGGGGSSHCHWNDLAVIPAGVVHNWDFEPRKVS Signal peptide
SEQ ID NO: 34
MNFGLRLIFLVLTLKGVQC Signal peptide
SEQ ID NO: 35
MDAMKRGLCCVLLLCGAVFVSP B16-F10 mutated epitope, B16-pepM11,
amino acid sequence
SEQ ID NO: 36
ANFESGKHKYRQTAMFTATMPPAVERL Amino acid sequence of VB4011 = VB10.NEO
B16-X = B16 pepM1-M10, 10 aa linker
SEQ ID NO: 37
MQVSTAALAVLLCTMALCNQVLS|APLAADTPTACCFSYTSRQIPQNFIA
DYFETSSQCSKPSVIFLTKRGRQVCADPSEEWVQKYVSDLELSA|ELKTP
LGDTTHTIEPKSCDTPPPCPRCP|GGGSSGGGSG|GQPREPQVYTLPPSR
EEMTKNQVSLTCLVKGFYPSDIAVEWESSGQPENNYNTTPPMLDSDGSFF
LYSKLTVDKSRWQQGNIFSCSVMHEALHNRFTQKSLSLSPGK|GLGGL|M
HGDTPTLHEYMLDLQPETTDLYGYGQLNDSSEEEDEIDGPAGQAEPDRAH
YNIVTFCCKCDSTLRLCVQSTHVDIRTLEDLLMGTLGIVCPICSQKP|GG
GSSGGGSG|PSKPSFQEFVDWENVSPELNSTDQPFLGGGGSGGGGSREGV
ELCPGNKYEMRRHGTTHSLVIHDGGGGSGGGGSSHCWHNDLAVIPAGVVH
NWDFEPRKVSGGGGSGGGGSGRGHLLGRLAAIVGKQVLLGRKVVVVR**GGG
GSGGGGSFRRKAFLHWYTGEAMDEMEFTEAESNMGGGGSGGGGS**VVDRNP
QFLDPVLAYLMKGLCEKPLASGGGGSGGGGSSSPDEVALVEGVQSLGFTY
LRLKDNYMGGGGSGGGGSEFKHIKAFDRTFANNPGPMVVFATPGM**GGGGS
GGGGSSTANYNTSHLNNDVWQIFENPVDWKEKGGGGSGGGGS**DSGSPFPA
AVILRDALHMARGLKYLHQ Amino acid sequence of VB4012 = VB10.NEO
B16-III = B16 pepM1-M3, 10 aa linker
SEQ ID NO: 38
MQVSTAALAVLLCTMALCNQVLS|APLAADTPTACCFSYTSRQIPQNFIA
DYFETSSQCSKPSVIFLTKRGRQVCADPSEEWVQKYVSDLELSA|ELKTP
LGDTTHTIEPKSCDTPPPCPRCP|GGGSSGGGSG|GQPREPQVYTLPPSR
EEMTKNQVSLTCLVKGFYPSDIAVEWESSGQPENNYNTTPPMLDSDGSFF
LYSKLTVDKSRWQQGNIFSCSVMHEALHNRFTQKSLSLSPGK|GLGGL|M
HGDTPTLHEYMLDLQPETTDLYGYGQLNDSSEEEDEIDGPAGQAEPDRAH
YNIVTFCCKCDSTLRLCVQSTHVDIRTLEDLLMGTLGIVCPICSQKP|GG
GSSGGGSG|PSKPSFQEFVDWENVSPELNSTDQPFLGGGGSGGGGSREGV
ELCPGNKYEMRRHGTTHSLVIHDGGGGSGGGGSSHCWHNDLAVIPAGVVH
NWDFEPRKVS Amino acid sequence of VB4014 = VB10.NEO
B16-X = B16 hydrophobic core, (pepM9 + M5 + M1 +
M4 + M6 + M8 + M10 + M3 + M7 + M2), 5 aa linker
SEQ ID NO: 39
MQVSTAALAVLLCTMALCNQVLS|APLAADTPTACCFSYTSRQIPQNFIA
DYFETSSQCSKPSVIFLTKRGRQVCADPSEEWVQKYVSDLELSA|ELKTP
LGDTTHTIEPKSCDTPPPCPRCP|GGGSSGGGSG|GQPREPQVYTLPPSR
EEMTKNQVSLTCLVKGFYPSDIAVEWESSGQPENNYNTTPPMLDSDGSFF
LYSKLTVDKSRWQQGNIFSCSVMHEALHNRFTQKSLSLSPGK|GLGGL|M
HGDTPTLHEYMLDLQPETTDLYGYGQLNDSSEEEDEIDGPAGQAEPDRAH
YNIVTFCCKCDSTLRLCVQSTHVDIRTLEDLLMGTLGIVCPICSQKP|GG
GSSGGGSG|STANYNTSHLNNDVWQIFENPVDWKEKGGGGSFRRKAFLHW
YTGEAMDEMEFTEAESNMGGGGSPSKPSFQEFVDWENVSPELNSTDQPFL
GGGGSGRGHLLGRLAAIVGKQVLLGRKVVVVRGGGGSVVDRNPQFLDPVL
AYLMKGLCEKPLASGGGGSEFKHIKAFDRTFANNPGPMVVFATPGM**GGGG
SDSGSPFPAAVILRDALHMARGLKYLHQGGGGS**SHCWHNDLAVIPAGVVH
NWDFEPRKVSGGGGSSSPDEVALVEGVQSLGFTYLRLKDNYMGGGGSREG
VELCPGNKYEMRRHGTTHSLVIHD Amino acid sequence of VB4015 = VB10.NEO
B16-III = B16 pepM1-M8-M3, 5 aa linker
SEQ ID NO: 40
MQVSTAALAVLLCTMALCNQVLS|APLAADTPTACCFSYTSRQIPQNFIA
DYFETSSQCSKPSVIFLTKRGRQVCADPSEEWVQKYVSDLELSA|ELKTP
LGDTTHTIEPKSCDTPPPCPRCP|GGGSSGGGSG|GQPREPQVYTLPPSR
EEMTKNQVSLTCLVKGFYPSDIAVEWESSGQPENNYNTTPPMLDSDGSFF
LYSKLTVDKSRWQQGNIFSCSVMHEALHNRFTQKSLSLSPGK|GLGGL|M
HGDTPTLHEYMLDLQPETTDLYGYGQLNDSSEEEDEIDGPAGQAEPDRAH
YNIVTFCCKCDSTLRLCVQSTHVDIRTLEDLLMGTLGIVCPICSQKP|GG
GSSGGGSG|PSKPSFQEFVDWENVSPELNSTDQPFLGGGGSEFKHIKAFD
RTFANNPGPMVVFATPGMGGGGSSHCWHNDLAVIPAGVVHNWDFEPRKVS -continued Amino acid sequence of VB4016 = VB10.NEO
B16-III = B16 pepM1-M3-M2, 5 aa linker
SEQ ID NO: 41
MQVSTAALAVLLCTMALCNQVLS|APLAADTPTACCFSYTSRQIPQNFIA
DYFETSSQCSKPSVIFLTKRGRQVCADPSEEWVQKYVSDLELSA|ELKTP
LGDTTHTIEPKSCDTPPPCPRCP|GGGSSGGGSG|GQPREPQVYTLPPSR
EEMTKNQVSLTCLVKGFYPSDIAVEWESSGQPENNYNTTPPMLDSDGSFF
LYSKLTVDKSRWQQGNIFSCSVMHEALHNRFTQKSLSLSPGK|GLGGL|M
HGDTPTLHEYMLDLQPETTDLYGYGQLNDSSEEEDEIDGPAGQAEPDRAH
YNIVTFCCKCDSTLRLCVQSTHVDIRTLEDLLMGTLGIVCPICSQKP|GG
GSSGGGSG|PSKPSFQEFVDWENVSPELNSTDQPFLGGGGSSHCHWNDLA
VIPAGVVHNWDFEPRKVSGGGGSREGVELCPGNKYEMRRHGTTHSLVIHD Amino acid sequence of VB4017 = VB10.NEO
B16-X = B16 pepM1-M4 + M11 + M6-M10,
5 aa linker
SEQ ID NO: 42
MQVSTAALAVLLCTMALCNQVLS|APLAADTPTACCFSYTSRQIPQNFIA
DYFETSSQCSKPSVIFLTKRGRQVCADPSEEWVQKYVSDLELSA|ELKTP
LGDTTHTIEPKSCDTPPPCPRCP|GGGSSGGGSG|GQPREPQVYTLPPSR
EEMTKNQVSLTCLVKGFYPSDIAVEWESSGQPENNYNTTPPMLDSDGSFF
LYSKLTVDKSRWQQGNIFSCSVMHEALHNRFTQKSLSLSPGK|GLGGL|M
HGDTPTLHEYMLDLQPETTDLYGYGQLNDSSEEEDEIDGPAGQAEPDRAH
YNIVTFCCKCDSTLRLCVQSTHVDIRTLEDLLMGTLGIVCPICSQKP|GG
GSSGGGSG|PSKPSFQEFVDWENVSPELNSTDQPFLGGGGSREGVELCPG
NKYEMRRHGTTHSLVIHDGGGGSSHCHWNDLAVIPAGVVHNWDFEPRKVS
GGGGSGRGHLLGRLAAIVGKQVLLGRKVVVVRGGGGSANFESGKHKYRQT
AMFTATMPPAVERLGGGGSVVDRNPQFLDPVLAYLMKGLCEKPLAS**GGGG
SSSPDEVALVEGVQSLGFTYLRLKDNYMGGGGS**EFKHIKAFDRTFANNPG
PMVVFATPGMGGGGSSTANYNTSHLNNDVWQIFENPVDWKEKGGGGSDSG
SPFPAAVILRDALHMARGLKYLHQ Amino acid sequence of VB4018 = VB10.NEO
B16-XX = B16 pepM1-M4 + M11 + M6-M10 x 2,
5 aa linker
SEQ ID NO: 43
MQVSTAALAVLLCTMALCNQVLS|APLAADTPTACCFSYTSRQIPQNFIA
DYFETSSQCSKPSVIFLTKRGRQVCADPSEEWVQKYVSDLELSA|ELKTP
LGDTTHTIEPKSCDTPPPCPRCP|GGGSSGGGSG|GQPREPQVYTLPPSR
EEMTKNQVSLTCLVKGFYPSDIAVEWESSGQPENNYNTTPPMLDSDGSFF
LYSKLTVDKSRWQQGNIFSCSVMHEALHNRFTQKSLSLSPGK|GLGGL|M
HGDTPTLHEYMLDLQPETTDLYGYGQLNDSSEEEDEIDGPAGQAEPDRAH
YNIVTFCCKCDSTLRLCVQSTHVDIRTLEDLLMGTLGIVCPICSQKP|GG
GSSGGGSG|PSKPSFQEFVDWENVSPELNSTDQPFLGGGGSREGVELCPG
NKYEMRRHGTTHSLVIHDGGGGSSHCHWNDLAVIPAGVVHNWDFEPRKVS
GGGGSGRGHLLGRLAAIVGKQVLLGRKVVWRGGGGSANFESGKHKYRQTA
MFTATMPPAVERLGGGGSVVDRNPQFLDPVLAYLMKGLCEKPLASGGGGS
ASSPDEVALVEGVQSLGFTYLRLKDNYMGGGGSEFKHIKAFDRTFANNPGP
MVVFATPGMGGGGSSTANYNTSHLNNDVWQIFENPVDWKEKGGGGSDSGS
PFPAAVILRDALHMARGLKYLHQGGGGSPSKPSFQEFVDWENVSPELNST
DQPFLGGGGSREGVELCPGNKYEMRRHGTTHSLVIHDGGGGSSHCHWNDL
AVIPAGVVHNWDFEPRKVSGGGGSGRGHLLGRLAAIVGKQVLLGRKVVVV
RGGGGSANFESGKHKYRQTAMFTATMPPAVERLGGGGSVVDRNPQFLDPV
LAYLMKGLCEKPLASGGGGSSSPDEVALVEGVQSLGFTYLRLKDNYM**GGG
GSEFKHIKAFDRTFANNPGPMVVFATPGMGGGGS**STANYNTSHLNNDVWQ
IFENPVDWKEKGGGGSDSGSPFPAAVILRDALHMARGLKYLHQ Amino acid sequence of VB4019 = VB10.NEO
B16-Vx2 = B16 pepM3-M4-M7-M9-M10 x 2,
5 aa linker
SEQ ID NO: 44
MQVSTAALAVLLCTMALCNQVLS|APLAADTPTACCFSYTSRQIPQNFIA
DYFETSSQCSKPSVIFLTKRGRQVCADPSEEWVQKYVSDLELSA|ELKTP
LGDTTHTIEPKSCDTPPPCPRCP|GGGSSGGGSG|GQPREPQVYTLPPSR
EEMTKNQVSLTCLVKGFYPSDIAVEWESSGQPENNYNTTPPMLDSDGSFF
LYSKLTVDKSRWQQGNIFSCSVMHEALHNRFTQKSLSLSPGK|GLGGL|M
HGDTPTLHEYMLDLQPETTDLYGYGQLNDSSEEEDEIDGPAGQAEPDRAH
YNIVTFCCKCDSTLRLCVQSTHVDIRTLEDLLMGTLGIVCPICSQKP|GG
GSSGGGSG|SHCHWNDLAVIPAGVVHNWDFEPRKVSGGGGSGRGHLLGRL
AAIVGKQVLLGRKVWRGGGGSSSPDEVALVEGVQSLGFTYLRLKDNYM**G
GGGSSTANYNTSHLNNDVWQIFENPVDWKEKGGGGS**DSGSPFPAAVILRD
ALHMARGLKYLHQGGGGSSHCHWNDLAVIPAGVVHNWDFEPRKVSGGGGS
GRGHLLGRLAAIVGKQVLLGRKVVVVRGGGGSSSPDEVALVEGVQSLGFT
YLRLKDNYMGGGGSSTANYNTSHLNNDVWQIFENPVDWKEKGGGGSDSGS
PFPAAVILRDALHMARGLKYLHQ Amino acid sequence of VB4021 = VB10.NEO
B16-Vx4 = B16 pepM3-M4-M7-M9-M10 x 4,
5 aa linker
SEQ ID NO: 45
MQVSTAALAVLLCTMALCNQVLS|APLAADTPTACCFSYTSRQIPQNFIA
DYFETSSQCSKPSVIFLTKRGRQVCADPSEEWVQKYVSDLELSA|ELKTP
LGDTTHTIEPKSCDTPPPCPRCP|GGGSSGGGSG|GQPREPQVYTLPPSR
EEMTKNQVSLTCLVKGFYPSDIAVEWESSGQPENNYNTTPPMLDSDGSFF
LYSKLTVDKSRWQQGNIFSCSVMHEALHNRFTQKSLSLSPGK|GLGGL|M
HGDTPTLHEYMLDLQPETTDLYGYGQLNDSSEEEDEIDGPAGQAEPDRAH
YNIVTFCCKCDSTLRLCVQSTHVDIRTLEDLLMGTLGIVCPICSQKP|GG
GSSGGGSG|SHCHWNDLAVIPAGVVHNWDFEPRKVSGGGGSGRGHLLGRL
AAIVGKQVLLGRKVWRGGGGSSSPDEVALVEGVQSLGFTYLRLKDNYM**G
GGGSSTANYNTSHLNNDVWQIFENPVDWKEKGGGGS**DSGSPFPAAVILRD
ALHMARGLKYLHQGGGGSSHCHWNDLAVIPAGVVHNWDFEPRKVSGGGGS
GRGHLLGRLAAIVGKQVLLGRKVVWRGGGGSSSPDEVALVEGVQSLGFTY
LRLKDNYMGGGGSSTANYNTSHLNNDVWQIFENPVDWKEKGGGGSDSGSP
FPAAVILRDALHMARGLKYLHQGGGGSSHCHWNDLAVIPAGVVHNWDFEP
RKVSGGGGSGRGHLLGRLAAIVGKQVLLGRKVVVVRGGGGSSSPDEVALV -continued EGVQSLGFTYLRLKDNYMGGGGSSTANYNTSHLNNDVWQIFENPVDWKEK
GGGGSDSGSPFPAAVILRDALHMARGLKYLHQ Amino acid sequence of VB4024 = VB10.NEO
B16-XV = B16 pepM1-M15, 10 aa linker
SEQ ID NO: 46
MQVSTAALAVLLCTMALCNQVLS|APLAADTPTACCFSYTSRQIPQNFIA
DYFETSSQCSKPSVIFLTKRGRQVCADPSEEWVQKYVSDLELSA|ELKTP
LGDTTHTIEPKSCDTPPPCPRCP|GGGSSGGGSG|GQPREPQVYTLPPSR
EEMTKNQVSLTCLVKGFYPSDIAVEWESSGQPENNYNTTPPMLDSDGSFF
LYSKLTVDKSRWQQGNIFSCSVMHEALHNRFTQKSLSLSPGK|GLGGL|M
HGDTPTLHEYMLDLQPETTDLYGYGQLNDSSEEEDEIDGPAGQAEPDRAH
YNIVTFCCKCDSTLRLCVQSTHVDIRTLEDLLMGTLGIVCPICSQKP|GG
GSSGGGSG|PSKPSFQEFVDWENVSPELNSTDQPFLGGGGSGGGGSREGV
ELCPGNKYEMRRHGTTHSLVIHDGGGGSGGGGSSHCHWNDLAVIPAGVVH
NWDFEPRKVSGGGGSGGGGSGRGHLLGRLAAIVGKQVLLGRKVVVVR**GGG
GSGGGGSFRRKAFLHWYTGEAMDEMEFTEAESNMGGGGSGGGGS**VVDRNP
QFLDPVLAYLMKGLCEKPLASGGGGSGGGGSSPDEVALVEGVQSLGFTY
LRLKDNYMGGGGSGGGGSEFKHIKAFDRTFANNPGPMVVFATPGM**GGGGS
GGGGSSTANYNTSHLNNDVWQIFENPVDWKEKGGGGSGGGGS**DSGSPFPA
AVILRDALHMARGLKYLHQGGGGSGGGGSANFESGKHKYRQTAMFTATMP
PAVERLGGGGSGGGGSNHSGLVTFQAFIDVMSRETTDTDTADQ**GGGGSGG
GGSCGTAFFINFIAIYHHASRAIPFGTMVAGGGGSGGGGS**FVVKAYLPVN
ESFAFTADLRSNTGGQAGGGGSGGGGSTPPPEEAMPFEFNGPAQGDHSQP
PLQV Amino acid sequence of VB4025 = VB10.NEO
B16-XX = B16 pepM1-M20, 10 aa linker
SEQ ID NO: 47
MQVSTAALAVLLCTMALCNQVLS|APLAADTPTACCFSYTSRQIPQNFIA
DYFETSSQCSKPSVIFLTKRGRQVCADPSEEWVQKYVSDLELSA|ELKTP
LGDTTHTIEPKSCDTPPPCPRCP|GGGSSGGGSG|GQPREPQVYTLPPSR
EEMTKNQVSLTCLVKGFYPSDIAVEWESSGQPENNYNTTPPMLDSDGSFF
LYSKLTVDKSRWQQGNIFSCSVMHEALHNRFTQKSLSLSPGK|GLGGL|M
HGDTPTLHEYMLDLQPETTDLYGYGQLNDSSEEEDEIDGPAGQAEPDRAH
YNIVTFCCKCDSTLRLCVQSTHVDIRTLEDLLMGTLGIVCPICSQKP|GG
GSSGGGSG|PSKPSFQEFVDWENVSPELNSTDQPFLGGGGSGGGGSREGV
ELCPGNKYEMRRHGTTHSLVIHDGGGGSGGGGSSHCHWNDLAVIPAGVVH
NWDFEPRKVSGGGGSGGGGSGRGHLLGRLAAIVGKQVLLGRKVWVVR**GGG
GSGGGGSFRRKAFLHWYTGEAMDEMEFTEAESNMGGGGSGGGGS**VVDRNP
QFLDPVLAYLMKGLCEKPLASGGGGSGGGGSSPDEVALVEGVQSLGFTY
LRLKDNYMGGGGSGGGGSEFKHIKAFDRTFANNPGPMVVFATPGM**GGGGS
GGGGSSTANYNTSHLNNDVWQIFENPVDWKEKGGGGSGGGGS**DSGSPFPA
AVILRDALHMARGLKYLHQGGGGSGGGGSANFESGKHKYRQTAMFTATMP
PAVERLGGGGSGGGGSNHSGLVTFQAFIDVMSRETTDTDTADQ**GGGGSGG
GGSCGTAFFINFIAIYHHASRAIPFGTMVAGGGGSGGGGS**FVVKAYLPVN
ESFAFTADLRSNTGGQAGGGGSGGGGSTPPPEEAMPFEFNGPAQGDHSQP
PLQVGGGGSGGGGSPKPDFSQLQRNILPSNPRVTRFHINWD**GGGGSGGGG
SIPSGTTILNCFHDVLSGKLSGGSPGVPGGGGSGGGGSGFSQPLRRLVLH
VVSAAQAERLARAEEGGGGSGGGGSECRITSNFVIPSEYWVEEKEEKQKL
IQGGGGSGGGGSNIEGIDKLTQLKKPFLVNNKINKIENI Amino acid sequence of VB4026 = VB10.NEO
CT26-XV = CT26 pepM1-M15,10 aa linker
SEQ ID NO: 48
MQVSTAALAVLLCTMALCNQVLS|APLAADTPTACCFSYTSRQIPQNFIA
DYFETSSQCSKPSVIFLTKRGRQVCADPSEEWVQKYVSDLELSA|ELKTP
LGDTTHTIEPKSCDTPPPCPRCP|GGGSSGGGSG|GQPREPQVYTLPPSR
EEMTKNQVSLTCLVKGFYPSDIAVEWESSGQPENNYNTTPPMLDSDGSFF
LYSKLTVDKSRWQQGNIFSCSVMHEALHNRFTQKSLSLSPGK|GLGGL|M
HGDTPTLHEYMLDLQPETTDLYGYGQLNDSSEEEDEIDGPAGQAEPDRAH
YNIVTFCCKCDSTLRLCVQSTHVDIRTLEDLLMGTLGIVCPICSQKP|GG
GSSGGGSG|VILPQAPSGPSYATYLQPAQAQMLTPPGGGGSGGGGSLHSG
QNHLKEMAISVLEARACAAAGQSGGGGSGGGGSPLLPFYPPDEALEIGLE
LNSSALPPTEGGGGSGGGGSAGTQCEYWASRALDSEHSIGSMIQLPQ**GGG
GSGGGGSAAYKGHHYPGPGNYFWKCLFMSGLSEVGGGGSGGGGS**DTLSAM
SNPRAMQVLLQIQQGLQTLATGGGGSGGGGSDKPLRRNNSYTSYIMAICG
MPLDSFRAGGGGSGGGGSEVIQTSKYYMRDVIAIESAWLLELAPH**GGGGS
GGGGSGYISRVTAGKDSYIALVDKNIMGYIASGGGGSGGGGS**EHIHRAGG
LFVADAIQVGFGRIGKHFWGGGGSGGGGSQAIVRGCSMPGPWRSGRLLVS
RRWSVEGGGGSGGGGSDGQLELLAQGALDNALSSMGALHALRP**GGGGSGG
GGSSHDSRKSTSFMSVNPSKEIKIVSAVRRGGGGSGGGGS**HTPSSYIETL
PKAIKRRINALKQLQVRGGGGSGGGGSMKAFIFKYSAKTGFTKLIDASRV
SETE Amino acid sequence of VB4027 = VB10.NEO
CT26-XX = CT26 pepM1-M20,10 aa linker
SEQ ID NO: 49
MQVSTAALAVLLCTMALCNQVLS|APLAADTPTACCFSYTSRQIPQNFIA
DYFETSSQCSKPSVIFLTKRGRQVCADPSEEWVQKYVSDLELSA|ELKTP
LGDTTHTIEPKSCDTPPPCPRCP|GGGSSGGGSG|GQPREPQVYTLPPSR
EEMTKNQVSLTCLVKGFYPSDIAVEWESSGQPENNYNTTPPMLDSDGSFF
LYSKLTVDKSRWQQGNIFSCSVMHEALHNRFTQKSLSLSPGK|GLGGL|M
HGDTPTLHEYMLDLQPETTDLYGYGQLNDSSEEEDEIDGPAGQAEPDRAH
YNIVTFCCKCDSTLRLCVQSTHVDIRTLEDLLMGTLGIVCPICSQKP|GG
GSSGGGSG|VILPQAPSGPSYATYLQPAQAQMLTPPGGGGSGGGGSLHSG
QNHLKEMAISVLEARACAAAGQSGGGGSGGGGSPLLPFYPPDEALEIGLE
LNSSALPPTEGGGGSGGGGSAGTQCEYWASRALDSEHSIGSMIQLPQ**GGG
GSGGGGSAAYKGHHYPGPGNYFWKCLFMSGLSEVGGGGSGGGGS**DTLSAM
SNPRAMQVLLQIQQGLQTLATGGGGSGGGGSDKPLRRNNSYTSYIMAICG
MPLDSFRAGGGGSGGGGSEVIQTSKYYMRDVIAIESAWLLELAPH**GGGGS -continued

```
GGGGSGYISRVTAGKDSYIALVDKNIMGYIASGGGGSGGGGSEHIHRAGG

LFVADAIQVGFGRIGKHFWGGGGSGGGGSQAIVRGCSMPGPWRSGRLLVS

RRWSVEGGGGSGGGGSDGQLELLAQGALDNALSSMGALHALRPGGGGSG

GGSSHDSRKSTSFMSVNPSKEIKIVSAVRRGGGGSGGGGSHTPSSYIETL

PKAIKRRINALKQLQVRGGGGSGGGGSMKAFIFKYSAKTGFTKLIDASRV

SETEGGGGSGGGGSEGDPCLRSSDCIDEFCCARHFWTKICKGGGGSGGGG

SWKGGPVKIDPLALMQAIERYLVVRGYGGGGSGGGGSVTSIPSVSNALN

WKEFSFIQSTLGYVAGGGGSGGGGSYRGANLHLEETLAGFWARLLERLFK

QLGGGGSGGGGSKTTLSHTQDSSQSLQSSSDSSKSSRCS
```

CT26 mutated epitope, CT26-PepM11,
amino acid sequence
SEQ ID NO: 50
QAIVRGCSMPGPWRSGRLLVSRRWSVE CT26 mutated epitope, CT26-PepM12,
amino acid sequence
SEQ ID NO: 51
DGQLELLAQGALDNALSSMGALHALRP CT26 mutated epitope, CT26-PepM13,
amino acid sequence
SEQ ID NO: 52
SHDSRKSTSFMSVNPSKEIKIVSAVRR CT26 mutated epitope, CT26-PepM14,
amino acid sequence
SEQ ID NO: 53
HTPSSYIETLPKAIKRRINALKQLQVR CT26 mutated epitope, CT26-PepM15,
amino acid sequence
SEQ ID NO: 54
MKAFIFKYSAKTGFTKLIDASRVSETE CT26 mutated epitope, CT26-PepM16,
amino acid sequence
SEQ ID NO: 55
EGDPCLRSSDCIDEFCCARHFWTKICK CT26 mutated epitope, CT26-PepM17,
amino acid sequence
SEQ ID NO: 56
WKGGPVKIDPLALMQAIERYLVVRGYG CT26 mutated epitope, CT26-PepM18,
amino acid sequence
SEQ ID NO: 57
VTSIPSVSNALNWKEFSFIQSTLGYVA CT26 mutated epitope, CT26-PepM19,
amino acid sequence
SEQ ID NO: 58
YRGANLHLEETLAGFWARLLERLFKQL CT26 mutated epitope, CT26-PepM20,
amino acid sequence
SEQ ID NO: 59
KTTLSHTQDSSQSLQSSSDSSKSSRCS B16-F10 mutated epitope, B16-PepM12,
amino acid sequence
SEQ ID NO: 60
NHSGLVTFQAFIDVMSRETTDTDTADQ B16-F10 mutated epitope, B16-PepM13,
amino acid sequence
SEQ ID NO: 61
CGTAFFINFIAIYHHASRAIPFGTMVA B16-F10 mutated epitope, B16-PepM14,
amino acid sequence
SEQ ID NO: 62
FVVKAYLPVNESFAFTADLRSNTGGQA B16-F10 mutated epitope, B16-PepM15,
amino acid sequence
SEQ ID NO: 63
TPPPEEAMPFEFNGPAQGDHSQPPLQV B16-F10 mutated epitope, B16-PepM16,
amino acid sequence
SEQ ID NO: 64
PKPDFSQLQRNILPSNPRVTRFHINWD B16-F10 mutated epitope, B16-PepM17,
amino acid sequence
SEQ ID NO: 65
IPSGTTILNCFHDVLSGKLSGGSPGVP B16-F10 mutated epitope, B16-PepM18,
amino acid sequence
SEQ ID NO: 66
GFSQPLRRLVLHVVSAAQAERLARAEE B16-F10 mutated epitope, B16-PepM19,
amino acid sequence
SEQ ID NO: 67
ECRITSNFVIPSEYWVEEKEEKQKLIQ B16-F10 mutated epitope, B16-PepM20,
amino acid sequence
SEQ ID NO: 68
NIEGIDKLTQLKKPFLVNNKINKIENI Linker:
SEQ ID NO: 69
GGGSS.

Linker:
SEQ ID NO: 70
GGGSG.

Linker:
SEQ ID NO: 71
GGGGS.

Linker:
SEQ ID NO: 72
LGGGS.

Linker:
SEQ ID NO: 73
GLGGS.

Linker:
SEQ ID NO: 74
GGLGS.

Linker:
SEQ ID NO: 75
GGGLS.

Linker:
SEQ ID NO: 76
GGGGL.

Linker:
SEQ ID NO: 77
LGGSG.

Linker:
SEQ ID NO: 78
GLGSG.

Linker:
SEQ ID NO: 79
GGLSG.

| Linker: GGGLG. | SEQ ID NO: 80 |
| --- | --- |
| Linker: GGGSL. | SEQ ID NO: 81 |
| Linker: LGGSS. | SEQ ID NO: 82 |
| Linker: GLGSS. | SEQ ID NO: 83 |
| Linker: GGLSS. | SEQ ID NO: 84 |
| Linker: GGGLS. | SEQ ID NO: 85 |
| Linker: GGGSL. | SEQ ID NO: 86 |
| Linker: LGLGS. | SEQ ID NO: 87 |
| Linker: GLGLS. | SEQ ID NO: 88 |
| Linker: GLLGS. | SEQ ID NO: 89 |
| Linker: LGGLS. | SEQ ID NO: 90 |
| Linker: GLGGL. | SEQ ID NO: 91 |
| Linker: LGLSG. | SEQ ID NO: 92 |
| Linker: GLLSG. | SEQ ID NO: 93 |
| Linker: GGLSL. | SEQ ID NO: 94 |
| Linker: GGLLG. | SEQ ID NO: 95 |
| Linker: GLGSL. | SEQ ID NO: 96 |
| Linker: LGLSS. | SEQ ID NO: 97 |
| Linker: GLGLS. | SEQ ID NO: 98 |
| Linker: GGLLS. | SEQ ID NO: 99 |
| Linker: GLGSL. | SEQ ID NO: 100 |
| Linker: GLGSL. | SEQ ID NO: 101 |
| Linker: LGGGSGGGGS. | SEQ ID NO: 102 |
| Linker: GLGGSGGGGS. | SEQ ID NO: 103 |
| Linker: GGLGSGGGGS. | SEQ ID NO: 104 |
| Linker: GGGLSGGGGS. | SEQ ID NO: 105 |
| Linker: GGGGLGGGGS. | SEQ ID NO: 106 |
| Linker: LGGSGGGGSG. | SEQ ID NO: 107 |
| Linker: GLGSGGGGSG. | SEQ ID NO: 108 |
| Linker: GGLSGGGGSG. | SEQ ID NO: 109 |
| Linker: GGGLGGGGSG. | SEQ ID NO: 110 |
| Linker: GGGSLGGGSG. | SEQ ID NO: 111 |
| Linker: GGGSLGGGSG. | SEQ ID NO: 112 |
| Linker: GLGSSGGGSS. | SEQ ID NO: 113 |
| Linker: GGLSSGGGSS. | SEQ ID NO: 114 |
| Linker: GGGLSGGGSS. | SEQ ID NO: 115 |
| Linker: GGGSLGGGSS. | SEQ ID NO: 116 |
| Linker: LGGGSLGGGS. | SEQ ID NO: 117 |
| Linker: GLGGSGLGGS. | SEQ ID NO: 118 |
| Linker: GGLGSGGLGS. | SEQ ID NO: 119 |

-continued

Linker:
GGGLSGGGLS.
SEQ ID NO: 120

Linker:
GGGGLGGGGL.
SEQ ID NO: 121

Linker:
LGGSGLGGSG.
SEQ ID NO: 122

Linker:
GLGSGGLGSG.
SEQ ID NO: 123

Linker:
GGLSGGGLSG.
SEQ ID NO: 124

Linker:
GGGLGGGGLG.
SEQ ID NO: 125

Linker:
GGGSLGGGSL.
SEQ ID NO: 126

-continued

Linker:
GGGSLGGGSL.
SEQ ID NO: 126

Linker:
LGGSSLGGSS.
SEQ ID NO: 127

Linker:
GLGSSGLGSS.
SEQ ID NO: 128

Linker:
GGLSSGGLSS.
SEQ ID NO: 129

Linker:
GGGLSGGGLS.
SEQ ID NO: 130

Linker:
GGGSLGGGSL.
SEQ ID NO: 131

---

The invention claimed is:

1. An anticancer neoepitope composition comprising:
a DNA polynucleotide comprising a nucleotide sequence encoding
a targeting unit comprising an amino acid sequence having at least 85% sequence identity to the amino acid sequence of SEQ ID NO: 1,
a dimerization unit comprising an amino acid sequence having at least 85% sequence identity to the amino acid sequences of SEQ ID NOs: 26-29,
a first linker, and
an antigenic unit, wherein said antigenic unit comprises n cancer neoepitope sequences and n−1 antigenic subunits, each subunit comprising a cancer neoepitope sequence and a second linker and wherein n is an integer of from 3 to 50.

2. The anticancer neoepitope composition according to claim 1, wherein the antigenic unit comprises one copy of each cancer neoepitope sequence.

3. The anticancer neoepitope composition according to claim 1, wherein the antigenic unit comprises at least two copies of at least one cancer neoepitope sequence.

4. The anticancer neoepitope composition according to claim 1, wherein each cancer neoepitope sequence has a length of from 7 to 30 amino acids.

5. The anticancer neoepitope composition according to claim 1, wherein each cancer neoepitope sequence has identical length.

6. The anticancer neoepitope composition according to claim 1, wherein the cancer neoepitope is positioned essentially in the middle of the cancer neoepitope sequence.

7. The anticancer neoepitope composition according to claim 1, wherein the antigenic subunits are in the order of more antigenic to less antigenic from the first linker.

8. The anticancer neoepitope composition according to claim 1, wherein the antigenic subunit(s) comprising the most hydrophobic cancer neoepitope sequences is/are substantially the middle of the antigenic unit and the antigenic subunit(s) comprising the most hydrophilic cancer neoepitope sequences is/are at the ends of the antigenic unit.

9. The anticancer neoepitope composition according to claim 1, wherein the second linker is a flexible linker.

10. The anticancer neoepitope composition according to claim 1, wherein the second linker is a Serine-Glycine linker.

11. The anticancer neoepitope composition according to claim 1, wherein the length of the antigenic unit is from about 300 amino acids to about 1000 amino acids.

12. The anticancer neoepitope composition according to claim 1, wherein the dimerization unit comprises or consists of the amino acid sequences of SEQ ID NOs: 26-29.

13. The anticancer neoepitope composition according to claim 1, wherein the targeting unit comprises or consists of the amino acid sequence of SEQ ID NO: 1.

14. The anticancer neoepitope composition according to claim 1, comprising a DNA polynucleotide comprising a nucleotide sequence encoding the amino acid sequences of SEQ ID NO: 1, SEQ ID NOs: 26-29 and SEQ ID NO: 25.

15. The anticancer neoepitope composition according to claim 1, wherein the cancer neoepitope sequence is from a cancer resulting in a tumor, such as a cancer having a high mutational load and/or a cancer selected from the group consisting of melanoma, lung cancer, breast cancer, prostate cancer and colon cancer.

16. The anticancer neoepitope composition according to claim 1, wherein n is an integer of from 10 to 20.

17. The anticancer neoepitope composition according to claim 14, wherein n is an integer of from 10 to 20.

18. The anticancer neoepitope composition according to claim 17, wherein the antigenic subunit(s) comprising the most hydrophobic cancer neoepitope sequences is/are substantially the middle of the antigenic unit and the antigenic subunit(s) comprising the most hydrophilic cancer neoepitope sequences is/are at the ends of the antigenic unit.

19. The anticancer neoepitope composition according to claim 1, wherein the DNA polynucleotide is comprised in a vector.

20. The anticancer neoepitope composition according to claim 14, wherein the DNA polynucleotide is comprised in a vector.

21. The anticancer neoepitope composition according to claim 17, wherein the DNA polynucleotide is comprised in a vector.

22. A method of treating a cancer in a patient, the method comprising administering to the patient the anticancer neoepitope composition as defined in claim 1.

* * * * *

SEQUENCE LISTING

<160> NUMBER OF SEQ ID NOS: 131

<210> SEQ ID NO 1
<211> LENGTH: 93
<212> TYPE: PRT
<213> ORGANISM: Homo sapiens

<400> SEQUENCE: 1

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala
                85                  90

<210> SEQ ID NO 2
<211> LENGTH: 726
<212> TYPE: DNA
<213> ORGANISM: Artificial Sequence
<220> FEATURE:
<223> OTHER INFORMATION: Vector

<400> SEQUENCE: 2
atgcaggtct ccactgctgc ccttgccgtc ctcctctgca ccatggctct ctgcaaccag     60
gtcctctctg caccacttgc tgctgacacg ccgaccgcct gctgcttcag ctacacctcc    120
cgacagattc cacagaattt catagctgac tactttgaga cgagcagcca gtgctccaag    180
cccagtgtca tcttcctaac caagagaggc cggcaggtct gtgctgaccc cagtgaggag    240
tgggtccaga aatacgtcag tgacctggag ctgagtgccg agctcaaaac cccacttggt    300
gacacaactc acacagagcc caaatcttgt gacacacctc cccgtgccc aaggtgccca    360 ggcggtggaa gcagcggagg tggaagtgga ggacagcccc gagaaccaca ggtgtacacc    420

```
ctgcccccat cccgggagga gatgaccaag aaccaggtca gcctgacctg cctggtcaaa    480
ggcttctacc ccagcgacat cgccgtggag tgggagagca gcgggcagcc ggagaacaac    540
tacaacacca cgcctcccat gctggactcc gacggctcct tcttcctcta cagcaagctc    600
accgtggaca gagcaggtg gcagcagggg aacatcttct catgctccgt gatgcatgag     660
gctctgcaca accgcttcac gcagaagagc ctctccctgt ctccgggtaa aggcctcggt    720
ggcctg                                                              726
```

<210> SEQ ID NO 3
<211> LENGTH: 243
<212> TYPE: PRT
<213> ORGANISM: Artificial Sequence
<220> FEATURE:
<223> OTHER INFORMATION: Homodimeric construct

<400> SEQUENCE: 3

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Ile Glu Pro Lys Ser Cys Asp
            100                 105                 110

Thr Pro Pro Pro Cys Pro Arg Cys Pro Gly Gly Gly Ser Ser Gly Gly
        115                 120                 125

Gly Ser Gly Gly Gln Pro Arg Glu Pro Gln Val Tyr Thr Leu Pro Pro
    130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Ser Gly
                165                 170                 175

Gln Pro Glu Asn Asn Tyr Asn Thr Thr Pro Pro Met Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Ile Phe Ser Cys Ser Val Met His Glu Ala Leu His
    210                 215                 220

Asn Arg Phe Thr Gln Lys Ser Leu Ser Leu Ser Pro Gly Lys Gly Leu
225                 230                 235                 240

Gly Gly Leu
```

<210> SEQ ID NO 4
<211> LENGTH: 27
<212> TYPE: PRT
<213> ORGANISM: Mus musculus

<400> SEQUENCE: 4

```
Pro Ser Lys Pro Ser Phe Gln Glu Phe Val Asp Trp Glu Asn Val Ser
```

```
                1               5                  10                  15
Pro Glu Leu Asn Ser Thr Asp Gln Pro Phe Leu
            20                  25

<210> SEQ ID NO 5
<211> LENGTH: 27
<212> TYPE: PRT
<213> ORGANISM: Mus musculus

<400> SEQUENCE: 5

Arg Glu Gly Val Glu Leu Cys Pro Gly Asn Lys Tyr Glu Met Arg Arg
1               5                   10                  15

His Gly Thr Thr His Ser Leu Val Ile His Asp
            20                  25

<210> SEQ ID NO 6
<211> LENGTH: 27
<212> TYPE: PRT
<213> ORGANISM: Mus musculus

<400> SEQUENCE: 6

Ser His Cys His Trp Asn Asp Leu Ala Val Ile Pro Ala Gly Val Val
1               5                   10                  15

His Asn Trp Asp Phe Glu Pro Arg Lys Val Ser
            20                  25

<210> SEQ ID NO 7
<211> LENGTH: 27
<212> TYPE: PRT
<213> ORGANISM: Mus musculus

<400> SEQUENCE: 7

Gly Arg Gly His Leu Leu Gly Arg Leu Ala Ala Ile Val Gly Lys Gln
1               5                   10                  15

Val Leu Leu Gly Arg Lys Val Val Val Arg
            20                  25

<210> SEQ ID NO 8
<211> LENGTH: 27
<212> TYPE: PRT
<213> ORGANISM: Mus musculus

<400> SEQUENCE: 8

Phe Arg Arg Lys Ala Phe Leu His Trp Tyr Thr Gly Glu Ala Met Asp
1               5                   10                  15

Glu Met Glu Phe Thr Glu Ala Glu Ser Asn Met
            20                  25

<210> SEQ ID NO 9
<211> LENGTH: 27
<212> TYPE: PRT
<213> ORGANISM: Mus musculus

<400> SEQUENCE: 9

Val Val Asp Arg Asn Pro Gln Phe Leu Asp Pro Val Leu Ala Tyr Leu
1               5                   10                  15

Met Lys Gly Leu Cys Glu Lys Pro Leu Ala Ser
            20                  25

<210> SEQ ID NO 10
<211> LENGTH: 27
<212> TYPE: PRT
```

<213> ORGANISM: Mus musculus

<400> SEQUENCE: 10

Ser Ser Pro Asp Glu Val Ala Leu Val Glu Gly Val Gln Ser Leu Gly
1               5                   10                  15

Phe Thr Tyr Leu Arg Leu Lys Asp Asn Tyr Met
            20                  25

<210> SEQ ID NO 11
<211> LENGTH: 27
<212> TYPE: PRT
<213> ORGANISM: Mus musculus

<400> SEQUENCE: 11

Glu Phe Lys His Ile Lys Ala Phe Asp Arg Thr Phe Ala Asn Asn Pro
1               5                   10                  15

Gly Pro Met Val Val Phe Ala Thr Pro Gly Met
            20                  25

<210> SEQ ID NO 12
<211> LENGTH: 27
<212> TYPE: PRT
<213> ORGANISM: Mus musculus

<400> SEQUENCE: 12

Ser Thr Ala Asn Tyr Asn Thr Ser His Leu Asn Asn Asp Val Trp Gln
1               5                   10                  15

Ile Phe Glu Asn Pro Val Asp Trp Lys Glu Lys
            20                  25

<210> SEQ ID NO 13
<211> LENGTH: 27
<212> TYPE: PRT
<213> ORGANISM: Mus musculus

<400> SEQUENCE: 13

Asp Ser Gly Ser Pro Phe Pro Ala Ala Val Ile Leu Arg Asp Ala Leu
1               5                   10                  15

His Met Ala Arg Gly Leu Lys Tyr Leu His Gln
            20                  25

<210> SEQ ID NO 14
<211> LENGTH: 27
<212> TYPE: PRT
<213> ORGANISM: Mus musculus

<400> SEQUENCE: 14

Val Ile Leu Pro Gln Ala Pro Ser Gly Pro Ser Tyr Ala Thr Tyr Leu
1               5                   10                  15

Gln Pro Ala Gln Ala Gln Met Leu Thr Pro Pro
            20                  25

<210> SEQ ID NO 15
<211> LENGTH: 27
<212> TYPE: PRT
<213> ORGANISM: Mus musculus

<400> SEQUENCE: 15

Leu His Ser Gly Gln Asn His Leu Lys Glu Met Ala Ile Ser Val Leu
1               5                   10                  15

Glu Ala Arg Ala Cys Ala Ala Ala Gly Gln Ser
            20                  25

```
<210> SEQ ID NO 16
<211> LENGTH: 27
<212> TYPE: PRT
<213> ORGANISM: Mus musculus

<400> SEQUENCE: 16

Pro Leu Leu Pro Phe Tyr Pro Pro Asp Glu Ala Leu Glu Ile Gly Leu
1               5                   10                  15

Glu Leu Asn Ser Ser Ala Leu Pro Pro Thr Glu
            20                  25

<210> SEQ ID NO 17
<211> LENGTH: 27
<212> TYPE: PRT
<213> ORGANISM: Mus musculus

<400> SEQUENCE: 17

Ala Gly Thr Gln Cys Glu Tyr Trp Ala Ser Arg Ala Leu Asp Ser Glu
1               5                   10                  15

His Ser Ile Gly Ser Met Ile Gln Leu Pro Gln
            20                  25

<210> SEQ ID NO 18
<211> LENGTH: 27
<212> TYPE: PRT
<213> ORGANISM: Mus musculus

<400> SEQUENCE: 18

Ala Ala Tyr Lys Gly His His Tyr Pro Gly Pro Gly Asn Tyr Phe Trp
1               5                   10                  15

Lys Cys Leu Phe Met Ser Gly Leu Ser Glu Val
            20                  25

<210> SEQ ID NO 19
<211> LENGTH: 27
<212> TYPE: PRT
<213> ORGANISM: Mus musculus

<400> SEQUENCE: 19

Asp Thr Leu Ser Ala Met Ser Asn Pro Arg Ala Met Gln Val Leu Leu
1               5                   10                  15

Gln Ile Gln Gln Gly Leu Gln Thr Leu Ala Thr
            20                  25

<210> SEQ ID NO 20
<211> LENGTH: 27
<212> TYPE: PRT
<213> ORGANISM: Mus musculus

<400> SEQUENCE: 20

Asp Lys Pro Leu Arg Arg Asn Asn Ser Tyr Thr Ser Tyr Ile Met Ala
1               5                   10                  15

Ile Cys Gly Met Pro Leu Asp Ser Phe Arg Ala
            20                  25

<210> SEQ ID NO 21
<211> LENGTH: 27
<212> TYPE: PRT
<213> ORGANISM: Mus musculus

<400> SEQUENCE: 21
```

```
Glu Val Ile Gln Thr Ser Lys Tyr Tyr Met Arg Asp Val Ile Ala Ile
1               5                   10                  15

Glu Ser Ala Trp Leu Leu Glu Leu Ala Pro His
            20                  25
```

<210> SEQ ID NO 22
<211> LENGTH: 27
<212> TYPE: PRT
<213> ORGANISM: Mus musculus

<400> SEQUENCE: 22

```
Gly Tyr Ile Ser Arg Val Thr Ala Gly Lys Asp Ser Tyr Ile Ala Leu
1               5                   10                  15

Val Asp Lys Asn Ile Met Gly Tyr Ile Ala Ser
            20                  25
```

<210> SEQ ID NO 23
<211> LENGTH: 27
<212> TYPE: PRT
<213> ORGANISM: Mus musculus

<400> SEQUENCE: 23

```
Glu His Ile His Arg Ala Gly Gly Leu Phe Val Ala Asp Ala Ile Gln
1               5                   10                  15

Val Gly Phe Gly Arg Ile Gly Lys His Phe Trp
            20                  25
```

<210> SEQ ID NO 24
<211> LENGTH: 5
<212> TYPE: PRT
<213> ORGANISM: Artificial Sequence
<220> FEATURE:
<223> OTHER INFORMATION: Linker

<400> SEQUENCE: 24

```
Gly Leu Ser Gly Leu
1               5
```

<210> SEQ ID NO 25
<211> LENGTH: 5
<212> TYPE: PRT
<213> ORGANISM: Artificial Sequence
<220> FEATURE:
<223> OTHER INFORMATION: Linker

<400> SEQUENCE: 25

```
Gly Leu Gly Gly Leu
1               5
```

<210> SEQ ID NO 26
<211> LENGTH: 12
<212> TYPE: PRT
<213> ORGANISM: Artificial Sequence
<220> FEATURE:
<223> OTHER INFORMATION: Hinge region

<400> SEQUENCE: 26

```
Glu Leu Lys Thr Pro Leu Gly Asp Thr Thr His Thr
1               5                   10
```

<210> SEQ ID NO 27
<211> LENGTH: 15
<212> TYPE: PRT
<213> ORGANISM: Artificial Sequence
<220> FEATURE:

<223> OTHER INFORMATION: Hinge region

<400> SEQUENCE: 27

Glu Pro Lys Ser Cys Asp Thr Pro Pro Cys Pro Arg Cys Pro
1               5                   10                  15

<210> SEQ ID NO 28
<211> LENGTH: 10
<212> TYPE: PRT
<213> ORGANISM: Artificial Sequence
<220> FEATURE:
<223> OTHER INFORMATION: Linker

<400> SEQUENCE: 28

Gly Gly Gly Ser Ser Gly Gly Gly Ser Gly
1               5                   10

<210> SEQ ID NO 29
<211> LENGTH: 107
<212> TYPE: PRT
<213> ORGANISM: Homo sapiens

<400> SEQUENCE: 29

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Ser Gly Gln Pro Glu
            35                  40                  45

Asn Asn Tyr Asn Thr Thr Pro Pro Met Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro Gly Lys
            100                 105

<210> SEQ ID NO 30
<211> LENGTH: 666
<212> TYPE: PRT
<213> ORGANISM: Artificial Sequence
<220> FEATURE:
<223> OTHER INFORMATION: Construct

<400> SEQUENCE: 30

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
            35                  40                  45

Ala Asp Tyr Phe Glu Thr Ser Ser Gln Cys Ser Lys Pro Ser Val Ile
        50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Ile Glu Pro Lys Ser Cys Asp
            100                 105                 110

```
Thr Pro Pro Pro Cys Pro Arg Cys Pro Gly Gly Ser Gly Gly
        115                 120                 125

Gly Ser Gly Gly Gln Pro Arg Glu Pro Gln Val Tyr Thr Leu Pro Pro
    130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Ser Gly
                165                 170                 175

Gln Pro Glu Asn Asn Tyr Asn Thr Thr Pro Pro Met Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Ile Phe Ser Cys Ser Val Met His Glu Ala Leu His
    210                 215                 220

Asn Arg Phe Thr Gln Lys Ser Leu Ser Leu Ser Pro Gly Lys Gly Leu
225                 230                 235                 240

Gly Gly Leu Met His Gly Asp Thr Pro Thr Leu His Glu Tyr Met Leu
                245                 250                 255

Asp Leu Gln Pro Glu Thr Thr Asp Leu Tyr Gly Tyr Gly Gln Leu Asn
            260                 265                 270

Asp Ser Ser Glu Glu Glu Asp Glu Ile Asp Gly Pro Ala Gly Gln Ala
        275                 280                 285

Glu Pro Asp Arg Ala His Tyr Asn Ile Val Thr Phe Cys Cys Lys Cys
    290                 295                 300

Asp Ser Thr Leu Arg Leu Cys Val Gln Ser Thr His Val Asp Ile Arg
305                 310                 315                 320

Thr Leu Glu Asp Leu Leu Met Gly Thr Leu Gly Ile Val Cys Pro Ile
                325                 330                 335

Cys Ser Gln Lys Pro Gly Gly Ser Ser Gly Gly Gly Ser Gly Val
            340                 345                 350

Ile Leu Pro Gln Ala Pro Ser Gly Pro Ser Tyr Ala Thr Tyr Leu Gln
        355                 360                 365

Pro Ala Gln Ala Gln Met Leu Thr Pro Gly Gly Gly Gly Ser Leu
    370                 375                 380

His Ser Gly Gln Asn His Leu Lys Glu Met Ala Ile Ser Val Leu Glu
385                 390                 395                 400

Ala Arg Ala Cys Ala Ala Ala Gly Gln Ser Gly Gly Gly Gly Ser Pro
                405                 410                 415

Leu Leu Pro Phe Tyr Pro Pro Asp Glu Ala Leu Glu Ile Gly Leu Glu
            420                 425                 430

Leu Asn Ser Ser Ala Leu Pro Pro Thr Glu Gly Gly Gly Gly Ser Ala
        435                 440                 445

Gly Thr Gln Cys Glu Tyr Trp Ala Ser Arg Ala Leu Asp Ser Glu His
    450                 455                 460

Ser Ile Gly Ser Met Ile Gln Leu Pro Gln Gly Gly Gly Gly Ser Ala
465                 470                 475                 480

Ala Tyr Lys Gly His His Tyr Pro Gly Pro Gly Asn Tyr Phe Trp Lys
                485                 490                 495

Cys Leu Phe Met Ser Gly Leu Ser Glu Val Gly Gly Gly Gly Ser Asp
            500                 505                 510

Thr Leu Ser Ala Met Ser Asn Pro Arg Ala Met Gln Val Leu Leu Gln
        515                 520                 525
```

```
Ile Gln Gln Gly Leu Gln Thr Leu Ala Thr Gly Gly Gly Ser Asp
    530                 535                 540

Lys Pro Leu Arg Arg Asn Asn Ser Tyr Thr Ser Tyr Ile Met Ala Ile
545                 550                 555                 560

Cys Gly Met Pro Leu Asp Ser Phe Arg Ala Gly Gly Gly Ser Glu
            565                 570                 575

Val Ile Gln Thr Ser Lys Tyr Tyr Met Arg Asp Val Ile Ala Ile Glu
                580                 585                 590

Ser Ala Trp Leu Leu Glu Leu Ala Pro His Gly Gly Gly Ser Gly
            595                 600                 605

Tyr Ile Ser Arg Val Thr Ala Gly Lys Asp Ser Tyr Ile Ala Leu Val
                610                 615                 620

Asp Lys Asn Ile Met Gly Tyr Ile Ala Ser Gly Gly Gly Ser Glu
625                 630                 635                 640

His Ile His Arg Ala Gly Gly Leu Phe Val Ala Asp Ala Ile Gln Val
                645                 650                 655

Gly Phe Gly Arg Ile Gly Lys His Phe Trp
                660                 665
```

<210> SEQ ID NO 31
<211> LENGTH: 442
<212> TYPE: PRT
<213> ORGANISM: Artificial Sequence
<220> FEATURE:
<223> OTHER INFORMATION: Construct

<400> SEQUENCE: 31

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
            35                  40                  45

Ala Asp Tyr Phe Glu Thr Ser Ser Gln Cys Ser Lys Pro Ser Val Ile
50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Ile Glu Pro Lys Ser Cys Asp
                100                 105                 110

Thr Pro Pro Pro Cys Pro Arg Cys Pro Gly Gly Gly Ser Gly Gly
            115                 120                 125

Gly Ser Gly Gly Gln Pro Arg Glu Pro Gln Val Tyr Thr Leu Pro Pro
130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Ser Gly
                165                 170                 175

Gln Pro Glu Asn Asn Tyr Asn Thr Thr Pro Pro Met Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Ile Phe Ser Cys Ser Val Met His Glu Ala Leu His
    210                 215                 220
```

```
Asn Arg Phe Thr Gln Lys Ser Leu Ser Leu Ser Pro Gly Lys Gly Leu
225                 230                 235                 240

Gly Gly Leu Met His Gly Asp Thr Pro Thr Leu His Glu Tyr Met Leu
            245                 250                 255

Asp Leu Gln Pro Glu Thr Thr Asp Leu Tyr Gly Tyr Gly Gln Leu Asn
        260                 265                 270

Asp Ser Ser Glu Glu Glu Asp Glu Ile Asp Gly Pro Ala Gly Gln Ala
    275                 280                 285

Glu Pro Asp Arg Ala His Tyr Asn Ile Val Thr Phe Cys Cys Lys Cys
290                 295                 300

Asp Ser Thr Leu Arg Leu Cys Val Gln Ser Thr His Val Asp Ile Arg
305                 310                 315                 320

Thr Leu Glu Asp Leu Leu Met Gly Thr Leu Gly Ile Val Cys Pro Ile
                325                 330                 335

Cys Ser Gln Lys Pro Gly Gly Gly Ser Ser Gly Gly Gly Ser Gly Val
            340                 345                 350

Ile Leu Pro Gln Ala Pro Ser Gly Pro Ser Tyr Ala Thr Tyr Leu Gln
        355                 360                 365

Pro Ala Gln Ala Gln Met Leu Thr Pro Pro Gly Gly Gly Gly Ser Leu
    370                 375                 380

His Ser Gly Gln Asn His Leu Lys Glu Met Ala Ile Ser Val Leu Glu
385                 390                 395                 400

Ala Arg Ala Cys Ala Ala Gly Gln Ser Gly Gly Gly Gly Ser Pro
                405                 410                 415

Leu Leu Pro Phe Tyr Pro Pro Asp Glu Ala Leu Glu Ile Gly Leu Glu
            420                 425                 430

Leu Asn Ser Ser Ala Leu Pro Pro Thr Glu
        435                 440

<210> SEQ ID NO 32
<211> LENGTH: 817
<212> TYPE: PRT
<213> ORGANISM: Artificial Sequence
<220> FEATURE:
<223> OTHER INFORMATION: Construct

<400> SEQUENCE: 32

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Ile Glu Pro Lys Ser Cys Asp
            100                 105                 110

Thr Pro Pro Pro Cys Pro Arg Cys Pro Gly Gly Gly Ser Ser Gly Gly
        115                 120                 125

Gly Ser Gly Gly Gln Pro Arg Glu Pro Gln Val Tyr Thr Leu Pro Pro
    130                 135                 140
```

```
Ser Arg Glu Glu Met Thr Lys Met Gln Val Ser Thr Ala Ala Leu Ala
145                 150                 155                 160

Val Leu Leu Cys Thr Met Ala Leu Cys Asn Gln Val Leu Ser Ala Pro
                165                 170                 175

Leu Ala Ala Asp Thr Pro Thr Ala Cys Cys Phe Ser Tyr Thr Ser Arg
            180                 185                 190

Gln Ile Pro Gln Asn Phe Ile Ala Asp Tyr Phe Glu Thr Ser Ser Gln
        195                 200                 205

Cys Ser Lys Pro Ser Val Ile Phe Leu Thr Lys Arg Gly Arg Gln Val
    210                 215                 220

Cys Ala Asp Pro Ser Glu Glu Trp Val Gln Lys Tyr Val Ser Asp Leu
225                 230                 235                 240

Glu Leu Ser Ala Glu Leu Lys Thr Pro Leu Gly Asp Thr Thr His Thr
                245                 250                 255

Ile Glu Pro Lys Ser Cys Asp Thr Pro Pro Cys Pro Arg Cys Pro
                260                 265                 270

Gly Gly Gly Ser Ser Gly Gly Gly Ser Gly Gln Pro Arg Glu Pro
            275                 280                 285

Gln Val Tyr Thr Leu Pro Pro Ser Arg Glu Glu Met Thr Lys Asn Gln
    290                 295                 300

Val Ser Leu Thr Cys Leu Val Lys Gly Phe Tyr Pro Ser Asp Ile Ala
305                 310                 315                 320

Val Glu Trp Glu Ser Ser Gly Gln Pro Glu Asn Asn Tyr Asn Thr Thr
                325                 330                 335

Pro Pro Met Leu Asp Ser Asp Gly Ser Phe Phe Leu Tyr Ser Lys Leu
            340                 345                 350

Thr Val Asp Lys Ser Arg Trp Gln Gln Gly Asn Ile Phe Ser Cys Ser
        355                 360                 365

Val Met His Glu Ala Leu His Asn Arg Phe Thr Gln Lys Ser Leu Ser
    370                 375                 380

Leu Ser Pro Gly Lys Gly Leu Gly Gly Leu Met His Gly Asp Thr Pro
385                 390                 395                 400

Thr Leu His Glu Tyr Met Leu Asp Leu Gln Pro Glu Thr Thr Asp Leu
                405                 410                 415

Tyr Gly Tyr Gly Gln Leu Asn Asp Ser Ser Glu Glu Glu Asp Glu Ile
            420                 425                 430

Asp Gly Pro Ala Gly Gln Ala Glu Pro Asp Arg Ala His Tyr Asn Ile
        435                 440                 445

Val Thr Phe Cys Cys Lys Cys Asp Ser Thr Leu Arg Leu Cys Val Gln
    450                 455                 460

Ser Thr His Val Asp Ile Arg Thr Leu Glu Asp Leu Leu Met Gly Thr
465                 470                 475                 480

Leu Gly Ile Val Cys Pro Ile Cys Ser Gln Lys Pro Gly Gly Gly Ser
                485                 490                 495

Ser Gly Gly Gly Ser Gly Pro Ser Lys Pro Ser Phe Gln Glu Phe Val
            500                 505                 510

Asp Trp Glu Asn Val Ser Pro Glu Leu Asn Ser Thr Asp Gln Pro Phe
        515                 520                 525

Leu Gly Gly Gly Ser Arg Glu Gly Val Glu Leu Cys Pro Gly Asn
    530                 535                 540

Lys Tyr Glu Met Arg Arg His Gly Thr Thr His Ser Leu Val Ile His
545                 550                 555                 560

Asp Gly Gly Gly Gly Ser Ser His Cys His Trp Asn Asp Leu Ala Val
```

```
            565                 570                 575
Ile Pro Ala Gly Val His Asn Trp Asp Phe Glu Pro Arg Lys Val
            580                 585                 590

Ser Gly Gly Gly Ser Gly Arg Gly His Leu Leu Gly Arg Leu Ala
            595                 600                 605

Ala Ile Val Gly Lys Gln Val Leu Leu Gly Arg Lys Val Val Val
            610                 615                 620

Arg Gly Gly Gly Ser Phe Arg Arg Lys Ala Phe Leu His Trp Tyr
625                 630                 635                 640

Thr Gly Glu Ala Met Asp Glu Met Glu Phe Thr Glu Ala Glu Ser Asn
                    645                 650                 655

Met Gly Gly Gly Ser Val Val Asp Arg Asn Pro Gln Phe Leu Asp
            660                 665                 670

Pro Val Leu Ala Tyr Leu Met Lys Gly Leu Cys Glu Lys Pro Leu Ala
                    675                 680                 685

Ser Gly Gly Gly Ser Ser Pro Asp Glu Val Ala Leu Val Glu
            690                 695                 700

Gly Val Gln Ser Leu Gly Phe Thr Tyr Leu Arg Leu Lys Asp Asn Tyr
705                 710                 715                 720

Met Gly Gly Gly Ser Glu Phe Lys His Ile Lys Ala Phe Asp Arg
            725                 730                 735

Thr Phe Ala Asn Asn Pro Gly Pro Met Val Val Phe Ala Thr Pro Gly
                    740                 745                 750

Met Gly Gly Gly Ser Ser Thr Ala Asn Tyr Asn Thr Ser His Leu
            755                 760                 765

Asn Asn Asp Val Trp Gln Ile Phe Glu Asn Pro Val Asp Trp Lys Glu
770                 775                 780

Lys Gly Gly Gly Ser Asp Ser Gly Ser Pro Phe Pro Ala Ala Val
785                 790                 795                 800

Ile Leu Arg Asp Ala Leu His Met Ala Arg Gly Leu Lys Tyr Leu His
                    805                 810                 815

Gln

<210> SEQ ID NO 33
<211> LENGTH: 442
<212> TYPE: PRT
<213> ORGANISM: Artificial Sequence
<220> FEATURE:
<223> OTHER INFORMATION: Construct

<400> SEQUENCE: 33

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
            35                  40                  45

Ala Asp Tyr Phe Glu Thr Ser Ser Gln Cys Ser Lys Pro Ser Val Ile
50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Ile Glu Pro Lys Ser Cys Asp
                100                 105                 110
```

```
Thr Pro Pro Pro Cys Pro Arg Cys Pro Gly Gly Ser Gly Gly
        115                 120                 125

Gly Ser Gly Gly Gln Pro Arg Glu Pro Gln Val Tyr Thr Leu Pro Pro
    130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Ser Gly
                165                 170                 175

Gln Pro Glu Asn Asn Tyr Asn Thr Thr Pro Pro Met Leu Asp Ser Asp
                180                 185                 190

Gly Ser Phe Phe Leu Tyr Ser Lys Leu Thr Val Asp Lys Ser Arg Trp
            195                 200                 205

Gln Gln Gly Asn Ile Phe Ser Cys Ser Val Met His Glu Ala Leu His
        210                 215                 220

Asn Arg Phe Thr Gln Lys Ser Leu Ser Leu Ser Pro Gly Lys Gly Leu
225                 230                 235                 240

Gly Gly Leu Met His Gly Asp Thr Pro Thr Leu His Glu Tyr Met Leu
                245                 250                 255

Asp Leu Gln Pro Glu Thr Thr Asp Leu Tyr Gly Tyr Gly Gln Leu Asn
                260                 265                 270

Asp Ser Ser Glu Glu Glu Asp Glu Ile Asp Gly Pro Ala Gly Gln Ala
            275                 280                 285

Glu Pro Asp Arg Ala His Tyr Asn Ile Val Thr Phe Cys Cys Lys Cys
        290                 295                 300

Asp Ser Thr Leu Arg Leu Cys Val Gln Ser Thr His Val Asp Ile Arg
305                 310                 315                 320

Thr Leu Glu Asp Leu Leu Met Gly Thr Leu Gly Ile Val Cys Pro Ile
                325                 330                 335

Cys Ser Gln Lys Pro Gly Gly Ser Ser Gly Gly Ser Gly Pro
                340                 345                 350

Ser Lys Pro Ser Phe Gln Glu Phe Val Asp Trp Glu Asn Val Ser Pro
        355                 360                 365

Glu Leu Asn Ser Thr Asp Gln Pro Phe Leu Gly Gly Gly Ser Arg
        370                 375                 380

Glu Gly Val Glu Leu Cys Pro Gly Asn Lys Tyr Glu Met Arg Arg His
385                 390                 395                 400

Gly Thr Thr His Ser Leu Val Ile His Asp Gly Gly Gly Ser Ser
                405                 410                 415

His Cys His Trp Asn Asp Leu Ala Val Ile Pro Ala Gly Val Val His
                420                 425                 430

Asn Trp Asp Phe Glu Pro Arg Lys Val Ser
        435                 440
```

<210> SEQ ID NO 34
<211> LENGTH: 19
<212> TYPE: PRT
<213> ORGANISM: Artificial Sequence
<220> FEATURE:
<223> OTHER INFORMATION: Signal peptide

<400> SEQUENCE: 34

```
Met Asn Phe Gly Leu Arg Leu Ile Phe Leu Val Leu Thr Leu Lys Gly
1               5                   10                  15

Val Gln Cys
```

<210> SEQ ID NO 35
<211> LENGTH: 22
<212> TYPE: PRT
<213> ORGANISM: Artificial Sequence
<220> FEATURE:
<223> OTHER INFORMATION: Signal peptide

<400> SEQUENCE: 35

Met Asp Ala Met Lys Arg Gly Leu Cys Cys Val Leu Leu Leu Cys Gly
1               5                   10                  15

Ala Val Phe Val Ser Pro
            20

<210> SEQ ID NO 36
<211> LENGTH: 27
<212> TYPE: PRT
<213> ORGANISM: Mus musculus

<400> SEQUENCE: 36

Ala Asn Phe Glu Ser Gly Lys His Lys Tyr Arg Gln Thr Ala Met Phe
1               5                   10                  15

Thr Ala Thr Met Pro Pro Ala Val Glu Arg Leu
            20                  25

<210> SEQ ID NO 37
<211> LENGTH: 711
<212> TYPE: PRT
<213> ORGANISM: Artificial Sequence
<220> FEATURE:
<223> OTHER INFORMATION: Construct

<400> SEQUENCE: 37

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Ile Glu Pro Lys Ser Cys Asp
            100                 105                 110

Thr Pro Pro Pro Cys Pro Arg Cys Pro Gly Gly Gly Ser Ser Gly Gly
        115                 120                 125

Gly Ser Gly Gly Gln Pro Arg Glu Pro Gln Val Tyr Thr Leu Pro Pro
    130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Ser Gly
                165                 170                 175

Gln Pro Glu Asn Asn Tyr Asn Thr Thr Pro Pro Met Leu Asp Ser Asp
            180                 185                 190

Gly Ser Phe Phe Leu Tyr Ser Lys Leu Thr Val Asp Lys Ser Arg Trp
        195                 200                 205

-continued

```
Gln Gln Gly Asn Ile Phe Ser Cys Ser Val Met His Glu Ala Leu His
    210                 215                 220
Asn Arg Phe Thr Gln Lys Ser Leu Ser Leu Ser Pro Gly Lys Gly Leu
225                 230                 235                 240
Gly Gly Leu Met His Gly Asp Thr Pro Thr Leu His Glu Tyr Met Leu
                245                 250                 255
Asp Leu Gln Pro Glu Thr Thr Asp Leu Tyr Gly Tyr Gly Gln Leu Asn
            260                 265                 270
Asp Ser Ser Glu Glu Asp Glu Ile Asp Gly Pro Ala Gly Gln Ala
        275                 280                 285
Glu Pro Asp Arg Ala His Tyr Asn Ile Val Thr Phe Cys Cys Lys Cys
    290                 295                 300
Asp Ser Thr Leu Arg Leu Cys Val Gln Ser Thr His Val Asp Ile Arg
305                 310                 315                 320
Thr Leu Glu Asp Leu Leu Met Gly Thr Leu Gly Ile Val Cys Pro Ile
                325                 330                 335
Cys Ser Gln Lys Pro Gly Gly Gly Ser Gly Gly Gly Ser Gly Pro
            340                 345                 350
Ser Lys Pro Ser Phe Gln Glu Phe Val Asp Trp Glu Asn Val Ser Pro
    355                 360                 365
Glu Leu Asn Ser Thr Asp Gln Pro Phe Leu Gly Gly Gly Ser Gly
    370                 375                 380
Gly Gly Gly Ser Arg Glu Gly Val Glu Leu Cys Pro Gly Asn Lys Tyr
385                 390                 395                 400
Glu Met Arg Arg His Gly Thr Thr His Ser Leu Val Ile His Asp Gly
                405                 410                 415
Gly Gly Gly Ser Gly Gly Gly Ser Ser His Cys His Trp Asn Asp
            420                 425                 430
Leu Ala Val Ile Pro Ala Gly Val His Asn Trp Asp Phe Glu Pro
        435                 440                 445
Arg Lys Val Ser Gly Gly Gly Ser Gly Gly Gly Gly Ser Gly Arg
    450                 455                 460
Gly His Leu Leu Gly Arg Leu Ala Ala Ile Val Gly Lys Gln Val Leu
465                 470                 475                 480
Leu Gly Arg Lys Val Val Val Arg Gly Gly Gly Ser Gly Gly
                485                 490                 495
Gly Gly Ser Phe Arg Arg Lys Ala Phe Leu His Trp Tyr Thr Gly Glu
            500                 505                 510
Ala Met Asp Glu Met Glu Phe Thr Glu Ala Glu Ser Asn Met Gly Gly
    515                 520                 525
Gly Gly Ser Gly Gly Gly Gly Ser Val Val Asp Arg Asn Pro Gln Phe
530                 535                 540
Leu Asp Pro Val Leu Ala Tyr Leu Met Lys Gly Leu Cys Glu Lys Pro
545                 550                 555                 560
Leu Ala Ser Gly Gly Gly Ser Gly Gly Gly Gly Ser Ser Ser Pro
                565                 570                 575
Asp Glu Val Ala Leu Val Glu Gly Val Gln Ser Leu Gly Phe Thr Tyr
            580                 585                 590
Leu Arg Leu Lys Asp Asn Tyr Met Gly Gly Gly Ser Gly Gly Gly
        595                 600                 605
Gly Ser Glu Phe Lys His Ile Lys Ala Phe Asp Arg Thr Phe Ala Asn
    610                 615                 620
Asn Pro Gly Pro Met Val Val Phe Ala Thr Pro Gly Met Gly Gly Gly
```

```
                625                 630                 635                 640
Gly Ser Gly Gly Gly Ser Ser Thr Ala Asn Tyr Asn Thr Ser His
                    645                 650                 655
Leu Asn Asn Asp Val Trp Gln Ile Phe Glu Asn Pro Val Asp Trp Lys
                660                 665                 670
Glu Lys Gly Gly Gly Ser Gly Gly Gly Ser Asp Ser Gly Ser
            675                 680                 685
Pro Phe Pro Ala Ala Val Ile Leu Arg Asp Ala Leu His Met Ala Arg
690                 695                 700
Gly Leu Lys Tyr Leu His Gln
705                 710

<210> SEQ ID NO 38
<211> LENGTH: 452
<212> TYPE: PRT
<213> ORGANISM: Artificial Sequence
<220> FEATURE:
<223> OTHER INFORMATION: Construct

<400> SEQUENCE: 38

Met Gln Val Ser Thr Ala Ala Leu Ala Val Leu Leu Cys Thr Met Ala
1               5                   10                  15
Leu Cys Asn Gln Val Leu Ser Ala Pro Leu Ala Ala Asp Thr Pro Thr
                20                  25                  30
Ala Cys Cys Phe Ser Tyr Thr Ser Arg Gln Ile Pro Gln Asn Phe Ile
            35                  40                  45
Ala Asp Tyr Phe Glu Thr Ser Ser Gln Cys Ser Lys Pro Ser Val Ile
        50                  55                  60
Phe Leu Thr Lys Arg Gly Arg Gln Val Cys Ala Asp Pro Ser Glu Glu
65                  70                  75                  80
Trp Val Gln Lys Tyr Val Ser Asp Leu Glu Leu Ser Ala Glu Leu Lys
                85                  90                  95
Thr Pro Leu Gly Asp Thr Thr His Thr Ile Glu Pro Lys Ser Cys Asp
                100                 105                 110
Thr Pro Pro Pro Cys Pro Arg Cys Pro Gly Gly Gly Ser Ser Gly Gly
            115                 120                 125
Gly Ser Gly Gly Gln Pro Arg Glu Pro Gln Val Tyr Thr Leu Pro Pro
        130                 135                 140
Ser Arg Glu Glu Met Thr Lys Asn Gln Val Ser Leu Thr Cys Leu Val
145                 150                 155                 160
Lys Gly Phe Tyr Pro Ser Asp Ile Ala Val Glu Trp Glu Ser Ser Gly
                165                 170                 175
Gln Pro Glu Asn Asn Tyr Asn Thr Thr Pro Pro Met Leu Asp Ser Asp
                180                 185                 190
Gly Ser Phe Phe Leu Tyr Ser Lys Leu Thr Val Asp Lys Ser Arg Trp
            195                 200                 205
Gln Gln Gly Asn Ile Phe Ser Cys Ser Val Met His Glu Ala Leu His
        210                 215                 220
Asn Arg Phe Thr Gln Lys Ser Leu Ser Leu Ser Pro Gly Lys Gly Leu
225                 230                 235                 240
Gly Gly Leu Met His Gly Asp Thr Pro Thr Leu His Glu Tyr Met Leu
                245                 250                 255
Asp Leu Gln Pro Glu Thr Thr Asp Leu Tyr Gly Tyr Gly Gln Leu Asn
                260                 265                 270
Asp Ser Ser Glu Glu Glu Asp Glu Ile Asp Gly Pro Ala Gly Gln Ala
```

```
            275                 280                 285
Glu Pro Asp Arg Ala His Tyr Asn Ile Val Thr Phe Cys Cys Lys Cys
290                 295                 300

Asp Ser Thr Leu Arg Leu Cys Val Gln Ser Thr His Val Asp Ile Arg
305                 310                 315                 320

Thr Leu Glu Asp Leu Leu Met Gly Thr Leu Gly Ile Val Cys Pro Ile
                325                 330                 335

Cys Ser Gln Lys Pro Gly Gly Gly Ser Gly Gly Gly Ser Gly Pro
            340                 345                 350

Ser Lys Pro Ser Phe Gln Glu Phe Val Asp Trp Glu Asn Val Ser Pro
            355                 360                 365

Glu Leu Asn Ser Thr Asp Gln Pro Phe Leu Gly Gly Gly Gly Ser Gly
        370                 375                 380

Gly Gly Gly Ser Arg Glu Gly Val Glu Leu Cys Pro Gly Asn Lys Tyr
385                 390                 395                 400

Glu Met Arg Arg His Gly Thr Thr His Ser Leu Val Ile His Asp Gly
                405                 410                 415

Gly Gly Gly Ser Gly Gly Gly Gly Ser Ser His Cys His Trp Asn Asp
            420                 425                 430

Leu Ala Val Ile Pro Ala Gly Val Val His Asn Trp Asp Phe Glu Pro
                435                 440                 445

Arg Lys Val Ser
    450

<210> SEQ ID NO 39
<211> LENGTH: 666
<212> TYPE: PRT
<213> ORGANISM: Artificial Sequence
<220> FEATURE:
<223> OTHER INFORMATION: Construct

<400> SEQUENCE: 39

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
            35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Ile Glu Pro Lys Ser Cys Asp
                100                 105                 110

Thr Pro Pro Pro Cys Pro Arg Cys Pro Gly Gly Ser Ser Gly Gly
            115                 120                 125

Gly Ser Gly Gly Gln Pro Arg Glu Pro Gln Val Tyr Thr Leu Pro Pro
        130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Ser Gly
                165                 170                 175

Gln Pro Glu Asn Asn Tyr Asn Thr Thr Pro Pro Met Leu Asp Ser Asp
```

```
                180             185             190
Gly Ser Phe Phe Leu Tyr Ser Lys Leu Thr Val Asp Lys Ser Arg Trp
            195             200             205

Gln Gln Gly Asn Ile Phe Ser Cys Ser Val Met His Glu Ala Leu His
            210             215             220

Asn Arg Phe Thr Gln Lys Ser Leu Ser Leu Ser Pro Gly Lys Gly Leu
225             230             235             240

Gly Gly Leu Met His Gly Asp Thr Pro Thr Leu His Glu Tyr Met Leu
                245             250             255

Asp Leu Gln Pro Glu Thr Thr Asp Leu Tyr Gly Tyr Gly Gln Leu Asn
            260             265             270

Asp Ser Ser Glu Glu Glu Asp Glu Ile Asp Gly Pro Ala Gly Gln Ala
            275             280             285

Glu Pro Asp Arg Ala His Tyr Asn Ile Val Thr Phe Cys Cys Lys Cys
            290             295             300

Asp Ser Thr Leu Arg Leu Cys Val Gln Ser Thr His Val Asp Ile Arg
305             310             315             320

Thr Leu Glu Asp Leu Leu Met Gly Thr Leu Gly Ile Val Cys Pro Ile
                325             330             335

Cys Ser Gln Lys Pro Gly Gly Gly Ser Gly Gly Gly Ser Gly Ser
            340             345             350

Thr Ala Asn Tyr Asn Thr Ser His Leu Asn Asn Asp Val Trp Gln Ile
            355             360             365

Phe Glu Asn Pro Val Asp Trp Lys Glu Lys Gly Gly Gly Ser Phe
            370             375             380

Arg Arg Lys Ala Phe Leu His Trp Tyr Thr Gly Glu Ala Met Asp Glu
385             390             395             400

Met Glu Phe Thr Glu Ala Glu Ser Asn Met Gly Gly Gly Ser Pro
                405             410             415

Ser Lys Pro Ser Phe Gln Glu Phe Val Asp Trp Glu Asn Val Ser Pro
            420             425             430

Glu Leu Asn Ser Thr Asp Gln Pro Phe Leu Gly Gly Gly Ser Gly
            435             440             445

Arg Gly His Leu Leu Gly Arg Leu Ala Ala Ile Val Gly Lys Gln Val
            450             455             460

Leu Leu Gly Arg Lys Val Val Val Arg Gly Gly Gly Ser Val
465             470             475             480

Val Asp Arg Asn Pro Gln Phe Leu Asp Pro Val Leu Ala Tyr Leu Met
            485             490             495

Lys Gly Leu Cys Glu Lys Pro Leu Ala Ser Gly Gly Gly Ser Glu
            500             505             510

Phe Lys His Ile Lys Ala Phe Asp Arg Thr Phe Ala Asn Asn Pro Gly
            515             520             525

Pro Met Val Val Phe Ala Thr Pro Gly Met Gly Gly Gly Ser Asp
            530             535             540

Ser Gly Ser Pro Phe Pro Ala Ala Val Ile Leu Arg Asp Ala Leu His
545             550             555             560

Met Ala Arg Gly Leu Lys Tyr Leu His Gln Gly Gly Gly Ser Ser
            565             570             575

His Cys His Trp Asn Asp Leu Ala Val Ile Pro Ala Gly Val Val His
            580             585             590

Asn Trp Asp Phe Glu Pro Arg Lys Val Ser Gly Gly Gly Ser Ser
            595             600             605
```

```
Ser Pro Asp Glu Val Ala Leu Val Glu Gly Val Gln Ser Leu Gly Phe
            610                 615                 620

Thr Tyr Leu Arg Leu Lys Asp Asn Tyr Met Gly Gly Gly Ser Arg
625                 630                 635                 640

Glu Gly Val Glu Leu Cys Pro Gly Asn Lys Tyr Glu Met Arg Arg His
                645                 650                 655

Gly Thr Thr His Ser Leu Val Ile His Asp
            660                 665

<210> SEQ ID NO 40
<211> LENGTH: 442
<212> TYPE: PRT
<213> ORGANISM: Artificial Sequence
<220> FEATURE:
<223> OTHER INFORMATION: Construct

<400> SEQUENCE: 40

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
            35                  40                  45

Ala Asp Tyr Phe Glu Thr Ser Ser Gln Cys Ser Lys Pro Ser Val Ile
        50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Ile Glu Pro Lys Ser Cys Asp
                100                 105                 110

Thr Pro Pro Pro Cys Pro Arg Cys Pro Gly Gly Gly Ser Ser Gly Gly
            115                 120                 125

Gly Ser Gly Gly Gln Pro Arg Glu Pro Gln Val Tyr Thr Leu Pro Pro
        130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Ser Gly
                165                 170                 175

Gln Pro Glu Asn Asn Tyr Asn Thr Thr Pro Pro Met Leu Asp Ser Asp
                180                 185                 190

Gly Ser Phe Phe Leu Tyr Ser Lys Leu Thr Val Asp Lys Ser Arg Trp
            195                 200                 205

Gln Gln Gly Asn Ile Phe Ser Cys Ser Val Met His Glu Ala Leu His
        210                 215                 220

Asn Arg Phe Thr Gln Lys Ser Leu Ser Leu Ser Pro Gly Lys Gly Leu
225                 230                 235                 240

Gly Gly Leu Met His Gly Asp Thr Pro Thr Leu His Glu Tyr Met Leu
                245                 250                 255

Asp Leu Gln Pro Glu Thr Thr Asp Leu Tyr Gly Tyr Gly Gln Leu Asn
                260                 265                 270

Asp Ser Ser Glu Glu Glu Asp Glu Ile Asp Gly Pro Ala Gly Gln Ala
            275                 280                 285

Glu Pro Asp Arg Ala His Tyr Asn Ile Val Thr Phe Cys Cys Lys Cys
        290                 295                 300
```

```
Asp Ser Thr Leu Arg Leu Cys Val Gln Ser Thr His Val Asp Ile Arg
305                 310                 315                 320

Thr Leu Glu Asp Leu Leu Met Gly Thr Leu Gly Ile Val Cys Pro Ile
            325                 330                 335

Cys Ser Gln Lys Pro Gly Gly Gly Ser Gly Gly Gly Ser Gly Pro
            340                 345                 350

Ser Lys Pro Ser Phe Gln Glu Phe Val Asp Trp Glu Asn Val Ser Pro
            355                 360                 365

Glu Leu Asn Ser Thr Asp Gln Pro Phe Leu Gly Gly Gly Ser Glu
    370                 375                 380

Phe Lys His Ile Lys Ala Phe Asp Arg Thr Phe Ala Asn Asn Pro Gly
385                 390                 395                 400

Pro Met Val Val Phe Ala Thr Pro Gly Met Gly Gly Gly Ser Ser
                405                 410                 415

His Cys His Trp Asn Asp Leu Ala Val Ile Pro Ala Gly Val Val His
            420                 425                 430

Asn Trp Asp Phe Glu Pro Arg Lys Val Ser
            435                 440

<210> SEQ ID NO 41
<211> LENGTH: 442
<212> TYPE: PRT
<213> ORGANISM: Artificial Sequence
<220> FEATURE:
<223> OTHER INFORMATION: Construct

<400> SEQUENCE: 41

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Ile Glu Pro Lys Ser Cys Asp
            100                 105                 110

Thr Pro Pro Pro Cys Pro Arg Cys Pro Gly Gly Gly Ser Gly Gly Gly
        115                 120                 125

Gly Ser Gly Gly Gln Pro Arg Glu Pro Gln Val Tyr Thr Leu Pro Pro
    130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Ser Gly
                165                 170                 175

Gln Pro Glu Asn Asn Tyr Asn Thr Thr Pro Pro Met Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Ile Phe Ser Cys Ser Val Met His Glu Ala Leu His
    210                 215                 220
```

```
Asn Arg Phe Thr Gln Lys Ser Leu Ser Leu Ser Pro Gly Lys Gly Leu
225                 230                 235                 240

Gly Gly Leu Met His Gly Asp Thr Pro Thr Leu His Glu Tyr Met Leu
            245                 250                 255

Asp Leu Gln Pro Glu Thr Thr Asp Leu Tyr Gly Tyr Gly Gln Leu Asn
        260                 265                 270

Asp Ser Ser Glu Glu Glu Asp Glu Ile Asp Gly Pro Ala Gly Gln Ala
    275                 280                 285

Glu Pro Asp Arg Ala His Tyr Asn Ile Val Thr Phe Cys Cys Lys Cys
290                 295                 300

Asp Ser Thr Leu Arg Leu Cys Val Gln Ser Thr His Val Asp Ile Arg
305                 310                 315                 320

Thr Leu Glu Asp Leu Leu Met Gly Thr Leu Gly Ile Val Cys Pro Ile
                325                 330                 335

Cys Ser Gln Lys Pro Gly Gly Ser Ser Gly Gly Gly Ser Gly Pro
                340                 345                 350

Ser Lys Pro Ser Phe Gln Glu Phe Val Asp Trp Glu Asn Val Ser Pro
            355                 360                 365

Glu Leu Asn Ser Thr Asp Gln Pro Phe Leu Gly Gly Gly Ser Ser
        370                 375                 380

His Cys His Trp Asn Asp Leu Ala Val Ile Pro Ala Gly Val Val His
385                 390                 395                 400

Asn Trp Asp Phe Glu Pro Arg Lys Val Ser Gly Gly Gly Ser Arg
                405                 410                 415

Glu Gly Val Glu Leu Cys Pro Gly Asn Lys Tyr Glu Met Arg Arg His
                420                 425                 430

Gly Thr Thr His Ser Leu Val Ile His Asp
                435                 440

<210> SEQ ID NO 42
<211> LENGTH: 666
<212> TYPE: PRT
<213> ORGANISM: Artificial Sequence
<220> FEATURE:
<223> OTHER INFORMATION: Construct

<400> SEQUENCE: 42

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Ile Glu Pro Lys Ser Cys Asp
            100                 105                 110

Thr Pro Pro Pro Cys Pro Arg Cys Pro Gly Gly Gly Ser Ser Gly Gly
        115                 120                 125

Gly Ser Gly Gly Gln Pro Arg Glu Pro Gln Val Tyr Thr Leu Pro Pro
    130                 135                 140
```

```
Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Ser Gly
                165                 170                 175

Gln Pro Glu Asn Asn Tyr Asn Thr Thr Pro Pro Met Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Ile Phe Ser Cys Ser Val Met His Glu Ala Leu His
210                 215                 220

Asn Arg Phe Thr Gln Lys Ser Leu Ser Leu Ser Pro Gly Lys Gly Leu
225                 230                 235                 240

Gly Gly Leu Met His Gly Asp Thr Pro Thr Leu His Glu Tyr Met Leu
                245                 250                 255

Asp Leu Gln Pro Glu Thr Thr Asp Leu Tyr Gly Tyr Gly Gln Leu Asn
            260                 265                 270

Asp Ser Ser Glu Glu Glu Asp Glu Ile Asp Gly Pro Ala Gly Gln Ala
        275                 280                 285

Glu Pro Asp Arg Ala His Tyr Asn Ile Val Thr Phe Cys Cys Lys Cys
    290                 295                 300

Asp Ser Thr Leu Arg Leu Cys Val Gln Ser Thr His Val Asp Ile Arg
305                 310                 315                 320

Thr Leu Glu Asp Leu Leu Met Gly Thr Leu Gly Ile Val Cys Pro Ile
                325                 330                 335

Cys Ser Gln Lys Pro Gly Gly Gly Ser Ser Gly Gly Gly Ser Gly Pro
            340                 345                 350

Ser Lys Pro Ser Phe Gln Glu Phe Val Asp Trp Glu Asn Val Ser Pro
        355                 360                 365

Glu Leu Asn Ser Thr Asp Gln Pro Phe Leu Gly Gly Gly Gly Ser Arg
    370                 375                 380

Glu Gly Val Glu Leu Cys Pro Gly Asn Lys Tyr Glu Met Arg Arg His
385                 390                 395                 400

Gly Thr Thr His Ser Leu Val Ile His Asp Gly Gly Gly Gly Ser Ser
                405                 410                 415

His Cys His Trp Asn Asp Leu Ala Val Ile Pro Ala Gly Val Val His
            420                 425                 430

Asn Trp Asp Phe Glu Pro Arg Lys Val Ser Gly Gly Gly Gly Ser Gly
        435                 440                 445

Arg Gly His Leu Leu Gly Arg Leu Ala Ala Ile Val Gly Lys Gln Val
        450                 455                 460

Leu Leu Gly Arg Lys Val Val Val Arg Gly Gly Gly Gly Gly Ser Ala
465                 470                 475                 480

Asn Phe Glu Ser Gly Lys His Lys Tyr Arg Gln Thr Ala Met Phe Thr
            485                 490                 495

Ala Thr Met Pro Pro Ala Val Glu Arg Leu Gly Gly Gly Gly Ser Val
        500                 505                 510

Val Asp Arg Asn Pro Gln Phe Leu Asp Pro Val Leu Ala Tyr Leu Met
        515                 520                 525

Lys Gly Leu Cys Glu Lys Pro Leu Ala Ser Gly Gly Gly Gly Ser Ser
        530                 535                 540

Ser Pro Asp Glu Val Ala Leu Val Glu Gly Val Gln Ser Leu Gly Phe
545                 550                 555                 560
```

```
Thr Tyr Leu Arg Leu Lys Asp Asn Tyr Met Gly Gly Gly Ser Glu
                565                 570                 575

Phe Lys His Ile Lys Ala Phe Asp Arg Thr Phe Ala Asn Asn Pro Gly
            580                 585                 590

Pro Met Val Val Phe Ala Thr Pro Gly Met Gly Gly Gly Ser Ser
        595                 600                 605

Thr Ala Asn Tyr Asn Thr Ser His Leu Asn Asn Asp Val Trp Gln Ile
    610                 615                 620

Phe Glu Asn Pro Val Asp Trp Lys Glu Lys Gly Gly Gly Ser Asp
625                 630                 635                 640

Ser Gly Ser Pro Phe Pro Ala Ala Val Ile Leu Arg Asp Ala Leu His
            645                 650                 655

Met Ala Arg Gly Leu Lys Tyr Leu His Gln
        660                 665

<210> SEQ ID NO 43
<211> LENGTH: 986
<212> TYPE: PRT
<213> ORGANISM: Artificial Sequence
<220> FEATURE:
<223> OTHER INFORMATION: Construct

<400> SEQUENCE: 43

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
            35                  40                  45

Ala Asp Tyr Phe Glu Thr Ser Ser Gln Cys Ser Lys Pro Ser Val Ile
        50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Ile Glu Pro Lys Ser Cys Asp
                100                 105                 110

Thr Pro Pro Pro Cys Pro Arg Cys Pro Gly Gly Gly Ser Ser Gly Gly
            115                 120                 125

Gly Ser Gly Gly Gln Pro Arg Glu Pro Gln Val Tyr Thr Leu Pro Pro
        130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Ser Gly
                165                 170                 175

Gln Pro Glu Asn Asn Tyr Asn Thr Thr Pro Pro Met Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Ile Phe Ser Cys Ser Val Met His Glu Ala Leu His
    210                 215                 220

Asn Arg Phe Thr Gln Lys Ser Leu Ser Leu Ser Pro Gly Lys Gly Leu
225                 230                 235                 240

Gly Gly Leu Met His Gly Asp Thr Pro Thr Leu His Glu Tyr Met Leu
                245                 250                 255
```

-continued

```
Asp Leu Gln Pro Glu Thr Thr Asp Leu Tyr Gly Tyr Gly Gln Leu Asn
            260                 265                 270

Asp Ser Ser Glu Glu Glu Asp Glu Ile Asp Gly Pro Ala Gly Gln Ala
        275                 280                 285

Glu Pro Asp Arg Ala His Tyr Asn Ile Val Thr Phe Cys Cys Lys Cys
    290                 295                 300

Asp Ser Thr Leu Arg Leu Cys Val Gln Ser Thr His Val Asp Ile Arg
305                 310                 315                 320

Thr Leu Glu Asp Leu Leu Met Gly Thr Leu Gly Ile Val Cys Pro Ile
            325                 330                 335

Cys Ser Gln Lys Pro Gly Gly Gly Ser Ser Gly Gly Gly Ser Gly Pro
        340                 345                 350

Ser Lys Pro Ser Phe Gln Glu Phe Val Asp Trp Glu Asn Val Ser Pro
    355                 360                 365

Glu Leu Asn Ser Thr Asp Gln Pro Phe Leu Gly Gly Gly Gly Ser Arg
        370                 375                 380

Glu Gly Val Glu Leu Cys Pro Gly Asn Lys Tyr Glu Met Arg Arg His
385                 390                 395                 400

Gly Thr Thr His Ser Leu Val Ile His Asp Gly Gly Gly Gly Ser Ser
            405                 410                 415

His Cys His Trp Asn Asp Leu Ala Val Ile Pro Ala Gly Val Val His
            420                 425                 430

Asn Trp Asp Phe Glu Pro Arg Lys Val Ser Gly Gly Gly Gly Ser Gly
        435                 440                 445

Arg Gly His Leu Leu Gly Arg Leu Ala Ala Ile Val Gly Lys Gln Val
    450                 455                 460

Leu Leu Gly Arg Lys Val Val Val Arg Gly Gly Gly Gly Ser Ala
465                 470                 475                 480

Asn Phe Glu Ser Gly Lys His Lys Tyr Arg Gln Thr Ala Met Phe Thr
            485                 490                 495

Ala Thr Met Pro Pro Ala Val Glu Arg Leu Gly Gly Gly Gly Ser Val
        500                 505                 510

Val Asp Arg Asn Pro Gln Phe Leu Asp Pro Val Leu Ala Tyr Leu Met
    515                 520                 525

Lys Gly Leu Cys Glu Lys Pro Leu Ala Ser Gly Gly Gly Gly Ser Ser
530                 535                 540

Ser Pro Asp Glu Val Ala Leu Val Glu Gly Val Gln Ser Leu Gly Phe
545                 550                 555                 560

Thr Tyr Leu Arg Leu Lys Asp Asn Tyr Met Gly Gly Gly Gly Ser Glu
            565                 570                 575

Phe Lys His Ile Lys Ala Phe Asp Arg Thr Phe Ala Asn Asn Pro Gly
        580                 585                 590

Pro Met Val Val Phe Ala Thr Pro Gly Met Gly Gly Gly Gly Ser Ser
    595                 600                 605

Thr Ala Asn Tyr Asn Thr Ser His Leu Asn Asn Asp Val Trp Gln Ile
    610                 615                 620

Phe Glu Asn Pro Val Asp Trp Lys Glu Lys Gly Gly Gly Gly Ser Asp
625                 630                 635                 640

Ser Gly Ser Pro Phe Pro Ala Ala Val Ile Leu Arg Asp Ala Leu His
            645                 650                 655

Met Ala Arg Gly Leu Lys Tyr Leu His Gln Gly Gly Gly Gly Ser Pro
        660                 665                 670

Ser Lys Pro Ser Phe Gln Glu Phe Val Asp Trp Glu Asn Val Ser Pro
```

```
              675                 680                 685
Glu Leu Asn Ser Thr Asp Gln Pro Phe Leu Gly Gly Gly Gly Ser Arg
690                 695                 700
Glu Gly Val Glu Leu Cys Pro Gly Asn Lys Tyr Glu Met Arg Arg His
705                 710                 715                 720
Gly Thr Thr His Ser Leu Val Ile His Asp Gly Gly Gly Gly Ser Ser
                725                 730                 735
His Cys His Trp Asn Asp Leu Ala Val Ile Pro Ala Gly Val Val His
            740                 745                 750
Asn Trp Asp Phe Glu Pro Arg Lys Val Ser Gly Gly Gly Ser Gly
        755                 760                 765
Arg Gly His Leu Leu Gly Arg Leu Ala Ala Ile Val Gly Lys Gln Val
770                 775                 780
Leu Leu Gly Arg Lys Val Val Val Arg Gly Gly Gly Ser Ala
785                 790                 795                 800
Asn Phe Glu Ser Gly Lys His Lys Tyr Arg Gln Thr Ala Met Phe Thr
                805                 810                 815
Ala Thr Met Pro Pro Ala Val Glu Arg Leu Gly Gly Gly Ser Val
            820                 825                 830
Val Asp Arg Asn Pro Gln Phe Leu Asp Pro Val Leu Ala Tyr Leu Met
        835                 840                 845
Lys Gly Leu Cys Glu Lys Pro Leu Ala Ser Gly Gly Gly Ser Ser
850                 855                 860
Ser Pro Asp Glu Val Ala Leu Val Glu Val Gln Ser Leu Gly Phe
865                 870                 875                 880
Thr Tyr Leu Arg Leu Lys Asp Asn Tyr Met Gly Gly Gly Ser Glu
                885                 890                 895
Phe Lys His Ile Lys Ala Phe Asp Arg Thr Phe Ala Asn Asn Pro Gly
            900                 905                 910
Pro Met Val Val Phe Ala Thr Pro Gly Met Gly Gly Gly Ser Ser
        915                 920                 925
Thr Ala Asn Tyr Asn Thr Ser His Leu Asn Asn Asp Val Trp Gln Ile
930                 935                 940
Phe Glu Asn Pro Val Asp Trp Lys Glu Lys Gly Gly Gly Gly Ser Asp
945                 950                 955                 960
Ser Gly Ser Pro Phe Pro Ala Ala Val Ile Leu Arg Asp Ala Leu His
                965                 970                 975
Met Ala Arg Gly Leu Lys Tyr Leu His Gln
            980                 985

<210> SEQ ID NO 44
<211> LENGTH: 666
<212> TYPE: PRT
<213> ORGANISM: Artificial Sequence
<220> FEATURE:
<223> OTHER INFORMATION: Construct

<400> SEQUENCE: 44

Met Gln Val Ser Thr Ala Ala Leu Ala Val Leu Leu Cys Thr Met Ala
1               5                   10                  15
Leu Cys Asn Gln Val Leu Ser Ala Pro Leu Ala Ala Asp Thr Pro Thr
                20                  25                  30
Ala Cys Cys Phe Ser Tyr Thr Ser Arg Gln Ile Pro Gln Asn Phe Ile
            35                  40                  45
Ala Asp Tyr Phe Glu Thr Ser Ser Gln Cys Ser Lys Pro Ser Val Ile
```

```
                50                  55                  60
Phe Leu Thr Lys Arg Gly Arg Gln Val Cys Ala Asp Pro Ser Glu Glu
 65                  70                  75                  80

Trp Val Gln Lys Tyr Val Ser Asp Leu Glu Leu Ser Ala Glu Leu Lys
                 85                  90                  95

Thr Pro Leu Gly Asp Thr Thr His Thr Ile Glu Pro Lys Ser Cys Asp
                100                 105                 110

Thr Pro Pro Pro Cys Pro Arg Cys Pro Gly Gly Ser Ser Gly Gly
            115                 120                 125

Gly Ser Gly Gly Gln Pro Arg Glu Pro Gln Val Tyr Thr Leu Pro Pro
            130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Ser Gly
                165                 170                 175

Gln Pro Glu Asn Asn Tyr Asn Thr Thr Pro Pro Met Leu Asp Ser Asp
                180                 185                 190

Gly Ser Phe Phe Leu Tyr Ser Lys Leu Thr Val Asp Lys Ser Arg Trp
            195                 200                 205

Gln Gln Gly Asn Ile Phe Ser Cys Ser Val Met His Glu Ala Leu His
            210                 215                 220

Asn Arg Phe Thr Gln Lys Ser Leu Ser Leu Ser Pro Gly Lys Gly Leu
225                 230                 235                 240

Gly Gly Leu Met His Gly Asp Thr Pro Thr Leu His Glu Tyr Met Leu
                245                 250                 255

Asp Leu Gln Pro Glu Thr Thr Asp Leu Tyr Gly Tyr Gly Gln Leu Asn
                260                 265                 270

Asp Ser Ser Glu Glu Glu Asp Glu Ile Asp Gly Pro Ala Gly Gln Ala
            275                 280                 285

Glu Pro Asp Arg Ala His Tyr Asn Ile Val Thr Phe Cys Cys Lys Cys
290                 295                 300

Asp Ser Thr Leu Arg Leu Cys Val Gln Ser Thr His Val Asp Ile Arg
305                 310                 315                 320

Thr Leu Glu Asp Leu Leu Met Gly Thr Leu Gly Ile Val Cys Pro Ile
                325                 330                 335

Cys Ser Gln Lys Pro Gly Gly Gly Ser Ser Gly Gly Ser Gly Ser
            340                 345                 350

His Cys His Trp Asn Asp Leu Ala Val Ile Pro Ala Gly Val Val His
            355                 360                 365

Asn Trp Asp Phe Glu Pro Arg Lys Val Ser Gly Gly Gly Ser Gly
            370                 375                 380

Arg Gly His Leu Leu Gly Arg Leu Ala Ala Ile Val Gly Lys Gln Val
385                 390                 395                 400

Leu Leu Gly Arg Lys Val Val Val Arg Gly Gly Gly Gly Ser Ser
                405                 410                 415

Ser Pro Asp Glu Val Ala Leu Val Glu Gly Val Gln Ser Leu Gly Phe
                420                 425                 430

Thr Tyr Leu Arg Leu Lys Asp Asn Tyr Met Gly Gly Gly Ser Ser
            435                 440                 445

Thr Ala Asn Tyr Asn Thr Ser His Leu Asn Asn Asp Val Trp Gln Ile
            450                 455                 460

Phe Glu Asn Pro Val Asp Trp Lys Glu Lys Gly Gly Gly Gly Ser Asp
465                 470                 475                 480
```

```
Ser Gly Ser Pro Phe Pro Ala Ala Val Ile Leu Arg Asp Ala Leu His
            485                 490                 495

Met Ala Arg Gly Leu Lys Tyr Leu His Gln Gly Gly Gly Ser Ser
            500                 505                 510

His Cys His Trp Asn Asp Leu Ala Val Ile Pro Ala Gly Val Val His
            515                 520                 525

Asn Trp Asp Phe Glu Pro Arg Lys Val Ser Gly Gly Gly Ser Gly
    530                 535                 540

Arg Gly His Leu Leu Gly Arg Leu Ala Ala Ile Val Gly Lys Gln Val
545                 550                 555                 560

Leu Leu Gly Arg Lys Val Val Val Arg Gly Gly Gly Ser Ser
                565                 570                 575

Ser Pro Asp Glu Val Ala Leu Val Glu Gly Val Gln Ser Leu Gly Phe
            580                 585                 590

Thr Tyr Leu Arg Leu Lys Asp Asn Tyr Met Gly Gly Gly Ser Ser
            595                 600                 605

Thr Ala Asn Tyr Asn Thr Ser His Leu Asn Asn Asp Val Trp Gln Ile
            610                 615                 620

Phe Glu Asn Pro Val Asp Trp Lys Glu Lys Gly Gly Gly Ser Asp
625                 630                 635                 640

Ser Gly Ser Pro Phe Pro Ala Ala Val Ile Leu Arg Asp Ala Leu His
            645                 650                 655

Met Ala Arg Gly Leu Lys Tyr Leu His Gln
            660                 665

<210> SEQ ID NO 45
<211> LENGTH: 826
<212> TYPE: PRT
<213> ORGANISM: Artificial Sequence
<220> FEATURE:
<223> OTHER INFORMATION: Construct

<400> SEQUENCE: 45

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
            35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Ile Glu Pro Lys Ser Cys Asp
            100                 105                 110

Thr Pro Pro Pro Cys Pro Arg Cys Pro Gly Gly Gly Ser Gly Gly
            115                 120                 125

Gly Ser Gly Gly Gln Pro Arg Glu Pro Gln Val Tyr Thr Leu Pro Pro
    130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Ser Gly
                165                 170                 175
```

```
Gln Pro Glu Asn Asn Tyr Asn Thr Thr Pro Met Leu Asp Ser Asp
                180                 185                 190

Gly Ser Phe Phe Leu Tyr Ser Lys Leu Thr Val Asp Lys Ser Arg Trp
            195                 200                 205

Gln Gln Gly Asn Ile Phe Ser Cys Ser Val Met His Glu Ala Leu His
210                 215                 220

Asn Arg Phe Thr Gln Lys Ser Leu Ser Leu Ser Pro Gly Lys Gly Leu
225                 230                 235                 240

Gly Gly Leu Met His Gly Asp Thr Pro Thr Leu His Glu Tyr Met Leu
                245                 250                 255

Asp Leu Gln Pro Glu Thr Thr Asp Leu Tyr Gly Tyr Gly Gln Leu Asn
            260                 265                 270

Asp Ser Ser Glu Glu Glu Asp Glu Ile Asp Gly Pro Ala Gly Gln Ala
            275                 280                 285

Glu Pro Asp Arg Ala His Tyr Asn Ile Val Thr Phe Cys Cys Lys Cys
            290                 295                 300

Asp Ser Thr Leu Arg Leu Cys Val Gln Ser Thr His Val Asp Ile Arg
305                 310                 315                 320

Thr Leu Glu Asp Leu Leu Met Gly Thr Leu Gly Ile Val Cys Pro Ile
                325                 330                 335

Cys Ser Gln Lys Pro Gly Gly Gly Ser Ser Gly Gly Gly Ser Gly Ser
                340                 345                 350

His Cys His Trp Asn Asp Leu Ala Val Ile Pro Ala Gly Val Val His
            355                 360                 365

Asn Trp Asp Phe Glu Pro Arg Lys Val Ser Gly Gly Gly Ser Gly
            370                 375                 380

Arg Gly His Leu Leu Gly Arg Leu Ala Ala Ile Val Gly Lys Gln Val
385                 390                 395                 400

Leu Leu Gly Arg Lys Val Val Val Arg Gly Gly Gly Ser Ser
                405                 410                 415

Ser Pro Asp Glu Val Ala Leu Val Glu Gly Val Gln Ser Leu Gly Phe
            420                 425                 430

Thr Tyr Leu Arg Leu Lys Asp Asn Tyr Met Gly Gly Gly Ser Ser
                435                 440                 445

Thr Ala Asn Tyr Asn Thr Ser His Leu Asn Asn Asp Val Trp Gln Ile
            450                 455                 460

Phe Glu Asn Pro Val Asp Trp Lys Glu Lys Gly Gly Gly Ser Asp
465                 470                 475                 480

Ser Gly Ser Pro Phe Pro Ala Ala Val Ile Leu Arg Asp Ala Leu His
                485                 490                 495

Met Ala Arg Gly Leu Lys Tyr Leu His Gln Gly Gly Gly Ser Ser
                500                 505                 510

His Cys His Trp Asn Asp Leu Ala Val Ile Pro Ala Gly Val Val His
            515                 520                 525

Asn Trp Asp Phe Glu Pro Arg Lys Val Ser Gly Gly Gly Ser Gly
            530                 535                 540

Arg Gly His Leu Leu Gly Arg Leu Ala Ala Ile Val Gly Lys Gln Val
545                 550                 555                 560

Leu Leu Gly Arg Lys Val Val Val Arg Gly Gly Gly Ser Ser
                565                 570                 575

Ser Pro Asp Glu Val Ala Leu Val Glu Gly Val Gln Ser Leu Gly Phe
            580                 585                 590
```

```
Thr Tyr Leu Arg Leu Lys Asp Asn Tyr Met Gly Gly Gly Ser Ser
            595                 600                 605

Thr Ala Asn Tyr Asn Thr Ser His Leu Asn Asn Asp Val Trp Gln Ile
610                 615                 620

Phe Glu Asn Pro Val Asp Trp Lys Glu Lys Gly Gly Gly Ser Asp
625                 630                 635                 640

Ser Gly Ser Pro Phe Pro Ala Ala Val Ile Leu Arg Asp Ala Leu His
            645                 650                 655

Met Ala Arg Gly Leu Lys Tyr Leu His Gln Gly Gly Gly Ser Ser
            660                 665                 670

His Cys His Trp Asn Asp Leu Ala Val Ile Pro Ala Gly Val Val His
            675                 680                 685

Asn Trp Asp Phe Glu Pro Arg Lys Val Ser Gly Gly Gly Ser Gly
            690                 695                 700

Arg Gly His Leu Leu Gly Arg Leu Ala Ala Ile Val Gly Lys Gln Val
705                 710                 715                 720

Leu Leu Gly Arg Lys Val Val Val Arg Gly Gly Gly Ser Ser
            725                 730                 735

Ser Pro Asp Glu Val Ala Leu Val Glu Gly Val Gln Ser Leu Gly Phe
            740                 745                 750

Thr Tyr Leu Arg Leu Lys Asp Asn Tyr Met Gly Gly Gly Ser Ser
            755                 760                 765

Thr Ala Asn Tyr Asn Thr Ser His Leu Asn Asn Asp Val Trp Gln Ile
            770                 775                 780

Phe Glu Asn Pro Val Asp Trp Lys Glu Lys Gly Gly Gly Ser Asp
785                 790                 795                 800

Ser Gly Ser Pro Phe Pro Ala Ala Val Ile Leu Arg Asp Ala Leu His
            805                 810                 815

Met Ala Arg Gly Leu Lys Tyr Leu His Gln
            820                 825

<210> SEQ ID NO 46
<211> LENGTH: 896
<212> TYPE: PRT
<213> ORGANISM: Artificial Sequence
<220> FEATURE:
<223> OTHER INFORMATION: VB construct

<400> SEQUENCE: 46

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
            35                  40                  45

Ala Asp Tyr Phe Glu Thr Ser Ser Gln Cys Ser Lys Pro Ser Val Ile
50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Ile Glu Pro Lys Ser Cys Asp
                100                 105                 110

Thr Pro Pro Pro Cys Pro Arg Cys Pro Gly Gly Ser Ser Gly Gly
            115                 120                 125
```

-continued

```
Gly Ser Gly Gly Gln Pro Arg Glu Pro Gln Val Tyr Thr Leu Pro Pro
    130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Ser Gly
                165                 170                 175

Gln Pro Glu Asn Asn Tyr Asn Thr Thr Pro Pro Met Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Ile Phe Ser Cys Ser Val Met His Glu Ala Leu His
    210                 215                 220

Asn Arg Phe Thr Gln Lys Ser Leu Ser Leu Ser Pro Gly Lys Gly Leu
225                 230                 235                 240

Gly Gly Leu Met His Gly Asp Thr Pro Thr Leu His Glu Tyr Met Leu
                245                 250                 255

Asp Leu Gln Pro Glu Thr Thr Asp Leu Tyr Gly Tyr Gly Gln Leu Asn
            260                 265                 270

Asp Ser Ser Glu Glu Asp Glu Ile Asp Gly Pro Ala Gly Gln Ala
        275                 280                 285

Glu Pro Asp Arg Ala His Tyr Asn Ile Val Thr Phe Cys Cys Lys Cys
    290                 295                 300

Asp Ser Thr Leu Arg Leu Cys Val Gln Ser Thr His Val Asp Ile Arg
305                 310                 315                 320

Thr Leu Glu Asp Leu Leu Met Gly Thr Leu Gly Ile Val Cys Pro Ile
                325                 330                 335

Cys Ser Gln Lys Pro Gly Gly Ser Ser Gly Gly Gly Ser Gly Pro
            340                 345                 350

Ser Lys Pro Ser Phe Gln Glu Phe Val Asp Trp Glu Asn Val Ser Pro
        355                 360                 365

Glu Leu Asn Ser Thr Asp Gln Pro Phe Leu Gly Gly Gly Ser Gly
    370                 375                 380

Gly Gly Gly Ser Arg Glu Gly Val Glu Leu Cys Pro Gly Asn Lys Tyr
385                 390                 395                 400

Glu Met Arg Arg His Gly Thr Thr His Ser Leu Val Ile His Asp Gly
                405                 410                 415

Gly Gly Gly Ser Gly Gly Gly Ser Ser His Cys His Trp Asn Asp
            420                 425                 430

Leu Ala Val Ile Pro Ala Gly Val Val His Asn Trp Asp Phe Glu Pro
        435                 440                 445

Arg Lys Val Ser Gly Gly Gly Ser Gly Gly Gly Ser Gly Arg
450                 455                 460

Gly His Leu Leu Gly Arg Leu Ala Ala Ile Val Gly Lys Gln Val Leu
465                 470                 475                 480

Leu Gly Arg Lys Val Val Val Arg Gly Gly Gly Ser Gly Gly
                485                 490                 495

Gly Gly Ser Phe Arg Arg Lys Ala Phe Leu His Trp Tyr Thr Gly Glu
            500                 505                 510

Ala Met Asp Glu Met Glu Phe Thr Glu Ala Glu Ser Asn Met Gly Gly
        515                 520                 525

Gly Gly Ser Gly Gly Gly Ser Val Val Asp Arg Asn Pro Gln Phe
    530                 535                 540

Leu Asp Pro Val Leu Ala Tyr Leu Met Lys Gly Leu Cys Glu Lys Pro
```

```
            545                 550                 555                 560
Leu Ala Ser Gly Gly Gly Ser Gly Gly Gly Ser Ser Pro
                565                 570                 575

Asp Glu Val Ala Leu Val Glu Gly Val Gln Ser Leu Gly Phe Thr Tyr
                580                 585                 590

Leu Arg Leu Lys Asp Asn Tyr Met Gly Gly Gly Ser Gly Gly Gly
                595                 600                 605

Gly Ser Glu Phe Lys His Ile Lys Ala Phe Asp Arg Thr Phe Ala Asn
    610                 615                 620

Asn Pro Gly Pro Met Val Val Phe Ala Thr Pro Gly Met Gly Gly
625                 630                 635                 640

Gly Ser Gly Gly Gly Ser Ser Thr Ala Asn Tyr Asn Thr Ser His
                645                 650                 655

Leu Asn Asn Asp Val Trp Gln Ile Phe Glu Asn Pro Val Asp Trp Lys
                660                 665                 670

Glu Lys Gly Gly Gly Ser Gly Gly Gly Ser Asp Ser Gly Ser
            675                 680                 685

Pro Phe Pro Ala Ala Val Ile Leu Arg Asp Ala Leu His Met Ala Arg
    690                 695                 700

Gly Leu Lys Tyr Leu His Gln Gly Gly Gly Ser Gly Gly Gly Gly
705                 710                 715                 720

Ser Ala Asn Phe Glu Ser Gly Lys His Lys Tyr Arg Gln Thr Ala Met
                725                 730                 735

Phe Thr Ala Thr Met Pro Pro Ala Val Glu Arg Leu Gly Gly Gly Gly
                740                 745                 750

Ser Gly Gly Gly Gly Ser Asn His Ser Gly Leu Val Thr Phe Gln Ala
            755                 760                 765

Phe Ile Asp Val Met Ser Arg Glu Thr Thr Asp Thr Asp Thr Ala Asp
        770                 775                 780

Gln Gly Gly Gly Ser Gly Gly Gly Gly Ser Cys Gly Thr Ala Phe
785                 790                 795                 800

Phe Ile Asn Phe Ile Ala Ile Tyr His His Ala Ser Arg Ala Ile Pro
                805                 810                 815

Phe Gly Thr Met Val Ala Gly Gly Gly Ser Gly Gly Gly Gly Ser
                820                 825                 830

Phe Val Val Lys Ala Tyr Leu Pro Val Asn Glu Ser Phe Ala Phe Thr
            835                 840                 845

Ala Asp Leu Arg Ser Asn Thr Gly Gln Ala Gly Gly Gly Gly Ser
    850                 855                 860

Gly Gly Gly Gly Ser Thr Pro Pro Glu Glu Ala Met Pro Phe Glu
865                 870                 875                 880

Phe Asn Gly Pro Ala Gln Gly Asp His Ser Gln Pro Pro Leu Gln Val
                885                 890                 895

<210> SEQ ID NO 47
<211> LENGTH: 1081
<212> TYPE: PRT
<213> ORGANISM: Artificial Sequence
<220> FEATURE:
<223> OTHER INFORMATION: VB vector

<400> SEQUENCE: 47

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
```

```
                20                  25                  30
Ala Cys Cys Phe Ser Tyr Thr Ser Arg Gln Ile Pro Gln Asn Phe Ile
            35                  40                  45
Ala Asp Tyr Phe Glu Thr Ser Ser Gln Cys Ser Lys Pro Ser Val Ile
        50                  55                  60
Phe Leu Thr Lys Arg Gly Arg Gln Val Cys Ala Asp Pro Ser Glu Glu
65                  70                  75                  80
Trp Val Gln Lys Tyr Val Ser Asp Leu Glu Leu Ser Ala Glu Leu Lys
                85                  90                  95
Thr Pro Leu Gly Asp Thr Thr His Thr Ile Glu Pro Lys Ser Cys Asp
            100                 105                 110
Thr Pro Pro Pro Cys Pro Arg Cys Pro Gly Gly Ser Gly Gly Gly Gly
        115                 120                 125
Gly Ser Gly Gly Gln Pro Arg Glu Pro Gln Val Tyr Thr Leu Pro Pro
        130                 135                 140
Ser Arg Glu Glu Met Thr Lys Asn Gln Val Ser Leu Thr Cys Leu Val
145                 150                 155                 160
Lys Gly Phe Tyr Pro Ser Asp Ile Ala Val Glu Trp Glu Ser Ser Gly
                165                 170                 175
Gln Pro Glu Asn Asn Tyr Asn Thr Thr Pro Pro Met Leu Asp Ser Asp
            180                 185                 190
Gly Ser Phe Phe Leu Tyr Ser Lys Leu Thr Val Asp Lys Ser Arg Trp
        195                 200                 205
Gln Gln Gly Asn Ile Phe Ser Cys Ser Val Met His Glu Ala Leu His
        210                 215                 220
Asn Arg Phe Thr Gln Lys Ser Leu Ser Leu Ser Pro Gly Lys Gly Leu
225                 230                 235                 240
Gly Gly Leu Met His Gly Asp Thr Pro Thr Leu His Glu Tyr Met Leu
                245                 250                 255
Asp Leu Gln Pro Glu Thr Thr Asp Leu Tyr Gly Tyr Gly Gln Leu Asn
            260                 265                 270
Asp Ser Ser Glu Glu Glu Asp Glu Ile Asp Gly Pro Ala Gly Gln Ala
        275                 280                 285
Glu Pro Asp Arg Ala His Tyr Asn Ile Val Thr Phe Cys Cys Lys Cys
        290                 295                 300
Asp Ser Thr Leu Arg Leu Cys Val Gln Ser Thr His Val Asp Ile Arg
305                 310                 315                 320
Thr Leu Glu Asp Leu Leu Met Gly Thr Leu Gly Ile Val Cys Pro Ile
                325                 330                 335
Cys Ser Gln Lys Pro Gly Gly Ser Ser Gly Gly Ser Gly Pro
            340                 345                 350
Ser Lys Pro Ser Phe Gln Glu Phe Val Asp Trp Glu Asn Val Ser Pro
            355                 360                 365
Glu Leu Asn Ser Thr Asp Gln Pro Phe Leu Gly Gly Gly Ser Gly
        370                 375                 380
Gly Gly Gly Ser Arg Glu Val Glu Leu Cys Pro Gly Asn Lys Tyr
385                 390                 395                 400
Glu Met Arg Arg His Gly Thr Thr His Ser Leu Val Ile His Asp Gly
                405                 410                 415
Gly Gly Gly Ser Gly Gly Gly Ser Ser His Cys His Trp Asn Asp
            420                 425                 430
Leu Ala Val Ile Pro Ala Gly Val Val His Asn Trp Asp Phe Glu Pro
            435                 440                 445
```

```
Arg Lys Val Ser Gly Gly Gly Ser Gly Gly Gly Ser Gly Arg
450                 455                 460

Gly His Leu Leu Gly Arg Leu Ala Ala Ile Val Gly Lys Gln Val Leu
465                 470                 475                 480

Leu Gly Arg Lys Val Val Val Arg Gly Gly Gly Ser Gly Gly
            485                 490                 495

Gly Gly Ser Phe Arg Arg Lys Ala Phe Leu His Trp Tyr Thr Gly Glu
                500                 505                 510

Ala Met Asp Glu Met Glu Phe Thr Glu Ala Glu Ser Asn Met Gly Gly
            515                 520                 525

Gly Gly Ser Gly Gly Gly Ser Val Val Asp Arg Asn Pro Gln Phe
            530                 535                 540

Leu Asp Pro Val Leu Ala Tyr Leu Met Lys Gly Leu Cys Glu Lys Pro
545                 550                 555                 560

Leu Ala Ser Gly Gly Gly Ser Gly Gly Gly Ser Ser Ser Pro
                565                 570                 575

Asp Glu Val Ala Leu Val Glu Gly Val Gln Ser Leu Gly Phe Thr Tyr
                580                 585                 590

Leu Arg Leu Lys Asp Asn Tyr Met Gly Gly Gly Ser Gly Gly Gly
            595                 600                 605

Gly Ser Glu Phe Lys His Ile Lys Ala Phe Asp Arg Thr Phe Ala Asn
        610                 615                 620

Asn Pro Gly Pro Met Val Val Phe Ala Thr Pro Gly Met Gly Gly Gly
625                 630                 635                 640

Gly Ser Gly Gly Gly Gly Ser Ser Thr Ala Asn Tyr Asn Thr Ser His
                645                 650                 655

Leu Asn Asn Asp Val Trp Gln Ile Phe Glu Asn Pro Val Asp Trp Lys
            660                 665                 670

Glu Lys Gly Gly Gly Gly Ser Gly Gly Gly Gly Ser Asp Ser Gly Ser
            675                 680                 685

Pro Phe Pro Ala Ala Val Ile Leu Arg Asp Ala Leu His Met Ala Arg
            690                 695                 700

Gly Leu Lys Tyr Leu His Gln Gly Gly Gly Ser Gly Gly Gly Gly
705                 710                 715                 720

Ser Ala Asn Phe Glu Ser Gly Lys His Lys Tyr Arg Gln Thr Ala Met
                725                 730                 735

Phe Thr Ala Thr Met Pro Pro Ala Val Glu Arg Leu Gly Gly Gly Gly
            740                 745                 750

Ser Gly Gly Gly Gly Ser Asn His Ser Gly Leu Val Thr Phe Gln Ala
        755                 760                 765

Phe Ile Asp Val Met Ser Arg Glu Thr Thr Asp Thr Asp Thr Ala Asp
770                 775                 780

Gln Gly Gly Gly Gly Ser Gly Gly Gly Gly Ser Cys Gly Thr Ala Phe
785                 790                 795                 800

Phe Ile Asn Phe Ile Ala Ile Tyr His His Ala Ser Arg Ala Ile Pro
                805                 810                 815

Phe Gly Thr Met Val Ala Gly Gly Gly Ser Gly Gly Gly Gly Ser
            820                 825                 830

Phe Val Val Lys Ala Tyr Leu Pro Val Asn Glu Ser Phe Ala Phe Thr
            835                 840                 845

Ala Asp Leu Arg Ser Asn Thr Gly Gly Gln Ala Gly Gly Gly Ser
850                 855                 860
```

Gly Gly Gly Gly Ser Thr Pro Pro Glu Glu Ala Met Pro Phe Glu
865                 870             875             880

Phe Asn Gly Pro Ala Gln Gly Asp His Ser Gln Pro Pro Leu Gln Val
            885             890             895

Gly Gly Gly Gly Ser Gly Gly Gly Ser Pro Lys Pro Asp Phe Ser
            900             905             910

Gln Leu Gln Arg Asn Ile Leu Pro Ser Asn Pro Arg Val Thr Arg Phe
            915             920             925

His Ile Asn Trp Asp Gly Gly Gly Ser Gly Gly Gly Ser Ile
        930             935             940

Pro Ser Gly Thr Thr Ile Leu Asn Cys Phe His Asp Val Leu Ser Gly
945             950             955             960

Lys Leu Ser Gly Gly Ser Pro Gly Val Pro Gly Gly Gly Ser Gly
            965             970             975

Gly Gly Gly Ser Gly Phe Ser Gln Pro Leu Arg Arg Leu Val Leu His
            980             985             990

Val Val Ser Ala Ala Gln Ala Glu Arg Leu Ala Arg Ala Glu Glu Gly
        995             1000            1005

Gly Gly Gly Ser Gly Gly Gly Gly Ser Glu Cys Arg Ile Thr Ser
        1010            1015            1020

Asn Phe Val Ile Pro Ser Glu Tyr Trp Val Glu Lys Glu Glu
        1025            1030            1035

Lys Gln Lys Leu Ile Gln Gly Gly Gly Ser Gly Gly Gly Gly
        1040            1045            1050

Ser Asn Ile Glu Gly Ile Asp Lys Leu Thr Gln Leu Lys Lys Pro
        1055            1060            1065

Phe Leu Val Asn Asn Lys Ile Asn Lys Ile Glu Asn Ile
        1070            1075            1080

<210> SEQ ID NO 48
<211> LENGTH: 896
<212> TYPE: PRT
<213> ORGANISM: Artificial Sequence
<220> FEATURE:
<223> OTHER INFORMATION: VB construct

<400> SEQUENCE: 48

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Ile Glu Pro Lys Ser Cys Asp
            100                 105                 110

Thr Pro Pro Pro Cys Pro Arg Cys Pro Gly Gly Gly Ser Gly Gly
        115                 120                 125

Gly Ser Gly Gly Gln Pro Arg Glu Pro Gln Val Tyr Thr Leu Pro Pro
    130                 135                 140

```
Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Ser Gly
            165                 170                 175

Gln Pro Glu Asn Asn Tyr Asn Thr Thr Pro Pro Met Leu Asp Ser Asp
            180                 185                 190

Gly Ser Phe Phe Leu Tyr Ser Lys Leu Thr Val Asp Lys Ser Arg Trp
            195                 200                 205

Gln Gln Gly Asn Ile Phe Ser Cys Ser Val Met His Glu Ala Leu His
            210                 215                 220

Asn Arg Phe Thr Gln Lys Ser Leu Ser Leu Ser Pro Gly Lys Gly Leu
225                 230                 235                 240

Gly Gly Leu Met His Gly Asp Thr Pro Thr Leu His Glu Tyr Met Leu
            245                 250                 255

Asp Leu Gln Pro Glu Thr Thr Asp Leu Tyr Gly Tyr Gly Gln Leu Asn
            260                 265                 270

Asp Ser Ser Glu Glu Glu Asp Glu Ile Asp Gly Pro Ala Gly Gln Ala
            275                 280                 285

Glu Pro Asp Arg Ala His Tyr Asn Ile Val Thr Phe Cys Cys Lys Cys
290                 295                 300

Asp Ser Thr Leu Arg Leu Cys Val Gln Ser Thr His Val Asp Ile Arg
305                 310                 315                 320

Thr Leu Glu Asp Leu Leu Met Gly Thr Leu Gly Ile Val Cys Pro Ile
            325                 330                 335

Cys Ser Gln Lys Pro Gly Gly Gly Ser Ser Gly Gly Ser Gly Val
            340                 345                 350

Ile Leu Pro Gln Ala Pro Ser Gly Pro Ser Tyr Ala Thr Tyr Leu Gln
            355                 360                 365

Pro Ala Gln Ala Gln Met Leu Thr Pro Pro Gly Gly Gly Ser Gly
            370                 375                 380

Gly Gly Gly Ser Leu His Ser Gly Gln Asn His Leu Lys Glu Met Ala
385                 390                 395                 400

Ile Ser Val Leu Glu Ala Arg Ala Cys Ala Ala Ala Gly Gln Ser Gly
            405                 410                 415

Gly Gly Gly Ser Gly Gly Gly Gly Ser Pro Leu Leu Pro Phe Tyr Pro
            420                 425                 430

Pro Asp Glu Ala Leu Glu Ile Gly Leu Glu Leu Asn Ser Ser Ala Leu
            435                 440                 445

Pro Pro Thr Glu Gly Gly Gly Ser Gly Gly Gly Gly Ser Ala Gly
            450                 455                 460

Thr Gln Cys Glu Tyr Trp Ala Ser Arg Ala Leu Asp Ser Glu His Ser
465                 470                 475                 480

Ile Gly Ser Met Ile Gln Leu Pro Gln Gly Gly Gly Ser Gly Gly
            485                 490                 495

Gly Gly Ser Ala Ala Tyr Lys Gly His His Tyr Pro Gly Pro Gly Asn
            500                 505                 510

Tyr Phe Trp Lys Cys Leu Phe Met Ser Gly Leu Ser Glu Val Gly Gly
            515                 520                 525

Gly Gly Ser Gly Gly Gly Ser Asp Thr Leu Ser Ala Met Ser Asn
            530                 535                 540

Pro Arg Ala Met Gln Val Leu Leu Gln Ile Gln Gln Gly Leu Gln Thr
545                 550                 555                 560

Leu Ala Thr Gly Gly Gly Gly Ser Gly Gly Gly Gly Ser Asp Lys Pro
```

```
                565                 570                 575
Leu Arg Arg Asn Asn Ser Tyr Thr Ser Tyr Ile Met Ala Ile Cys Gly
            580                 585                 590

Met Pro Leu Asp Ser Phe Arg Ala Gly Gly Gly Ser Gly Gly Gly
        595                 600                 605

Gly Ser Glu Val Ile Gln Thr Ser Lys Tyr Tyr Met Arg Asp Val Ile
        610                 615                 620

Ala Ile Glu Ser Ala Trp Leu Leu Glu Leu Ala Pro His Gly Gly Gly
625                 630                 635                 640

Gly Ser Gly Gly Gly Gly Ser Gly Tyr Ile Ser Arg Val Thr Ala Gly
            645                 650                 655

Lys Asp Ser Tyr Ile Ala Leu Val Asp Lys Asn Ile Met Gly Tyr Ile
                660                 665                 670

Ala Ser Gly Gly Gly Gly Ser Gly Gly Gly Gly Ser Glu His Ile His
            675                 680                 685

Arg Ala Gly Gly Leu Phe Val Ala Asp Ala Ile Gln Val Gly Phe Gly
        690                 695                 700

Arg Ile Gly Lys His Phe Trp Gly Gly Gly Ser Gly Gly Gly Gly
705                 710                 715                 720

Ser Gln Ala Ile Val Arg Gly Cys Ser Met Pro Gly Pro Trp Arg Ser
                725                 730                 735

Gly Arg Leu Leu Val Ser Arg Arg Trp Ser Val Glu Gly Gly Gly
            740                 745                 750

Ser Gly Gly Gly Gly Ser Asp Gly Gln Leu Glu Leu Leu Ala Gln Gly
            755                 760                 765

Ala Leu Asp Asn Ala Leu Ser Ser Met Gly Ala Leu His Ala Leu Arg
770                 775                 780

Pro Gly Gly Gly Gly Ser Gly Gly Gly Gly Ser Ser His Asp Ser Arg
785                 790                 795                 800

Lys Ser Thr Ser Phe Met Ser Val Asn Pro Ser Lys Glu Ile Lys Ile
                805                 810                 815

Val Ser Ala Val Arg Arg Gly Gly Gly Ser Gly Gly Gly Gly Ser
                820                 825                 830

His Thr Pro Ser Ser Tyr Ile Glu Thr Leu Pro Lys Ala Ile Lys Arg
            835                 840                 845

Arg Ile Asn Ala Leu Lys Gln Leu Gln Val Arg Gly Gly Gly Gly Ser
            850                 855                 860

Gly Gly Gly Gly Ser Met Lys Ala Phe Ile Phe Lys Tyr Ser Ala Lys
865                 870                 875                 880

Thr Gly Phe Thr Lys Leu Ile Asp Ala Ser Arg Val Ser Glu Thr Glu
                885                 890                 895

<210> SEQ ID NO 49
<211> LENGTH: 1081
<212> TYPE: PRT
<213> ORGANISM: Artificial Sequence
<220> FEATURE:
<223> OTHER INFORMATION: VB construct

<400> SEQUENCE: 49

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
```

```
                35                  40                  45
Ala Asp Tyr Phe Glu Thr Ser Ser Gln Cys Ser Lys Pro Ser Val Ile
 50                  55                  60

Phe Leu Thr Lys Arg Gly Arg Gln Val Cys Ala Asp Pro Ser Glu Glu
 65                  70                  75                  80

Trp Val Gln Lys Tyr Val Ser Asp Leu Glu Leu Ser Ala Glu Leu Lys
                     85                  90                  95

Thr Pro Leu Gly Asp Thr Thr His Thr Ile Glu Pro Lys Ser Cys Asp
                100                 105                 110

Thr Pro Pro Cys Pro Arg Cys Pro Gly Gly Ser Ser Gly Gly
            115                 120                 125

Gly Ser Gly Gly Gln Pro Arg Glu Pro Gln Val Tyr Thr Leu Pro Pro
130                 135                 140

Ser Arg Glu Glu Met Thr Lys Asn Gln Val Ser Leu Thr Cys Leu Val
145                 150                 155                 160

Lys Gly Phe Tyr Pro Ser Asp Ile Ala Val Glu Trp Glu Ser Ser Gly
                165                 170                 175

Gln Pro Glu Asn Asn Tyr Asn Thr Thr Pro Pro Met Leu Asp Ser Asp
                180                 185                 190

Gly Ser Phe Phe Leu Tyr Ser Lys Leu Thr Val Asp Lys Ser Arg Trp
                195                 200                 205

Gln Gln Gly Asn Ile Phe Ser Cys Ser Val Met His Glu Ala Leu His
                210                 215                 220

Asn Arg Phe Thr Gln Lys Ser Leu Ser Leu Ser Pro Gly Lys Gly Leu
225                 230                 235                 240

Gly Gly Leu Met His Gly Asp Thr Pro Thr Leu His Glu Tyr Met Leu
                245                 250                 255

Asp Leu Gln Pro Glu Thr Thr Asp Leu Tyr Gly Tyr Gly Gln Leu Asn
                260                 265                 270

Asp Ser Ser Glu Glu Glu Asp Glu Ile Asp Gly Pro Ala Gly Gln Ala
                275                 280                 285

Glu Pro Asp Arg Ala His Tyr Asn Ile Val Thr Phe Cys Cys Lys Cys
290                 295                 300

Asp Ser Thr Leu Arg Leu Cys Val Gln Ser Thr His Val Asp Ile Arg
305                 310                 315                 320

Thr Leu Glu Asp Leu Leu Met Gly Thr Leu Gly Ile Val Cys Pro Ile
                325                 330                 335

Cys Ser Gln Lys Pro Gly Gly Ser Ser Gly Gly Ser Gly Val
                340                 345                 350

Ile Leu Pro Gln Ala Pro Ser Gly Pro Ser Tyr Ala Thr Tyr Leu Gln
                355                 360                 365

Pro Ala Gln Ala Gln Met Leu Thr Pro Pro Gly Gly Gly Gly Ser Gly
                370                 375                 380

Gly Gly Gly Ser Leu His Ser Gly Gln Asn His Leu Lys Glu Met Ala
385                 390                 395                 400

Ile Ser Val Leu Glu Ala Arg Ala Cys Ala Ala Gly Gln Ser Gly
                    405                 410                 415

Gly Gly Gly Ser Gly Gly Gly Ser Pro Leu Leu Pro Phe Tyr Pro
                420                 425                 430

Pro Asp Glu Ala Leu Glu Ile Gly Leu Glu Leu Asn Ser Ser Ala Leu
                435                 440                 445

Pro Pro Thr Glu Gly Gly Gly Ser Gly Gly Gly Ser Ala Gly
                450                 455                 460
```

```
Thr Gln Cys Glu Tyr Trp Ala Ser Arg Ala Leu Asp Ser Glu His Ser
465                 470                 475                 480

Ile Gly Ser Met Ile Gln Leu Pro Gln Gly Gly Gly Ser Gly Gly
                485                 490                 495

Gly Gly Ser Ala Ala Tyr Lys Gly His His Tyr Pro Gly Pro Gly Asn
            500                 505                 510

Tyr Phe Trp Lys Cys Leu Phe Met Ser Gly Leu Ser Glu Val Gly Gly
        515                 520                 525

Gly Gly Ser Gly Gly Gly Ser Asp Thr Leu Ser Ala Met Ser Asn
    530                 535                 540

Pro Arg Ala Met Gln Val Leu Leu Gln Ile Gln Gln Gly Leu Gln Thr
545                 550                 555                 560

Leu Ala Thr Gly Gly Gly Ser Gly Gly Gly Ser Asp Lys Pro
            565                 570                 575

Leu Arg Arg Asn Asn Ser Tyr Thr Ser Tyr Ile Met Ala Ile Cys Gly
            580                 585                 590

Met Pro Leu Asp Ser Phe Arg Ala Gly Gly Gly Ser Gly Gly Gly
        595                 600                 605

Gly Ser Glu Val Ile Gln Thr Ser Lys Tyr Tyr Met Arg Asp Val Ile
    610                 615                 620

Ala Ile Glu Ser Ala Trp Leu Leu Glu Leu Ala Pro His Gly Gly
625                 630                 635                 640

Gly Ser Gly Gly Gly Gly Ser Gly Tyr Ile Ser Arg Val Thr Ala Gly
                645                 650                 655

Lys Asp Ser Tyr Ile Ala Leu Val Asp Lys Asn Ile Met Gly Tyr Ile
            660                 665                 670

Ala Ser Gly Gly Gly Gly Ser Gly Gly Gly Ser Glu His Ile His
            675                 680                 685

Arg Ala Gly Gly Leu Phe Val Ala Asp Ala Ile Gln Val Gly Phe Gly
690                 695                 700

Arg Ile Gly Lys His Phe Trp Gly Gly Gly Ser Gly Gly Gly Gly
705                 710                 715                 720

Ser Gln Ala Ile Val Arg Gly Cys Ser Met Pro Gly Pro Trp Arg Ser
                725                 730                 735

Gly Arg Leu Leu Val Ser Arg Arg Trp Ser Val Glu Gly Gly Gly Gly
            740                 745                 750

Ser Gly Gly Gly Gly Ser Asp Gly Gln Leu Glu Leu Ala Gln Gly
    755                 760                 765

Ala Leu Asp Asn Ala Leu Ser Ser Met Gly Ala Leu His Ala Leu Arg
    770                 775                 780

Pro Gly Gly Gly Gly Ser Gly Gly Gly Gly Ser Ser His Asp Ser Arg
785                 790                 795                 800

Lys Ser Thr Ser Phe Met Ser Val Asn Pro Ser Lys Glu Ile Lys Ile
                805                 810                 815

Val Ser Ala Val Arg Arg Gly Gly Gly Gly Ser Gly Gly Gly Gly Ser
            820                 825                 830

His Thr Pro Ser Ser Tyr Ile Glu Thr Leu Pro Lys Ala Ile Lys Arg
            835                 840                 845

Arg Ile Asn Ala Leu Lys Gln Leu Gln Val Arg Gly Gly Gly Gly Ser
        850                 855                 860

Gly Gly Gly Gly Ser Met Lys Ala Phe Ile Phe Lys Tyr Ser Ala Lys
865                 870                 875                 880
```

```
Thr Gly Phe Thr Lys Leu Ile Asp Ala Ser Arg Val Ser Glu Thr Glu
            885                 890                 895

Gly Gly Gly Gly Ser Gly Gly Gly Ser Glu Gly Asp Pro Cys Leu
        900                 905                 910

Arg Ser Ser Asp Cys Ile Asp Glu Phe Cys Cys Ala Arg His Phe Trp
            915                 920                 925

Thr Lys Ile Cys Lys Gly Gly Gly Ser Gly Gly Gly Ser Trp
            930                 935                 940

Lys Gly Gly Pro Val Lys Ile Asp Pro Leu Ala Leu Met Gln Ala Ile
945                 950                 955                 960

Glu Arg Tyr Leu Val Val Arg Gly Tyr Gly Gly Gly Ser Gly
                965                 970                 975

Gly Gly Gly Ser Val Thr Ser Ile Pro Ser Val Ser Asn Ala Leu Asn
            980                 985                 990

Trp Lys Glu Phe Ser Phe Ile Gln Ser Thr Leu Gly Tyr Val Ala Gly
            995                1000                1005

Gly Gly Gly Ser Gly Gly Gly Ser Tyr Arg Gly Ala Asn Leu
        1010                1015                1020

His Leu Glu Glu Thr Leu Ala Gly Phe Trp Ala Arg Leu Leu Glu
        1025                1030                1035

Arg Leu Phe Lys Gln Leu Gly Gly Gly Ser Gly Gly Gly Gly
        1040                1045                1050

Ser Lys Thr Thr Leu Ser His Thr Gln Asp Ser Ser Gln Ser Leu
        1055                1060                1065

Gln Ser Ser Ser Asp Ser Ser Lys Ser Ser Arg Cys Ser
        1070                1075                1080

<210> SEQ ID NO 50
<211> LENGTH: 27
<212> TYPE: PRT
<213> ORGANISM: Mus musculus

<400> SEQUENCE: 50

Gln Ala Ile Val Arg Gly Cys Ser Met Pro Gly Pro Trp Arg Ser Gly
1               5                   10                  15

Arg Leu Leu Val Ser Arg Arg Trp Ser Val Glu
            20                  25

<210> SEQ ID NO 51
<211> LENGTH: 27
<212> TYPE: PRT
<213> ORGANISM: Mus musculus

<400> SEQUENCE: 51

Asp Gly Gln Leu Glu Leu Leu Ala Gln Gly Ala Leu Asp Asn Ala Leu
1               5                   10                  15

Ser Ser Met Gly Ala Leu His Ala Leu Arg Pro
            20                  25

<210> SEQ ID NO 52
<211> LENGTH: 27
<212> TYPE: PRT
<213> ORGANISM: Mus musculus

<400> SEQUENCE: 52

Ser His Asp Ser Arg Lys Ser Thr Ser Phe Met Ser Val Asn Pro Ser
1               5                   10                  15

Lys Glu Ile Lys Ile Val Ser Ala Val Arg Arg
            20                  25
```

<210> SEQ ID NO 53
<211> LENGTH: 27
<212> TYPE: PRT
<213> ORGANISM: Mus musculus

<400> SEQUENCE: 53

His Thr Pro Ser Ser Tyr Ile Glu Thr Leu Pro Lys Ala Ile Lys Arg
1               5                   10                  15

Arg Ile Asn Ala Leu Lys Gln Leu Gln Val Arg
            20                  25

<210> SEQ ID NO 54
<211> LENGTH: 27
<212> TYPE: PRT
<213> ORGANISM: Mus musculus

<400> SEQUENCE: 54

Met Lys Ala Phe Ile Phe Lys Tyr Ser Ala Lys Thr Gly Phe Thr Lys
1               5                   10                  15

Leu Ile Asp Ala Ser Arg Val Ser Glu Thr Glu
            20                  25

<210> SEQ ID NO 55
<211> LENGTH: 27
<212> TYPE: PRT
<213> ORGANISM: Mus musculus

<400> SEQUENCE: 55

Glu Gly Asp Pro Cys Leu Arg Ser Ser Asp Cys Ile Asp Glu Phe Cys
1               5                   10                  15

Cys Ala Arg His Phe Trp Thr Lys Ile Cys Lys
            20                  25

<210> SEQ ID NO 56
<211> LENGTH: 27
<212> TYPE: PRT
<213> ORGANISM: Mus musculus

<400> SEQUENCE: 56

Trp Lys Gly Gly Pro Val Lys Ile Asp Pro Leu Ala Leu Met Gln Ala
1               5                   10                  15

Ile Glu Arg Tyr Leu Val Val Arg Gly Tyr Gly
            20                  25

<210> SEQ ID NO 57
<211> LENGTH: 27
<212> TYPE: PRT
<213> ORGANISM: Mus musculus

<400> SEQUENCE: 57

Val Thr Ser Ile Pro Ser Val Ser Asn Ala Leu Asn Trp Lys Glu Phe
1               5                   10                  15

Ser Phe Ile Gln Ser Thr Leu Gly Tyr Val Ala
            20                  25

<210> SEQ ID NO 58
<211> LENGTH: 27
<212> TYPE: PRT
<213> ORGANISM: Mus musculus

<400> SEQUENCE: 58

```
Tyr Arg Gly Ala Asn Leu His Leu Glu Glu Thr Leu Ala Gly Phe Trp
1               5                   10                  15

Ala Arg Leu Leu Glu Arg Leu Phe Lys Gln Leu
            20                  25
```

<210> SEQ ID NO 59
<211> LENGTH: 27
<212> TYPE: PRT
<213> ORGANISM: Mus musculus

<400> SEQUENCE: 59

```
Lys Thr Thr Leu Ser His Thr Gln Asp Ser Ser Gln Ser Leu Gln Ser
1               5                   10                  15

Ser Ser Asp Ser Ser Lys Ser Ser Arg Cys Ser
            20                  25
```

<210> SEQ ID NO 60
<211> LENGTH: 27
<212> TYPE: PRT
<213> ORGANISM: Mus musculus

<400> SEQUENCE: 60

```
Asn His Ser Gly Leu Val Thr Phe Gln Ala Phe Ile Asp Val Met Ser
1               5                   10                  15

Arg Glu Thr Thr Asp Thr Asp Thr Ala Asp Gln
            20                  25
```

<210> SEQ ID NO 61
<211> LENGTH: 27
<212> TYPE: PRT
<213> ORGANISM: Mus musculus

<400> SEQUENCE: 61

```
Cys Gly Thr Ala Phe Phe Ile Asn Phe Ile Ala Ile Tyr His His Ala
1               5                   10                  15

Ser Arg Ala Ile Pro Phe Gly Thr Met Val Ala
            20                  25
```

<210> SEQ ID NO 62
<211> LENGTH: 27
<212> TYPE: PRT
<213> ORGANISM: Mus musculus

<400> SEQUENCE: 62

```
Phe Val Val Lys Ala Tyr Leu Pro Val Asn Glu Ser Phe Ala Phe Thr
1               5                   10                  15

Ala Asp Leu Arg Ser Asn Thr Gly Gly Gln Ala
            20                  25
```

<210> SEQ ID NO 63
<211> LENGTH: 27
<212> TYPE: PRT
<213> ORGANISM: Mus musculus

<400> SEQUENCE: 63

```
Thr Pro Pro Pro Glu Glu Ala Met Pro Phe Glu Phe Asn Gly Pro Ala
1               5                   10                  15

Gln Gly Asp His Ser Gln Pro Pro Leu Gln Val
            20                  25
```

<210> SEQ ID NO 64

```
<211> LENGTH: 27
<212> TYPE: PRT
<213> ORGANISM: Mus musculus

<400> SEQUENCE: 64

Pro Lys Pro Asp Phe Ser Gln Leu Gln Arg Asn Ile Leu Pro Ser Asn
1               5                   10                  15

Pro Arg Val Thr Arg Phe His Ile Asn Trp Asp
            20                  25

<210> SEQ ID NO 65
<211> LENGTH: 27
<212> TYPE: PRT
<213> ORGANISM: Mus musculus

<400> SEQUENCE: 65

Ile Pro Ser Gly Thr Thr Ile Leu Asn Cys Phe His Asp Val Leu Ser
1               5                   10                  15

Gly Lys Leu Ser Gly Gly Ser Pro Gly Val Pro
            20                  25

<210> SEQ ID NO 66
<211> LENGTH: 27
<212> TYPE: PRT
<213> ORGANISM: Mus musculus

<400> SEQUENCE: 66

Gly Phe Ser Gln Pro Leu Arg Arg Leu Val Leu His Val Val Ser Ala
1               5                   10                  15

Ala Gln Ala Glu Arg Leu Ala Arg Ala Glu Glu
            20                  25

<210> SEQ ID NO 67
<211> LENGTH: 27
<212> TYPE: PRT
<213> ORGANISM: Mus musculus

<400> SEQUENCE: 67

Glu Cys Arg Ile Thr Ser Asn Phe Val Ile Pro Ser Glu Tyr Trp Val
1               5                   10                  15

Glu Glu Lys Glu Glu Lys Gln Lys Leu Ile Gln
            20                  25

<210> SEQ ID NO 68
<211> LENGTH: 27
<212> TYPE: PRT
<213> ORGANISM: Mus musculus

<400> SEQUENCE: 68

Asn Ile Glu Gly Ile Asp Lys Leu Thr Gln Leu Lys Lys Pro Phe Leu
1               5                   10                  15

Val Asn Asn Lys Ile Asn Lys Ile Glu Asn Ile
            20                  25

<210> SEQ ID NO 69
<211> LENGTH: 5
<212> TYPE: PRT
<213> ORGANISM: Artificial Sequence
<220> FEATURE:
<223> OTHER INFORMATION: Linker

<400> SEQUENCE: 69

Gly Gly Gly Ser Ser
1               5
```

```
1               5

<210> SEQ ID NO 70
<211> LENGTH: 5
<212> TYPE: PRT
<213> ORGANISM: Artificial Sequence
<220> FEATURE:
<223> OTHER INFORMATION: Linker

<400> SEQUENCE: 70

Gly Gly Gly Ser Gly
1               5

<210> SEQ ID NO 71
<211> LENGTH: 5
<212> TYPE: PRT
<213> ORGANISM: Artificial Sequence
<220> FEATURE:
<223> OTHER INFORMATION: Linker

<400> SEQUENCE: 71

Gly Gly Gly Gly Ser
1               5

<210> SEQ ID NO 72
<211> LENGTH: 5
<212> TYPE: PRT
<213> ORGANISM: Artificial Sequence
<220> FEATURE:
<223> OTHER INFORMATION: Linker

<400> SEQUENCE: 72

Leu Gly Gly Gly Ser
1               5

<210> SEQ ID NO 73
<211> LENGTH: 5
<212> TYPE: PRT
<213> ORGANISM: Artificial Sequence
<220> FEATURE:
<223> OTHER INFORMATION: Linker

<400> SEQUENCE: 73

Gly Leu Gly Gly Ser
1               5

<210> SEQ ID NO 74
<211> LENGTH: 5
<212> TYPE: PRT
<213> ORGANISM: Artificial Sequence
<220> FEATURE:
<223> OTHER INFORMATION: Linker

<400> SEQUENCE: 74

Gly Gly Leu Gly Ser
1               5

<210> SEQ ID NO 75
<211> LENGTH: 5
<212> TYPE: PRT
<213> ORGANISM: Artificial Sequence
<220> FEATURE:
<223> OTHER INFORMATION: Linker

<400> SEQUENCE: 75

Gly Gly Gly Leu Ser
1               5
```

```
<210> SEQ ID NO 76
<211> LENGTH: 5
<212> TYPE: PRT
<213> ORGANISM: Artificial Sequence
<220> FEATURE:
<223> OTHER INFORMATION: Linker

<400> SEQUENCE: 76

Gly Gly Gly Gly Leu
1               5

<210> SEQ ID NO 77
<211> LENGTH: 5
<212> TYPE: PRT
<213> ORGANISM: Artificial Sequence
<220> FEATURE:
<223> OTHER INFORMATION: Linker

<400> SEQUENCE: 77

Leu Gly Gly Ser Gly
1               5

<210> SEQ ID NO 78
<211> LENGTH: 5
<212> TYPE: PRT
<213> ORGANISM: Artificial Sequence
<220> FEATURE:
<223> OTHER INFORMATION: Linker

<400> SEQUENCE: 78

Gly Leu Gly Ser Gly
1               5

<210> SEQ ID NO 79
<211> LENGTH: 5
<212> TYPE: PRT
<213> ORGANISM: Artificial Sequence
<220> FEATURE:
<223> OTHER INFORMATION: Linker

<400> SEQUENCE: 79

Gly Gly Leu Ser Gly
1               5

<210> SEQ ID NO 80
<211> LENGTH: 5
<212> TYPE: PRT
<213> ORGANISM: Artificial Sequence
<220> FEATURE:
<223> OTHER INFORMATION: Linker

<400> SEQUENCE: 80

Gly Gly Gly Leu Gly
1               5

<210> SEQ ID NO 81
<211> LENGTH: 5
<212> TYPE: PRT
<213> ORGANISM: Artificial Sequence
<220> FEATURE:
<223> OTHER INFORMATION: Linker

<400> SEQUENCE: 81

Gly Gly Gly Ser Leu
1               5
```

```
<210> SEQ ID NO 82
<211> LENGTH: 5
<212> TYPE: PRT
<213> ORGANISM: Artificial Sequence
<220> FEATURE:
<223> OTHER INFORMATION: Linker

<400> SEQUENCE: 82

Leu Gly Gly Ser Ser
1               5

<210> SEQ ID NO 83
<211> LENGTH: 5
<212> TYPE: PRT
<213> ORGANISM: Artificial Sequence
<220> FEATURE:
<223> OTHER INFORMATION: Linker

<400> SEQUENCE: 83

Gly Leu Gly Ser Ser
1               5

<210> SEQ ID NO 84
<211> LENGTH: 5
<212> TYPE: PRT
<213> ORGANISM: Artificial Sequence
<220> FEATURE:
<223> OTHER INFORMATION: Linker

<400> SEQUENCE: 84

Gly Gly Leu Ser Ser
1               5

<210> SEQ ID NO 85
<211> LENGTH: 5
<212> TYPE: PRT
<213> ORGANISM: Artificial Sequence
<220> FEATURE:
<223> OTHER INFORMATION: Linker

<400> SEQUENCE: 85

Gly Gly Gly Leu Ser
1               5

<210> SEQ ID NO 86
<211> LENGTH: 5
<212> TYPE: PRT
<213> ORGANISM: Artificial Sequence
<220> FEATURE:
<223> OTHER INFORMATION: Linker

<400> SEQUENCE: 86

Gly Gly Gly Ser Leu
1               5

<210> SEQ ID NO 87
<211> LENGTH: 5
<212> TYPE: PRT
<213> ORGANISM: Artificial Sequence
<220> FEATURE:
<223> OTHER INFORMATION: Linker

<400> SEQUENCE: 87

Leu Gly Leu Gly Ser
1               5
```

```
<210> SEQ ID NO 88
<211> LENGTH: 5
<212> TYPE: PRT
<213> ORGANISM: Artificial Sequence
<220> FEATURE:
<223> OTHER INFORMATION: Linker

<400> SEQUENCE: 88

Gly Leu Gly Leu Ser
1               5

<210> SEQ ID NO 89
<211> LENGTH: 5
<212> TYPE: PRT
<213> ORGANISM: Artificial Sequence
<220> FEATURE:
<223> OTHER INFORMATION: Linker

<400> SEQUENCE: 89

Gly Leu Leu Gly Ser
1               5

<210> SEQ ID NO 90
<211> LENGTH: 5
<212> TYPE: PRT
<213> ORGANISM: Artificial Sequence
<220> FEATURE:
<223> OTHER INFORMATION: Linker

<400> SEQUENCE: 90

Leu Gly Gly Leu Ser
1               5

<210> SEQ ID NO 91
<211> LENGTH: 5
<212> TYPE: PRT
<213> ORGANISM: Artificial Sequence
<220> FEATURE:
<223> OTHER INFORMATION: Linker

<400> SEQUENCE: 91

Gly Leu Gly Gly Leu
1               5

<210> SEQ ID NO 92
<211> LENGTH: 5
<212> TYPE: PRT
<213> ORGANISM: Artificial Sequence
<220> FEATURE:
<223> OTHER INFORMATION: Linker

<400> SEQUENCE: 92

Leu Gly Leu Ser Gly
1               5

<210> SEQ ID NO 93
<211> LENGTH: 5
<212> TYPE: PRT
<213> ORGANISM: Artificial Sequence
<220> FEATURE:
<223> OTHER INFORMATION: Linker

<400> SEQUENCE: 93

Gly Leu Leu Ser Gly
1               5

<210> SEQ ID NO 94
```

<211> LENGTH: 5
<212> TYPE: PRT
<213> ORGANISM: Artificial Sequence
<220> FEATURE:
<223> OTHER INFORMATION: Linker

<400> SEQUENCE: 94

Gly Gly Leu Ser Leu
1               5

<210> SEQ ID NO 95
<211> LENGTH: 5
<212> TYPE: PRT
<213> ORGANISM: Artificial Sequence
<220> FEATURE:
<223> OTHER INFORMATION: Linker

<400> SEQUENCE: 95

Gly Gly Leu Leu Gly
1               5

<210> SEQ ID NO 96
<211> LENGTH: 5
<212> TYPE: PRT
<213> ORGANISM: Artificial Sequence
<220> FEATURE:
<223> OTHER INFORMATION: Linker

<400> SEQUENCE: 96

Gly Leu Gly Ser Leu
1               5

<210> SEQ ID NO 97
<211> LENGTH: 5
<212> TYPE: PRT
<213> ORGANISM: Artificial Sequence
<220> FEATURE:
<223> OTHER INFORMATION: Linker

<400> SEQUENCE: 97

Leu Gly Leu Ser Ser
1               5

<210> SEQ ID NO 98
<211> LENGTH: 5
<212> TYPE: PRT
<213> ORGANISM: Artificial Sequence
<220> FEATURE:
<223> OTHER INFORMATION: Linker

<400> SEQUENCE: 98

Gly Leu Gly Leu Ser
1               5

<210> SEQ ID NO 99
<211> LENGTH: 5
<212> TYPE: PRT
<213> ORGANISM: Artificial Sequence
<220> FEATURE:
<223> OTHER INFORMATION: Linker

<400> SEQUENCE: 99

Gly Gly Leu Leu Ser
1               5

<210> SEQ ID NO 100
<211> LENGTH: 5

-continued

```
<212> TYPE: PRT
<213> ORGANISM: Artificial Sequence
<220> FEATURE:
<223> OTHER INFORMATION: Linker

<400> SEQUENCE: 100

Gly Leu Gly Ser Leu
1               5

<210> SEQ ID NO 101
<211> LENGTH: 5
<212> TYPE: PRT
<213> ORGANISM: Artificial Sequence
<220> FEATURE:
<223> OTHER INFORMATION: Linker

<400> SEQUENCE: 101

Gly Leu Gly Ser Leu
1               5

<210> SEQ ID NO 102
<211> LENGTH: 10
<212> TYPE: PRT
<213> ORGANISM: Artificial Sequence
<220> FEATURE:
<223> OTHER INFORMATION: Linker

<400> SEQUENCE: 102

Leu Gly Gly Gly Ser Gly Gly Gly Gly Ser
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Linker

<400> SEQUENCE: 103

Gly Leu Gly Gly Ser Gly Gly Gly Gly Ser
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Linker

<400> SEQUENCE: 104

Gly Gly Leu Gly Ser Gly Gly Gly Gly Ser
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Linker

<400> SEQUENCE: 105

Gly Gly Gly Leu Ser Gly Gly Gly Gly Ser
1               5                   10

<210> SEQ ID NO 106
<211> LENGTH: 10
<212> TYPE: PRT
```

```
<213> ORGANISM: Artificial Sequence
<220> FEATURE:
<223> OTHER INFORMATION: Linker

<400> SEQUENCE: 106

Gly Gly Gly Gly Leu Gly Gly Gly Gly Ser
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Linker

<400> SEQUENCE: 107

Leu Gly Gly Ser Gly Gly Gly Gly Ser Gly
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Linker

<400> SEQUENCE: 108

Gly Leu Gly Ser Gly Gly Gly Gly Ser Gly
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Linker

<400> SEQUENCE: 109

Gly Gly Leu Ser Gly Gly Gly Gly Ser Gly
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Linker

<400> SEQUENCE: 110

Gly Gly Gly Leu Gly Gly Gly Gly Ser Gly
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Linker

<400> SEQUENCE: 111

Gly Gly Gly Ser Leu Gly Gly Gly Ser Gly
1               5                   10

<210> SEQ ID NO 112
<211> LENGTH: 10
<212> TYPE: PRT
<213> ORGANISM: Artificial Sequence
```

```
<220> FEATURE:
<223> OTHER INFORMATION: Linker

<400> SEQUENCE: 112

Gly Gly Gly Ser Leu Gly Gly Ser Gly
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Linker

<400> SEQUENCE: 113

Gly Leu Gly Ser Ser Gly Gly Gly Ser Ser
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Linker

<400> SEQUENCE: 114

Gly Gly Leu Ser Ser Gly Gly Gly Ser Ser
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Linker

<400> SEQUENCE: 115

Gly Gly Gly Leu Ser Gly Gly Gly Ser Ser
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Linker

<400> SEQUENCE: 116

Gly Gly Gly Ser Leu Gly Gly Gly Ser Ser
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Linker

<400> SEQUENCE: 117

Leu Gly Gly Gly Ser Leu Gly Gly Gly Ser
1               5                   10

<210> SEQ ID NO 118
<211> LENGTH: 10
<212> TYPE: PRT
<213> ORGANISM: Artificial Sequence
<220> FEATURE:
```

<223> OTHER INFORMATION: Linker

<400> SEQUENCE: 118

Gly Leu Gly Gly Ser Gly Leu Gly Gly Ser
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Linker

<400> SEQUENCE: 119

Gly Gly Leu Gly Ser Gly Gly Leu Gly Ser
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Linker

<400> SEQUENCE: 120

Gly Gly Gly Leu Ser Gly Gly Gly Leu Ser
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Linker

<400> SEQUENCE: 121

Gly Gly Gly Gly Leu Gly Gly Gly Gly Leu
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Linker

<400> SEQUENCE: 122

Leu Gly Gly Ser Gly Leu Gly Gly Ser Gly
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Linker

<400> SEQUENCE: 123

Gly Leu Gly Ser Gly Gly Leu Gly Ser Gly
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Linker

<400> SEQUENCE: 124

Gly Gly Leu Ser Gly Gly Gly Leu Ser Gly
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Linker

<400> SEQUENCE: 125

Gly Gly Gly Leu Gly Gly Gly Gly Leu Gly
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Linker

<400> SEQUENCE: 126

Gly Gly Gly Ser Leu Gly Gly Gly Ser Leu
1               5                   10

<210> SEQ ID NO 127
<211> LENGTH: 10
<212> TYPE: PRT
<213> ORGANISM: Artificial Sequence
<220> FEATURE:
<223> OTHER INFORMATION: Linker

<400> SEQUENCE: 127

Leu Gly Gly Ser Ser Leu Gly Gly Ser Ser
1               5                   10

<210> SEQ ID NO 128
<211> LENGTH: 10
<212> TYPE: PRT
<213> ORGANISM: Artificial Sequence
<220> FEATURE:
<223> OTHER INFORMATION: Linker

<400> SEQUENCE: 128

Gly Leu Gly Ser Ser Gly Leu Gly Ser Ser
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Linker

<400> SEQUENCE: 129

Gly Gly Leu Ser Ser Gly Gly Leu Ser Ser
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Linker

```
<400> SEQUENCE: 130

Gly Gly Gly Leu Ser Gly Gly Gly Leu Ser
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Linker

<400> SEQUENCE: 131

Gly Gly Gly Ser Leu Gly Gly Gly Ser Leu
1               5                   10
```